(12) United States Patent
Cohen et al.

(10) Patent No.: US 9,387,206 B2
(45) Date of Patent: *Jul. 12, 2016

(54) THERAPEUTIC APPROACHES FOR TREATING ALZHEIMER'S DISEASE

(71) Applicant: PHARNEXT, Issy les Moulineaux (FR)

(72) Inventors: Daniel Cohen, Saint Cloud (FR); Ilya Chumakov, Vaux-le-Penil (FR); Serguei Nabirochkin, Chatenay Malabry (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,849

(22) Filed: Aug. 18, 2014

(65) Prior Publication Data

US 2014/0357648 A1    Dec. 4, 2014

Related U.S. Application Data

(63) Continuation-in-part of application No. 13/462,034, filed on May 2, 2012, now Pat. No. 8,809,302, which is a continuation-in-part of application No. PCT/EP2010/066510, filed on Oct. 29, 2010.

(30) Foreign Application Priority Data

Nov. 3, 2009   (EP) ...................................... 09306048

(51) Int. Cl.
| | | |
|---|---|---|
| *A61K 31/495* | (2006.01) |
| *A61K 31/16* | (2006.01) |
| *A61K 45/06* | (2006.01) |
| *A61K 31/137* | (2006.01) |
| *A61K 31/185* | (2006.01) |
| *A61K 31/195* | (2006.01) |
| *A61K 31/343* | (2006.01) |
| *A61K 31/423* | (2006.01) |
| *A61K 31/197* | (2006.01) |
| *A61K 31/50* | (2006.01) |
| *A61K 31/64* | (2006.01) |

(52) U.S. Cl.
CPC ............. *A61K 31/495* (2013.01); *A61K 31/137* (2013.01); *A61K 31/185* (2013.01); *A61K 31/195* (2013.01); *A61K 31/197* (2013.01); *A61K 31/343* (2013.01); *A61K 31/423* (2013.01); *A61K 31/50* (2013.01); *A61K 31/64* (2013.01); *A61K 45/06* (2013.01)

(58) Field of Classification Search
CPC ..... A61K 31/495; A61K 31/16; A61K 45/06; A61K 31/137; A61K 31/185; A61K 2300/00
USPC .................................................. 514/255.01
See application file for complete search history.

(56) References Cited

U.S. PATENT DOCUMENTS

| | | | |
|---|---|---|---|
| 5,122,598 A * | 6/1992 | della Valle et al. ............. 536/20 |
| 6,391,922 B1 | 5/2002 | Fogel |
| 8,741,886 B2 * | 6/2014 | Cohen et al. .................. 514/183 |
| 8,809,302 B2 * | 8/2014 | Cohen et al. .................... 514/56 |
| 2001/0004640 A1 | 6/2001 | Inada et al. |
| 2001/0023246 A1 | 9/2001 | Barritault et al. |
| 2004/0102525 A1 | 5/2004 | Kozachuk |
| 2008/0188510 A1 | 8/2008 | Yoshino |
| 2009/0197958 A1 | 8/2009 | Sastry et al. |
| 2010/0029654 A1 | 2/2010 | Pasinetti |
| 2010/0137194 A1* | 6/2010 | Lawrence et al. ................. 514/8 |
| 2011/0230659 A1 | 9/2011 | Tsukamoto et al. |
| 2012/0058992 A1 | 3/2012 | Cohen et al. |

FOREIGN PATENT DOCUMENTS

| | | |
|---|---|---|
| EP | 1 563 846 | 8/2005 |
| EP | 1 837 034 | 9/2007 |
| WO | WO 01/58476 | 8/2001 |
| WO | WO 03/007993 | 1/2003 |
| WO | WO 03/080068 | 10/2003 |
| WO | WO 2007/053596 | 5/2007 |
| WO | WO 2008/006070 | 1/2008 |
| WO | WO 2008/143361 | 11/2008 |
| WO | WO 2009/133128 | 11/2009 |
| WO | WO 2009/133141 | 11/2009 |
| WO | WO 2009/133142 | 11/2009 |
| WO | WO 2010/061931 | 6/2010 |
| WO | WO 2011/054759 | 5/2011 |
| WO | WO 2012/117076 | 9/2012 |

OTHER PUBLICATIONS

Firuzi et al. 5-Lipoxygenase gene disruption reduces amyloid-beta pathology in a mouse model of Alzheimer's disease. FASEB J. 22, 1169-1178 (2008).*

(Continued)

*Primary Examiner* — Clinton Brooks
*Assistant Examiner* — Yih-Horng Shiao
(74) *Attorney, Agent, or Firm* — Saliwanchik, Lloyd & Eisenschenk

(57) ABSTRACT

The present invention relates to compositions and methods for the treatment of Alzheimer's disease and related disorders. More specifically, the present invention relates to novel combinatorial therapies of Alzheimer's disease and related disorders. In particular, the invention concerns compounds which, alone or in combination(s), can effectively modulate synapse function and/or angiogenesis and/or cell stress response. The invention also relates to methods of producing a drug or a drug combination for treating Alzheimer's disease and to methods of treating Alzheimer's disease or a related disorder.

8 Claims, 23 Drawing Sheets

(56) References Cited

OTHER PUBLICATIONS

Takamizawa et al. Bleomycin Stimulates Lung Fibroblasts to Release Neutrophil and Monocyte Chemotactic Activity. Journal of Immunology, 1999, 162: 6200-6208.*

Davy et al. Total blood volume in healthy young and older men. J. Appl. Physiol. 76(5):2059-2062, 1994.*

Akan, P. et al. "Pregnenolone protects the PC-12 cell line against amyloid beta peptide toxicity but its sulfate ester does not" *Chemico-Biological Interactions*, 2009, pp. 65-70, vol. 177, No. 1, XP-002613421.

Andrieu, S. et al. "Association of Alzheimer's Disease Onset With Ginkgo Biloba and Other Symptomatic Cognitive Treatments in a Population of Women Aged 75 Years and Older From the EPIDOS Study" *Journal of Gerontology: Medical Sciences*, Apr. 2003, pp. 372-377, vol. 58A, No. 4, XP-009144763.

Aplin, A. C. et al. "Vascular regression and survival are differentially regulated by MT1-MMP and TIMPs in the aortic ring model of angiogenesis" *Am. J. Physiol Cell Physiol*, Aug. 2009, pp. C471-C480, vol. 297, No. 2, XP-002613424.

Dobrek, L. et al. "Future Potential Indications for Pharmacotherapy Using Renin-Angiotensin-Aldosterone System Inhibitory Agents" *Adv. Clin. Exp. Med.*, May 2010, pp. 389-398, vol. 19, No. 3, XP-009144580.

Finsterer, J. et al. "Neurotoxocarosis" *Rev. Inst. Med. Trop. S. Paulo*, pp. 279-287, Sep.-Oct. 2007, vol. 49, No. 5, XP-002623261.

Kakinuma, Y. et al. "Donepezil, an acetylcholinesterase inhibitor against Alzheimer's dementia, promotes angiogenesis in an ischemic hindlimb model" *Journal of Molecular and Cellular Cardiology*, Apr. 2010, pp. 680-693, vol. 48, No. 4, XP-26949580.

Klein, H.E. et al. "Calcium antagonists in dementias. Assessment of the therapeutic efficacy" *Munchener Medizinische Wochenschrift*, 1995, pp. 38, 41-43, vol. 137, No. 47, XP-001525484.

Lee, S.T. et al. "Reduced circulating angiogenic cells in Alzheimer disease" *Neurology*, May 1, 2009, pp. 1858-1863, vol. 72, No. 21, XP-002610857.

Lu, Y. et al. "Neuroprotective activity and evaluation of Hsp90 inhibitors in an immortalized neuronal cell line" *Bioorganic & Medicinal Chemistry*, Feb. 2009, pp. 1709-1715, vol. 17, No. 4, XP-002613422.

Parnetti, L. et al. "Vascular Dementia Italian Sulodexide Study (VA. D.I.S.S.) Clinical and Biological Results" *Thrombosis Research*, pp. 225-233, vol. 87, No. 2, 1997.

Polizopoulou, Z. S. et al. "Evaluation of a Proposed Therapeutic Protocol in 12 Dogs with Tentative Degenerative Myelopathy" *Act Veterinaria Hungarica*, pp. 293-301, Sep. 2008, vol. 56, No. 3, XP-009142152.

Pooler, A. M. et al. "The 3-hydroxy-3-methylglutaryl co-enzyme A reductase inhibitor pravastatin enhances neurite outgrowth in hippocampal neurons" *Journal of Neurochemistry*, May 2006, pp. 716-723, vol. 97, No. 3, XP-002571001.

Roehl, A. B. et al. "Neuroprotective properties of levosimendan in an in vitro model of traumatic brain injury" *BMC Neurology*, Oct. 21, 2010, pp. 1-4, vol. 10, No. 1, XP-021074880.

Spuch, C. et al. "Induction of angiogenesis by implantation of encapsulated cells expressing vegf: A new therapy approach on Alzheimer's disease?" *Journal of Neurological Sciences*, Aug. 2009, p. 260, vol. 283, No. 1-2, Issue 1, XP-002571001.

Van Den Bussche, H. et al. "Prescription patterns and effectiveness perception of anti-dementia drugs—A comparison between General Practitioners, Neurologists and Psychiatrists" *Nervenheilkunde*, 2005, pp. 485-492, vol. 24, No. 6, XP-009144765.

Wang, B. et al. "Protective Effects of Wu-Zi-Yan-Zong-Fang on Amyloid β-induced Damage In Vivo and In Vitro" *Database Biosis [Online] Biosciences Information Service*, Aug. 2009, pp. 941-948, vol. 129, No. 8.

Yoshida, K. et al. "Eplerenone Enhances Neovascularization Induced by Endothelial Progenitor Cells in Rat Hindlimb Ischemia" *18th Scientific Meeting of the European-Society-of-Hypertension*, 22nd Scientific Meeting of the Inter, Berlin, Germany, Jun. 14-19, 2008, Poster session PJ-413, XP-009144604, abstract only.

Database Biosis [Online] Bioscience Information Service, Philadelphia, PA, Yoshihiko, K. et al. "Donepezil, an acetylcholiesterase inhibitor against Alzheimer's dementia, promotes angiogenesis in an ischemic limb model of nicotinic alpha 7 k0 mice" Database Accession No. PREV200800197710, Oct. 2007, pp. 1-2, vol. 116, No. 16, Suppl. S., XP-002613420.

Database Biosis [Online] Bioscience Information Service, Philadelphia, PA, Wang, B. et al. "Protective Effects of Wu-Zi-Yan-Zong-Fang on Amyloid β-induced Damage In Vivo and In Vitro" Database Accession No. PREV200900521928, Aug. 2009, pp. 1-2, vol. 129, No. 8, Suppl. S., XP-002613420.

Hama, A. et al. "Synergistic interaction between intrathecal gamma-aminobutyrate (GABA) receptor agonists and an N-methyl-D-aspartate (NMDA) receptor antagonist in rats with neuropathic spinal cord injury pain" *Society for Neuroscience Abstract Viewer and in Itinerary Planner*, 2010, p. 1, vol. 40.

Lyden, P.D. et al. "Combination therapy protects ischemic brain in rats. A glutamate antagonist plus a gamma-aminobutyric acid agonist" *Stroke*, 1994, pp. 189-196, vol. 25.

Costa, C. et al. "Coactivation of $GABA_A$ and $GABA_B$ Receptor Results in Neuroprotection During In Vitro Ischemia" *Stroke*, Jan. 15, 2004, pp. 596-600, vol. 35.

Zhou, C. et al. "Neuroprotection of γ-Aminobutyric Acid Receptor Agonists Via Enhancing Neuronal Nitric Oxide Synthase (Ser847) Phosphorylation Through Increased neuronal Nitric Oxide Synthase and PSD95 Interaction and Inhibited Protein Phosphatase Activity in Cerebral Ischemia" *Journal of Neuroscience Research*, 2008, pp. 2973-2983, vol. 86.

Louzada, P. R. et al. "Taurine prevents the neurotoxicity of β-amyloid and glutamate receptor agonists: activation of GABA receptors and possible implications for Alzheimer's disease and other neurological disorders" *The FASEB Journal*, Mar. 2004, vol. 18.

Engelhard, K. et al. "Der neuroprotektive Einfluss des Glutamat-Antagonisten Acamprosat nach experimenteller zerebraler Isch ämie" *Der Anaesthesist*, Sep. 22, 2000, pp. 816, 818, and 820, vol. 49, No. 9.

Zemlijic, G. et al. "Levosimendan Improves Renal Function in Patients With Advanced Chromic Heart Failure Awaiting Cardiac Transplantation" *Journal of Cardiac Failure*, Aug. 2007, pp. 417-421, vol. 13, No. 6.

Saba, H. I. et al. "Brief Report: Treatment of Bleeding in Hereditary Hemorrhagic Telangiectasia with Aminocaproic Acid" *The New England Journal of Medicine*, Jun. 23, 1994, pp. 1789-1790, vol. 330, No. 25.

* cited by examiner

THERAPEUTIC APPROACHES FOR TREATING ALZHEIMER'S DISEASE

FIELD OF THE INVENTION

The present invention relates to compositions and methods for the treatment of Alzheimer's disease (AD) and related disorders. More specifically, the present invention relates to novel combinatorial therapies of Alzheimer's disease and related disorders. In particular, the invention concerns compounds which, alone or in combination(s), can effectively modulate synapse function and/or angiogenesis and/or cell stress response. The invention also relates to methods of selecting a drug or a drug combination for treating Alzheimer's disease and to methods of treating Alzheimer's disease or a related disorder.

BACKGROUND OF THE INVENTION

AD is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved (1-4).

Incidence of Alzheimer's disease increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (5).

The incidence rate of AD increases dramatically with age. United Nations population projections estimate that the number of people older than 80 years will approach 370 million by the year 2050. Currently, it is estimated that 50% of people older than age 85 are afflicted with AD. Therefore, more than 100 million people worldwide will suffer from dementia in 50 years. The vast number of people requiring constant care and other services will severely affect medical, monetary and human resources (6).

Memory impairment is the early feature of the disease and involves episodic memory (memory for day-to-day events). Semantic memory (memory for verbal and visual meaning) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of Alzheimer's disease is sufficiently characteristic to allow identification in approximately 80% of cases (7). Nevertheless, clinical heterogeneity does occur and not only is this important for clinical management but provides further implication of specific medication treatments for functionally different forms (8).

The pathological hallmark of AD includes amyloid plaques containing beta-amyloid (Abeta), neurofibrillary tangles (NFT) containing Tau and neuronal and synaptic dysfunction and loss (9-11). For the last decade, two major hypotheses on the cause of AD have been proposed: the "amyloid cascade hypothesis", which states that the neurodegenerative process is a series of events triggered by the abnormal processing of the Amyloid Precursor Protein (APP) (12), and the "neuronal cytoskeletal degeneration hypothesis" (13), which proposes that cytoskeletal changes are the triggering events. The most widely accepted theory explaining AD progression remains the amyloid cascade hypothesis (14-16) and AD researchers have mainly focused on determining the mechanisms underlying the toxicity associated with Abeta proteins. On the contrary, Tau protein has received much less attention from the pharmaceutical industry than amyloid, because of both fundamental and practical concerns. Moreover, synaptic density change is the pathological lesion that better correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals (11).

SUMMARY OF INVENTION

The purpose of the present invention is to provide new therapeutic approaches for treating AD and related disorders.

The inventors have identified several drugs which, alone or in combination(s), can effectively affect pathways involved in AD and represent new and effective therapies for the treatment of AD and related disorders.

The invention therefore provides novel compositions and methods for treating AD and related disorders.

More particularly, the invention relates to a composition comprising a combination of at least two compounds chosen from the group consisting of aminocaproic acid, acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, levosimendan and zonisamide, or salts or prodrugs or derivatives or sustained release formulations thereof, for use in the treatment of Alzheimer's disease or a related disorder.

A further object of the present invention relates to a composition comprising a combination of at least two compounds chosen from the group consisting of aminocaproic acid, acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, levosimendan and zonisamide, or salts or prodrugs or derivatives or sustained release formulations thereof, for simultaneous, separate or sequential administration.

Most preferred drug combinations comprise 2, 3, 4 or 5 distinct drugs, even more preferably 2 or 3. Furthermore, the above drug combinations may also be used in further combination with additional drugs or treatments presently used for AD.

The invention also relates to a method of treating Alzheimer's disease or a related disorder, the method comprising simultaneously, separately or sequentially administering to a subject in need thereof a drug combination as disclosed above.

A further object of this invention is a method of treating Alzheimer's disease or a related disorder, the method comprising simultaneously, separately or sequentially administering to a subject in need thereof a drug combination that modulates synapse function and/or a drug that modulates angiogenesis and/or a drug that modulates cell stress response.

A further object of the invention resides in a method of producing drug(s) for treating Alzheimer's disease or a related disorder, the method comprising a step of testing candidate drug(s) for activity on synapse function and angiogenesis and cellular stress response and selecting candidate drug(s) that ameliorate(s) synapse function, attenuate(s) angiogenic dysregulation and modulate(s) cellular stress response.

The invention further relates to a method of producing a composition for treating Alzheimer's disease or a related disorder, the method comprising preparing a combination of a drug that modulates synapse function and/or a drug that attenuates angiogenic dysregulation and/or a drug that modulates cell stress response, for simultaneous, separate or sequential administration to a subject in need thereof.

Figure 1:
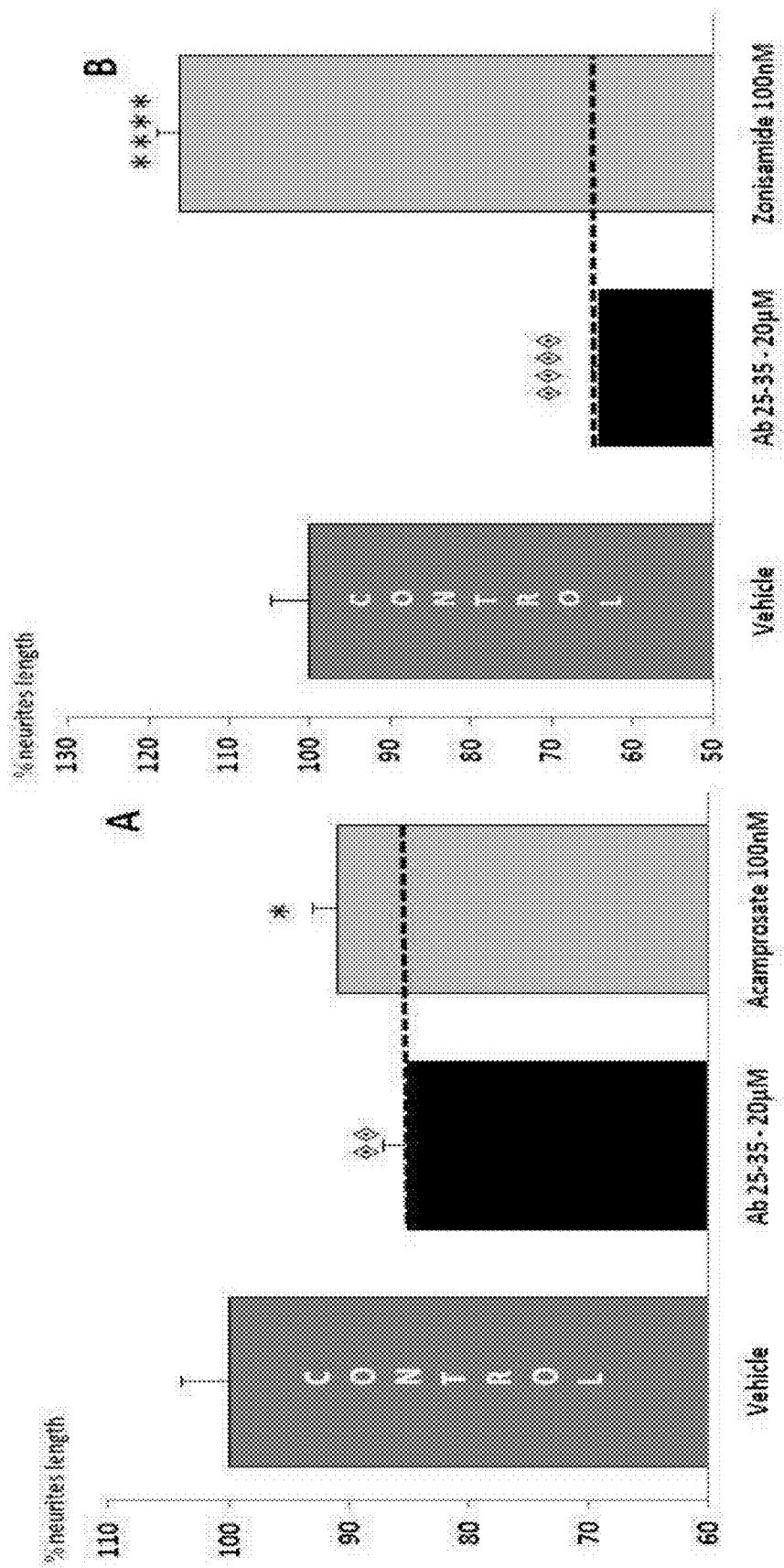
FIGS. 1A-1B: Effect of selected drugs on neurite outgrowth in beta-amyloid intoxicated rat primary cortical neuron culture. ◊◊: $p<0.01$; ◊◊◊◊: $p<0.00001$: significantly different from vehicle. *:$p<0.05$; ****:$p<0.0001$: significantly different from $A\beta_{25-35}$. Bilateral Student's t test. $A\beta_{25-35}$ 20 µM produces significant intoxication, above 25%, compared to vehicle-treated neurons. This intoxication is significantly prevented by either Acamprosate (FIG. 1A) or Zonisamide (FIG. 1B).

◊◊◊◊: $p<0.000001$: significantly different from vehicle. *:$p<0.05$; ***:$p<0.001$: significantly different from $A\beta_{25-35}$. Bilateral Student's t test. $A\beta_{25-35}$ 20 µM produces significant intoxication, above 25%, compared to vehicle-treated neurons (FIGS. 5A and B). This intoxication is significantly prevented by either Zonisamide (FIG. 5A) or Sulfisoxazole (FIG. 5B) or Leflunomide (FIG. 5C).

FIGS. 6A-6H: Effect of selected drugs pretreatment against human $A\beta_{1-42}$ injury in HBMEC. A) Validation of the experimental model used for drug screening: 1 hr of VEGF pre-treatment at 10 nM significantly protected the capillary network from this amyloid injury (+78% of capillary network compared to amyloid intoxication). *: $p<0.05$: significantly different from control (no intoxication) ◊: $p<0.05$: significantly different from amyloid intoxication (ANOVA+Dunnett Post-Hoc test). The intoxication is significantly prevented by Sulfisoxazole, Levosimendan, Terbinafine, Baclofen, Aminocaproic acid, Sulodexide, or Fenoldopam as shown in dose-response experiments, respectively in FIG. 6B, FIG. 6C, FIG. 6D, FIG. 6E, FIG. 6F, FIG. 6G, FIG. 6H. ◊: $p<0.05$: significantly different from the next dose; *: $p<0.05$: significantly different from amyloid intoxication (ANOVA+Dunnett Post-Hoc test).

FIGS. 7A-7G: Effect of selected drugs pretreatment on LDH release in human $A\beta_{1-42}$ toxicity on rat primary cortical cells. A) validation of the experimental model used for drug screening: 1 hr of BDNF (50 ng/ml) pre-treatment significantly protected the neurons from this amyloid injury (−62%), which is considered as a positive control for neuroprotection.*: $p<0.05$: significantly different from control (no intoxication) ◊: $p<0.05$: significantly different from amyloid intoxication (ANOVA+Dunnett Post-Hoc test). For all experiments, $A\beta_{1-42}$ produces significant intoxication compared to vehicle-treated neurons. The intoxication is significantly prevented by Baclofen (−86%) (B), Sulfisoxazole (−42%) (C), Levosimendan (−47%) (D), Etomidate (−50%) (E), Carbenoxolone (−39%) (F), and by Cinnarizine (−50%) (G), For all experiments, ◊: $p<0.05$: significantly different from $A\beta_{1-42}$ intoxication (ANOVA+Dunnett Post-Hoc test).

FIGS. 8A-8C: Effect of Sulfisoxazole and Levosimendan combination therapy on the total length of capillary network in beta-amyloid intoxicated HBMEC cultures. ◊: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication, above 40%, compared to vehicle-treated neurons. This intoxication is significantly prevented by the combination of Sulfisoxazole and Levosimendan (A) whereas, at those concentrations, Levosimendan (B) and Sulfisoxazole (C) alone have no significant effect on intoxication.

FIGS. 9A-9C: Effect of Sulfisoxazole and Terbinafine combination therapy on the total length of capillary network in beta-amyloid intoxicated HBMEC cultures. ◊: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication, above 40%, compared to vehicle-treated neurons. This intoxication is significantly prevented by the combination of Sulfisoxazole and Levosimendan (A) whereas, at those concentrations, Sulfisoxazole (B) and Terbinafine (C) alone have no significant effect on intoxication.

FIGS. 10A-10C: Effect of Baclofen and Levosimendan combination therapy on the total length of capillary network in beta-amyloid intoxicated HBMEC cultures. ◊: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication, above 40%, compared to vehicle-treated neurons. This intoxication is significantly prevented by the combination of Baclofen and Levosimendan (A) whereas, at those concentrations, Levosimendan (B) and Baclofen (C) alone have no significant effect on intoxication.

FIGS. 11A-11C: Effect of Terbinafine and Aminocaproic acid combination therapy on the total length of capillary network in beta-amyloid intoxicated HBMEC cultures. ◆: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication, above 40%, compared to vehicle-treated neurons. This intoxication is significantly prevented by the combination of Terbinafine and Aminocaproic acid (A) whereas, at those concentrations, Aminocaproic acid (B) and Terbinafine (C) alone have no significant effect on intoxication.

FIGS. 12A-12C: Effect of Aminocaproic acid and Levosimendan combination on the total length of capillary network in beta-amyloid intoxicated HBMEC cultures. ◆: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication, above 40%, compared to vehicle-treated neurons. This intoxication is significantly prevented by the combination of Levosimendan and Aminocaproic acid (A) whereas, at those concentrations, Aminocaproic acid (B) and Levosimendan (C) alone have no significant effect on intoxication.

FIGS. 13A-13C: Effect of Terbinafine and Levosimendan combination therapy on the total length of capillary network in beta-amyloid intoxicated HBMEC cultures. ◆: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication, above 40%, compared to vehicle-treated neurons. This intoxication is significantly prevented by the combination of Terbinafine and Levosimendan (A) whereas, at those concentrations, Terbinafine (B) and Levosimendan (C) alone have no significant effect on intoxication.

Figure 14:
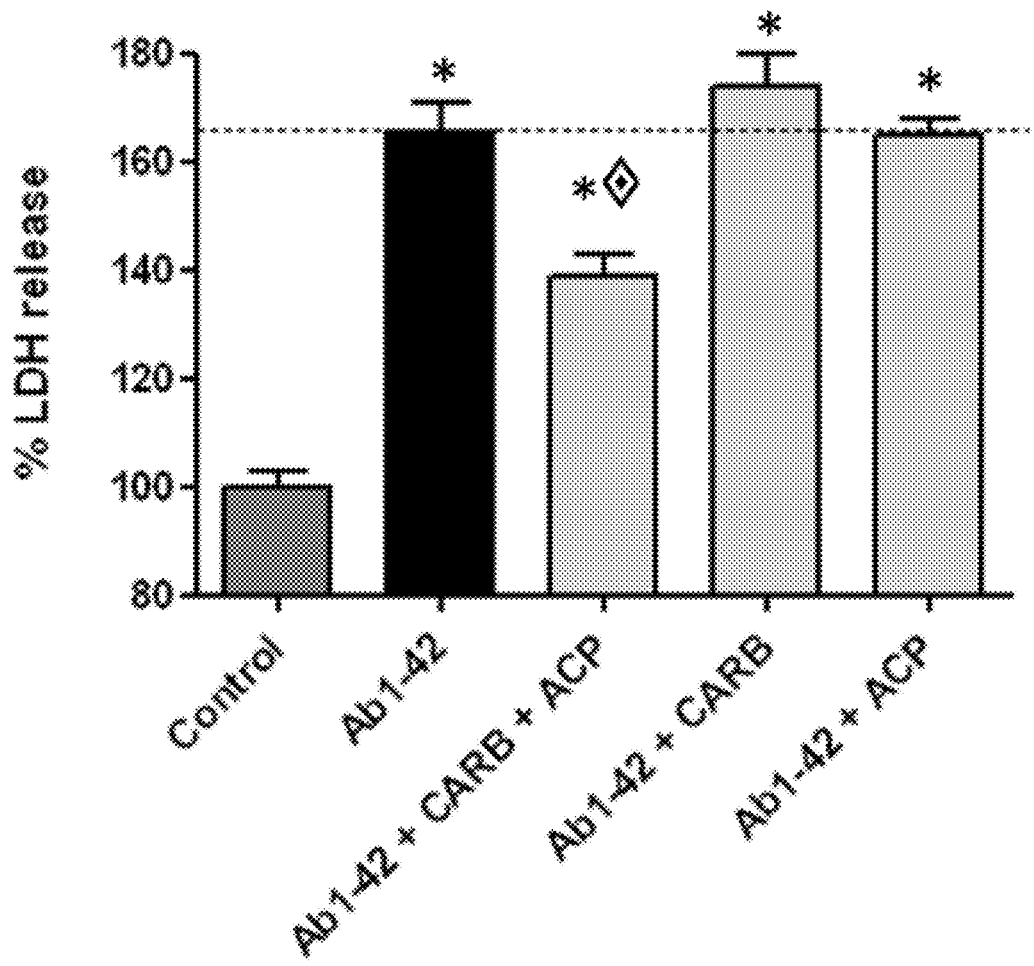

FIG. 14: Effect of Carbamazine (CARB) and Acamprosate (ACP) combination therapy on LDH release in human $A\beta_{1-42}$ toxicity on rat primary cortical cells. *: $p<0.05$: significantly different from control (no intoxication). ◆: $p<0.005$: significantly different from amyloid intoxication (ANOVA+Dunnett Post-Hoc test). The aggregated human amyloid peptide ($A\beta_{1-42}$ 2.5 µM) produces significant intoxication. This intoxication is significantly prevented by the combination of Carbamazine (0.32 nM) and Acamprosate (0.32 nM) whereas, at those concentrations, Carbamazine and Acamprosate alone have no significant effect on intoxication.

FIGS. 15A-15C: Effect of Sulfisoxazole and Sulodexide combination therapy on the total length of capillary network in beta-amyloid intoxicated HBMEC cultures. ◆: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication. This intoxication is significantly prevented by the combination of Sulfisoxazole (1.36 nM) and Sulodexide (0.002 LRU/mL) (A) whereas, at those concentrations, Sulfisoxazole (B) and Sulodexide (C) alone have no significant effect on intoxication.

Figure 16:
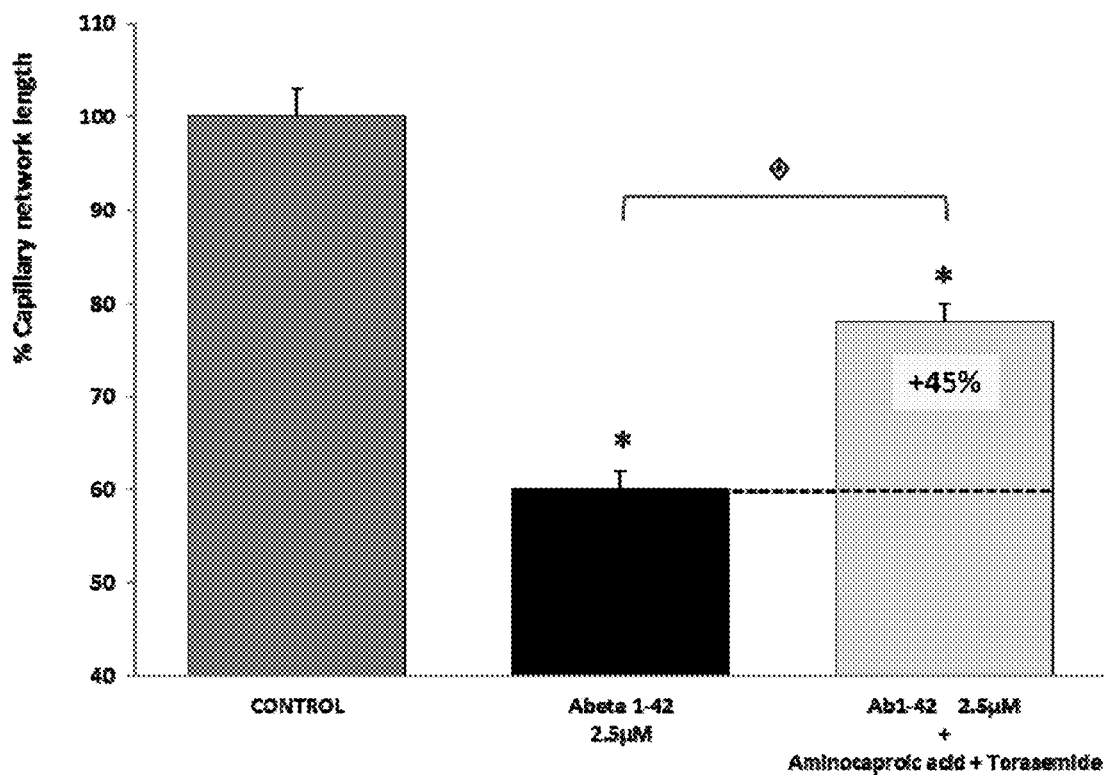

FIG. 16: Effect of Aminocaproic acid and Torasemide combination therapy on the total length of capillary network in beta-amyloid intoxicated HBMEC cultures. ◆: $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication. This intoxication is significantly prevented by the combination of Aminocaproic acid (160 nM) and Torasemide (400 nM).

Figure 17:
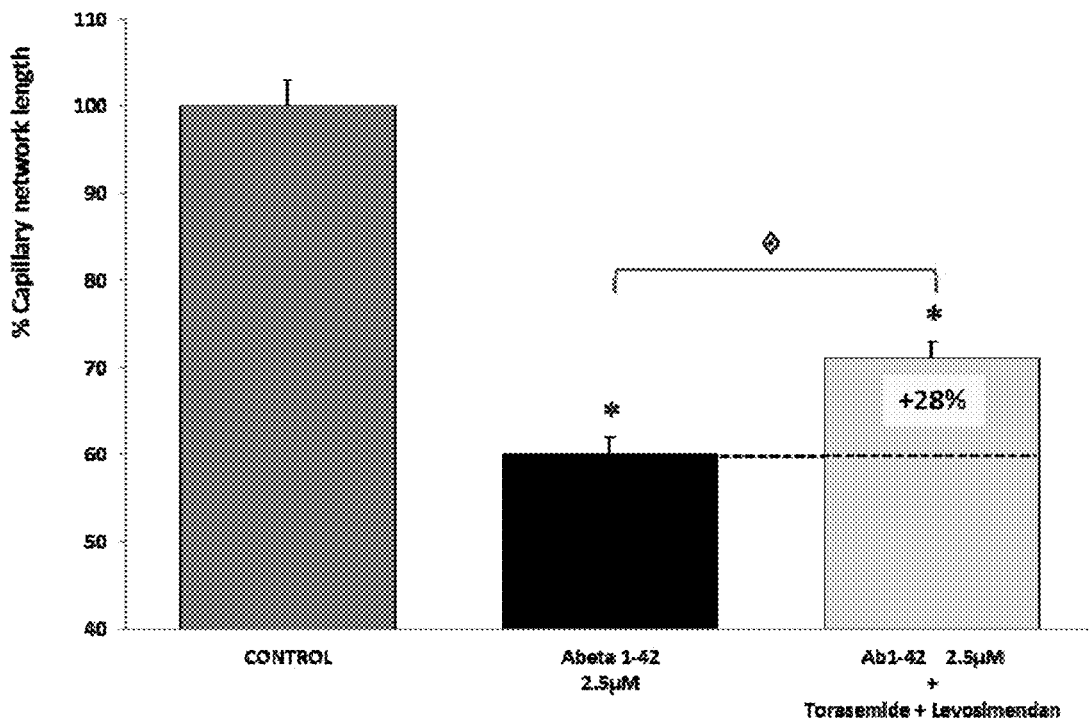

FIG. 17: Effect of Torasemide and Levosimendan combination therapy on the total length of capillary network in beta-amyloid intoxicated HBMEC cultures. ◆): $p<0.05$, significantly different from $A\beta_{1-42}$. *: $p<0.05$, significantly different from vehicle. ANOVA+Dunnett Post-Hoc test. The aggregated human amyloid peptide ($A\beta_{1-42}$ 2.5 µM) produces significant intoxication. This intoxication is significantly prevented by the combination of Torasemide (400 nM) and Levosimendan (1.6 nM).

Figure 18:
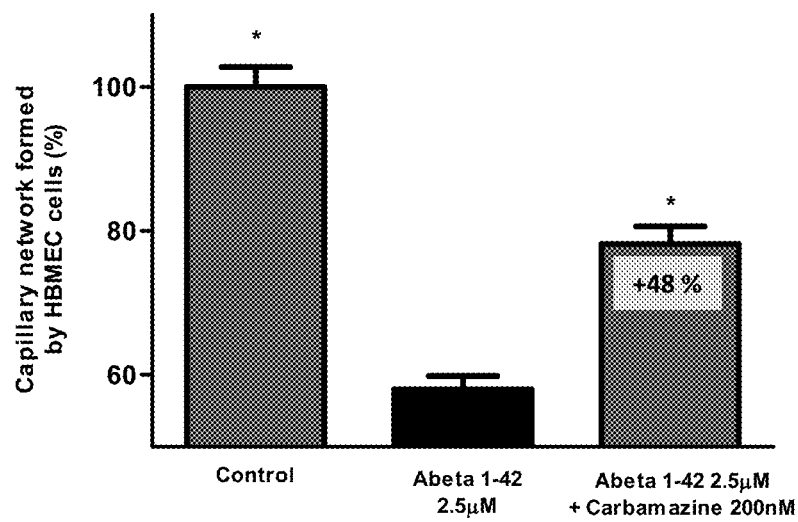

FIG. 18: Effect of carbamazine on the capillary network length in beta-amyloid intoxicated HBMEC cultures. *: $p<0.001$, significantly different from vehicle. ANOVA+Dunnett Post-Hoc test. The aggregated human amyloid peptide ($A\beta_{1-42}$ 2.5 µM) produces significant intoxication of HBMEC. This intoxication is significantly prevented by carbamazine (200 nM, +48%).

Figure 19:
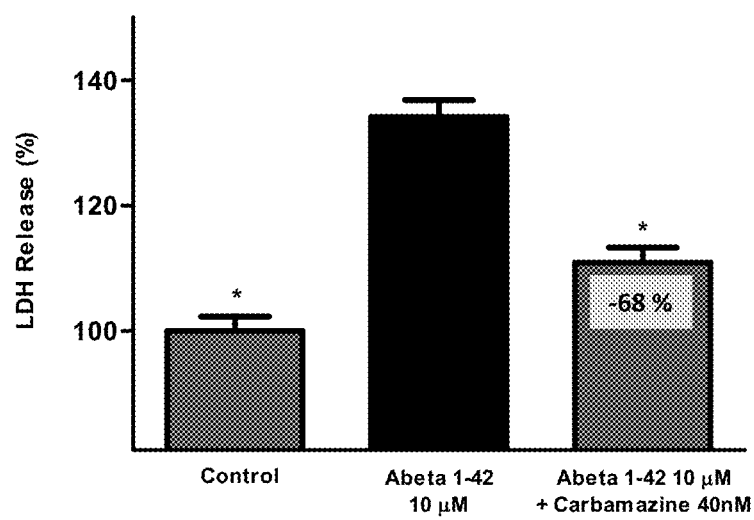

FIG. 19: Effect of carbamazine on LDH release in human $A\beta_{1-42}$ toxicity on rat primary cortical cells. *: $p<0.05$: significantly different from control (no intoxication). ◆: $p<0.005$: significantly different from amyloid intoxication (ANOVA+Dunnett Post-Hoc test). The aggregated human amyloid peptide ($A\beta_{1-42}$ 10 µM) produces significant intoxication of primary cortical cells. This intoxication is significantly prevented by carbamazine (40 nM, −68%).

DETAILED DESCRIPTION OF THE INVENTION

The present invention provides new therapeutic approaches for treating AD or related disorders. The invention discloses novel use of drugs or drug combinations which allow an effective correction of such diseases and may be used for patient treatment.

The term "AD related disorder" includes senile dementia of AD type (SDAT), Parkinson's disease, Lewis body dementia, vascular dementia, mild cognitive impairment (MCI), age-associated memory impairment (AAMI) and problems associated with aging, post-encephalitic Parkinsonism, amyotrophic lateral sclerosis (ALS), multiple sclerosis (MS) and Down syndrome.

As used herein, "treatment" of a disorder includes the therapy, prevention, prophylaxis, retardation or reduction of symptoms provoked by the disorder. The term treatment includes in particular the control of disease progression and associated symptoms.

The term "ameliorate", as it refers to synapse function, includes any increase in the synapse function as compared to the existing function in the subject. Such amelioration may include a restoration, i.e., to normal levels, or lower increase, which are still sufficient to improve the patient's condition. Such amelioration can be evaluated or verified using known biological tests, such as described in the experimental section.

The term "increase", as it refers to angiogenesis, includes any increase in the angiogenesis as compared to the existing level in the subject. Such amelioration may include a restoration, i.e., to normal levels, or lower increase, which are still sufficient to improve the patient's condition. Such an increase can be evaluated or verified using known biological tests, such as described in the experimental section.

The term "inhibit", as it refers to cell stress response ("CSR"), includes any reduction in the CSR as compared to the existing activity in the subject. Such reduction may include a partial diminution, e.g., from 5-20%, which is sufficient to improve the patient's condition, as well as more substantial reductions, e.g., from 20-50% or more complete inhibition, e.g., above 50%. The inhibition can be evaluated or verified using known biological tests, such as described in the experimental section.

Also, the designation of specific compounds within the context of this invention is meant to include not only the specifically named molecules, but also any pharmaceutically acceptable salts, hydrates, esters, ethers, isomers, racemates, conjugates, or pro-drugs thereof of any purity.

The term "combination or combinatorial treating/therapy" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

As discussed above, the invention relates to compositions and methods for treating Alzheimer's disease or a related disorder in a subject in need thereof, using particular drugs or drug combinations that ameliorate synapse function and/or increase angiogenesis and/or inhibit cell stress response.

By a comprehensive integration of experimental data covering results of cell biology studies, expression profiling experiments and genetic association studies describing different aspects of Alzheimer's disease and links existing in cellular signalling and functional pathways, the inventors have found that synapse function, angiogenesis and cell stress response represent important mechanisms which are altered in subjects having AD. By further experimental investigations, the inventors have selected drugs or drug combinations which effectively alter these pathways and which effectively improve AD, as illustrated in the examples. These drugs and combinations thus represent novel approaches for treating AD and related disorders.

Genes located in said functional networks and implicated in Alzheimer's disease were selected by the following criteria:

(1)—direct interaction with the genes causatively responsible for familial cases of Alzheimer's disease (APP, ApoE, presenilins, tau protein),
(2)—functional partners of the genes selected by the criterion (1), and
(3)—nearest functional partners of the genes selected by the criterion (2).

Through this process, the inventors have established that the networks responsible for synapse function, angiogenesis and cell stress response are major functional networks affected in Alzheimer's disease.

The inventors have more specifically established that the synaptic loss is a functionally-relevant hallmark of Alzheimer's disease, which ultimately leads to progressive cognitive decline, memory loss and dementia. Importantly, synaptic loss correlates better with cognitive deficit characterized Alzheimer pathology, compared to other AD-specific cellular lesion markers manifested in development of neurofibrillary tangles or deposition of amyloid plaques. Consequently, synapse organization and synaptic plasticity represent an important target for therapeutic interventions in the context of Alzheimer's disease.

APP protein is axonally transported and processed in presynaptic terminals, leading to high accumulation of Abeta at synapses. Oligomers of Abeta42 as well as amyloid plaques themselves are important for inhibiting long-term potentiation and are primarily responsible for memory impairment in AD patients.

Our data integration procedure revealed a group of genes, which are implicated in synaptic distortion in AD and which can be formally separated into three main functional groups: proteins participating in organization of post-synaptic density ("PSD") and correct nerve signal transmission at post-synaptic membranes; proteins assuring neurotransmitter release; and proteins involved in axon growth and developmental maturation of synaptic machinery.

In a particular embodiment, the present invention thus recognizes that it is important, for efficient treatment of AD, to ameliorate the activity of proteins involved in post-synaptic density.

Among genes identified by our analysis, the DLG2 gene, which encodes MAGUK family protein and creates an interface between clustered membrane-bound receptors, cell-adhesion molecules and actin-based cytoskeleton, represents a particular interest (17-18). The inventors have identified a large group of ionotrophic/metabotrophic glutamate and growth factor receptors, which interact directly with the DLG2 protein or DLG2/PSD95 protein complex at excitatory synapses and which can therefore be recognized as therapeutic targets for treating Alzheimer's disease.

In another particular embodiment, the present invention thus also recognizes that it is important, for efficient treatment of AD, to ameliorate the activity of proteins involved in the regulation of neurotransmitter release at the pre-synaptic membrane.

The release of neurotransmitters at a restricted and highly specialized active zone of the presynaptic plasma membrane is triggered by action potential and is controlled by combined actions of voltage-dependent calcium $Ca_v$ channels, MaxiK/BK channels (potassium large conductance calcium-activated channels) and cGMP-dependent PRKG protein kinases, all of which are tightly as associated, as demonstrated by our analysis, with development of Alzheimer's disease. In addition to these functional modules implicated in neurotransmitter release, the inventors have defined another group of proteins, linked to dysregulation of synaptic neurotransmission in the course of Alzheimer's disease, which are responsible for maturation, docking and fusion of synaptic vesicles (for instance, STX2, STXBP6, BIN1, RAB3B, UNC13C and RIMS1/2 scaffolding proteins). These functional pathways were therefore prioritized as appropriate therapeutic targets for treatment of Alzheimer's disease.

In another particular embodiment, the present invention further recognizes that it is important, for efficient treatment of AD, to ameliorate the activity of proteins involved in the regulation of axon growth and guidance.

Proteins participating in regulation of axon growth and guidance allow neuronal precursor cells and axons to migrate toward proper destinations to ensure correct location and connectivity; they are also involved in developmental maturation of newly established synapses as well as degradation of axons and synapses in AD. These processes play a fundamental role for execution of cognitive functions and seem to be extremely vulnerable to toxic effect of Abeta depositions.

Consecutive steps of axon growth and guidance are tightly controlled by combined actions of extracellular or membrane-tethered Netrins, Semaphorins, Ephrins, DLL and Slits molecules and their respective functional receptors, most of which were revealed by our data mining approach. Functional outcomes of activation of most axon growth receptors are tightly connected with their ability to differentially modulate activity of small GTPases RhoA, Rac1 and Cdc42, with the RhoA GTPase being mainly responsible for neurite retraction and growth cone collapse (19). These signalling pathways have been recognized as pertinent therapeutic targets for treatment of Alzheimer's disease.

Thus, the present invention recognizes that it is important, for efficient treatment of AD, to ameliorate synapse function altered in Alzheimer's disease and other neurodegenerative disorders, by modulating target genes and protein described above.

Through the data mining process, the inventors have also established that the network responsible for angiogenesis represents another major functional network affected in Alzheimer's disease.

Angiogenesis plays a fundamental role in ensuring a tissue homeostasis and in adaptive responses to environmental and physiological challenges such as hypoxia or wound healing; its dysfunction contributes to the pathogenesis of numerous and heterogeneous pathologies varying from cardiovascular complications to tumour growth and metastasis.

Although Alzheimer's disease is traditionally considered as a neurodegenerative condition accompanied by collateral vascular pathology, our analysis allow re-evaluation of the pathogenic impact of the vascular deregulation and attribute an important and probably causative role to angiogenic pathways in aetiology of this disease. The inventors have found that genes regulating angiogenesis are extremely enriched in signalling networks implicated in Alzheimer's disease. This conclusion has deep consequences for prevention and curing of Alzheimer's disease and provides new guidelines for combinatorial treatment of this complex neurodegenerative disorder.

Among signalling pathways tightly implicated in vascular remodelling associated with Alzheimer's disease, several functional modules mediated by VEGFR1, ErbB4, Notch, DCC, CD44, ephrin receptors and cadherins have been identified.

As revealed by our data mining approach, other target proteins potentially involved in development of vascular defects manifested in course of Alzheimer's disease include IL20Rα, LEPTR, NRP1 and NRP2, and endothelin EDNRA receptors, proteins participating in organization and remodelling of extracellular matrix (THBS2, LAMA1, COL4A2, ADAMTS12 and ADAM10) or proteins (for instance, TLL2) playing an important role in functional processing of well-known angiogenic modulators such as prolactin, growth hormone, and placental lactogen (20).

Further, we have also discovered that several genes associated with Alzheimer's disease represent upstream modulators and down-stream effectors of the AMP-activated kinases, important regulators of the vascular system (for instance, leptin and CNTF receptors, trombin signalling pathway, CAMKK2β and LKB1 kinases) (21-24). This finding allowed us to define the AMPK-mediated signalling network as a reasonable therapeutic target for treatment of Alzheimer's disease.

Phosphatidic acid (PA), lysophosphatidic acid (LPA), and sphingosine 1-phosphate (S1P) are natural phospholipids that possess potent signaling properties. Notably, these phospholipid growth factors display divergent effects on the angiogenic potential of endothelial cells (25). Using our data mining approach, we identified a large number of genes involved in LPA metabolism or modulated by LPA signaling and potentially linked to progression of Alzheimer's disease (MTR, MAT2B, CUBN, ATP10A, THEM2, PITPNC1, ENPPG, SGPP2, AGPAT, DGKH, DGKB, MGST2, PLD2, and DRD2). Therefore, we concluded that this signaling network represents a suitable therapeutic target for treatment of Alzheimer's disease.

The present invention also emphasizes the importance of increasing angiogenesis altered in Alzheimer's disease and other neurodegenerative disorders, by modulating target genes and protein described above.

Finally, we have established that the network responsible for cell stress response is the third major functional network affected in Alzheimer's disease.

We have more specifically established that cell stress response is a functionally-relevant hallmark of Alzheimer's disease. As discussed below, the inventors have identified three families of proteins within the cell stress response network which are functionally relevant to the genesis and control of Alzheimer's disease, and represent valuable targets for combination therapies. These groups of proteins are, more specifically, proteins participating in calcium homeostasis, in protein folding, and in execution of apoptosis.

In a particular embodiment, the present invention more specifically relates to compositions and methods using a drug combination that modulates the activity of a protein involved in calcium homeostasis.

Calcium, one of the most important intracellular messengers, mediates a pleiotropy of cellular processes in both neuronal and endothelial cells, including synaptic plasticity, angiogenesis and apoptosis.

Intracellular calcium level is precisely regulated by cooperative action of a series of calcium permeable channels, calcium pumps and calcium exchangers in the plasma membrane and endoplasmatic reticulum (26-27). We have identified a network of genes implicated in the calcium homeostasis pathway, whose function could be modified by mutant presenilin proteins or by toxic β-amyloid in course of Alzheimer's disease. Among them, IP3R (ITPR1) and RYR3 receptors, ATP2A3 (SERCA3 Ca2+ ATPase) regulating calcium homeostasis on the level of ER, plasma membrane ATPase ATP2B1, extruding calcium ions from eukaryotic cells against concentration gradients, and voltage-gated Na+ channels represent particular interest as potential therapeutic targets for treatment of Alzheimer's disease.

In another particular embodiment, the present invention more specifically relates to compositions and methods using a drug combination that modulates the activity of a protein involved in protein folding or aggregation.

Protein aggregation is a central cytopathological phenomenon in AD. Two major cellular hallmarks of Alzheimer's disease are manifested in the development of neurofibrillary tangles (NFTs) and deposition of amyloid plaques, composed of aggregated hyperphosphorylated tau protein and Aβ fragments of APP protein respectively. Another protein prone to aggregation, α-synuclein, recognized as a rather specific hallmark of Parkinson's Disease, can nevertheless be detected in amyloid plaques in most cases of sporadic and familial forms of Alzheimer's disease.

We have determined several genes implicated in the modulation of folding, posttranslational modification and processing of every major constituent of Alzheimer's disease-associated protein aggregations as pertinent therapeutic targets for treatment of Alzheimer's disease—for instance, APBA1 and APBA2BP proteins that interact with APP and regulate its stability and functions, or PARK2 ubiquitin-protein ligase that is implicated in clearance of α-synuclein (28). Also, the GSK-3β kinase might play a particularly important role in pathogenesis of protein misfolding in the course of Alzheimer's disease. This conclusion is reinforced by our finding that a few signalling modules regulating GSK-3β kinase activity and its interaction with tau protein—WWOX (29), hyaluronan CD44 receptor, Wnt receptors Fz2/ROR2 and insulin receptor/PTPRG phosphatase complex (30)—are associated with progression of Alzheimer's disease.

In a further particular embodiment, the present invention relates to compositions and methods using a drug combination that inhibits apoptosis that is recognized as a major cellular mechanism responsible for cellular loss in Alzheimer's disease.

As identified by our analysis, apoptosis in the case of Alzheimer's disease, most likely, is executed via canonical p53-dependent pathways.

The p53 protein can be regulated through post-translational modifications and through interactions with positive and negative regulatory factors. We have identified several such regulatory proteins—WWOX, MDM1, HIPK2 and PML—confirming the proposal about the pivotal role of the p53 protein in cell death execution in Alzheimer's disease (31-33).

Among the receptor systems that could be directly and specifically implicated in induction of apoptosis in the context of Alzheimer's disease, UNC5C (Unc-5 Homolog C) and DCC (Deleted in Colorectal Carcinoma) netrin receptors, involving in axon guidance and angiogenesis, represent particular interest. These receptors are designated putative conditional tumor suppressors, since they behave as netrin-dependent receptors inducing apoptosis in the absence of their ligand (34). Binding of netrin-1 to these receptors inhibits p53-dependent apoptosis, while p53 is directly involved in transcriptional regulation of netrin-1 and its receptors (33). Additionally, the DCC receptor is known to be processed by presenilin, indicating its important role in development of Alzheimer's disease (35). Thus, our data mining suggests that netrin receptor-dependent and p53-mediated programmed cell death could be one of the specific pro-apoptotic pathways implicated in pathological cell loss in the context of Alzheimer's disease, in addition to rather unspecific pro-apoptotic programs stimulated by disrupted calcium homeostasis and excessive ROS production.

In a particular embodiment, the present invention more specifically relates to compositions and methods using a drug combination that inhibits the activity of at least two distinct proteins involved in calcium homeostasis, in protein folding, and in execution of apoptosis.

In a preferred embodiment, the present invention proposes novel compositions which can be used to inhibit cell stress response induced in Alzheimer's disease and other neurodegenerative disorders by modulating target genes and proteins described above.

As discussed above, the invention relates to compositions and methods for treating Alzheimer's disease or a related disorder in a subject in need thereof, using a combination of drugs that ameliorate synapse function and/or increase angiogenesis and/or inhibit cell stress response.

More specifically, the inventors have selected and tested a number of drugs or drug combinations which alter one or, preferably, all of the above described pathways. As disclosed in the examples, these drug combinations have a strong effect on Alzheimer's disease and represent new therapeutic approaches of the pathology. These drug combinations are particularly advantageous because they affect different pathways and thus are more effective. Also, because of their efficacy and mode of action, the drug combinations can be used at low dosages, which is a further very substantial advantage.

The most preferred drugs are listed in Table 1 below.

TABLE 1

| DRUG NAME | CAS NUMBER |
|---|---|
| Acamprosate | 77337-76-9 |
| Ambrisentan | 177036-94-1 |
| Aminocaproic Acid | 60-32-2 |
| Amlodipine | 88150-42-9 |
| Amobarbital | 57-43-2 |
| Aprindine | 37640-71-4 |
| Argatroban | 74863-84-6 |
| Baclofen | 1134-47-0 |
| Benidipine | 105979-17-7 |
| Carbamazepine | 298-46-4 |
| Carbamazine | 90-89-1 |
| Carbenoxolone | 5697-56-3 |
| Cefmenoxime | 65085-01-0 |
| Cefotetan | 69712-56-7 |
| Ciclopirox | 29342-05-0 |
| Cilostazol | 73963-72-1 |
| Cinacalcet | 226256-56-0 |
| Cinnarizine | 298-57-7 |
| Clopidogrel | 113665-84-2 |
| Dyphylline | 479-18-5 |
| Enprofylline | 41078-02-8 |
| Eplerenone | 107724-20-9 |
| Eprosartan | 133040-01-4 |
| Erythrityl tetranitrate | 7297-25-8 |
| Etomidate | 33125-97-2 |
| Fenoldopam | 67227-57-0 |
| Leflunomide | 75706-12-6 |
| Lercanidipine | 100427-26-7 |
| Levosimendan | 141505-33-1 |
| Mepacrine | 83-89-6 |
| Methimazole | 60-56-0 |
| Methyclothiazide | 135-07-9 |
| Mitiglinide | 145375-43-5 |
| Moxifloxacin | 354812-41-2 |
| Oxtriphylline | 4499-40-5 |
| Paramethadione | 115-67-3 |
| Phenformin | 114-86-3 |
| Prilocaine | 721-50-6 |
| Rifabutin | 72559-06-9 |
| Risedronate | 105462-24-6 |
| Sulfisoxazole | 127-69-5 |
| Sulodexide | 57821-29-1 |
| Tadalafil | 171596-29-5 |
| Terbinafine | 91161-71-6 |
| Torasemide | 56211-40-6; 72810-59-4 |
| Zonisamide | 68291-97-4 |

In this regard, a preferred object of this invention relates to compositions comprising a combination of at least two compounds chosen from the group consisting of aminocaproic acid, acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, levosimendan and zonisamide, or salts or prodrugs or derivatives of any purity or sustained release formulations thereof, for simultaneous, separate or sequential administration.

In a particular embodiment, the invention relates to compositions comprising at least one compound chosen from the group consisting of aminocaproic acid, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine and levosimendan, or salt(s) or prodrug(s) or derivative(s) or sustained release formulation(s) thereof, in combination with at least one compound chosen from the group consisting of acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide and zonisamide, or salt(s) or prodrug(s or derivative(s) or sustained release formulation(s) thereof, for simultaneous, separate or sequential administration.

As disclosed in the examples, combination therapies using at least 2 of the above-listed drugs lead to an efficient correction of Alzheimer's disease.

Therapy according to the invention may be performed alone or as a drug combination.

In a preferred embodiment, the drugs of the invention are used in combination(s) for combined, separate or sequential administration, in order to provide the most effective effect. In this respect, the compositions of treating Alzheimer's disease according to the invention use drug(s) that ameliorate synapse function and drug(s) that attenuate angiogenesis and/or drug(s) that inhibit cell stress response.

More specifically, the compositions according to the invention, for use in the treatment of Alzheimer's disease or a related disorder, may be selected from compositions comprising at least one of the following combinations of drugs:

- a modulator of AMPK (preferably, phenformin) and an inhibitor of sodium channel SCN1A and an activator of BK channels (preferably, zonisamide) or a modulator of BK channels (preferably, methyclothiazide),
- a modulator of AMPK (preferably, phenformin) and a modulator of GABAergic and glutamatergic receptors activity (preferably selected from acamprosate, etomidate and aprindine),
- a modulator of AMPK (preferably, phenformin) and an antagonist of EDNRA endothelin receptor (preferably, sulfisoxazole),
- an inhibitor of sodium channel SCN1A and an activator of BK channels (preferably, zonisamide) or a modulator of BK channels (preferably, methyclothiazide) and a modulator of RYR3 ryanodine receptor (preferably, prilocaine),
- a modulator of GABBR2 receptor (preferably, baclofen) and a modulator of RHOA (preferably selected from terbinafine and risedronate),
- a modulator of GABBR2 receptor (preferably, baclofen) and an antagonist of EDNRA endothelin receptor (preferably, sulfisoxazole),
- a modulator of GABBR2 receptor (preferably, baclofen) and an inhibitor of sodium channel SCN1A and an activator of BK channels (preferably, zonisamide) or a modulator of BK channels (preferably, methyclothiazide),
- a modulator of GABBR2 receptor (preferably, baclofen) and a modulator of HAS1-3 hyaluronan synthases (preferably, leflunomide),
- an inhibitor of sodium channel SCN1A and an activator of BK channels (preferably, zonisamide) or a modulator of BK channels (preferably, methyclothiazide) and a modulator of adenosine receptors ADORAL/2/3 (preferably, dyphylline),
- an inhibitor of sodium channel SCN1A and an activator of BK channels (preferably, zonisamide) or a modulator of BK channels (preferably, methyclothiazide) and an antagonist of EDNRA endothelin receptor (preferably, sulfisoxazole),
- a modulator of RHOA (preferably selected from terbinafine and risedronate) and an antagonist of EDNRA endothelin receptor (preferably, sulfisoxazole),
- a modulator of RHOA (preferably selected from terbinafine and risedronate) and an inhibitor of phospholipases PLA1A and PLA2 (preferably, mepacrine),
- a modulator of RHOA (preferably selected from terbinafine and risedronate) and a modulator of GABAergic and glutamatergic receptors activity (preferably selected from acamprosate, etomidate and aprindine),
- a modulator of RHOA (preferably selected from terbinafine and risedronate) and a chemical chaperon (preferably, rifabutin),
- a modulator of AMPK (preferably, phenformin) and an inhibitor of PDE11A and PDE4A, PDE5A phosphodiesterases (preferably selected from tadalafil, enprofylline and oxtriphylline),
- an inhibitor of sodium channel SCN1A and an activator of BK channels (preferably, zonisamide) or a modulator of BK channels (preferably, methyclothiazide) and a modulator of trombin receptor F2R signalling (preferably, argatroban and cefmenoxime),
- a modulator of AMPK (preferably, phenformin) and a modulator of purinergic receptors P2RY1 and P2RY12 (preferably, clopidogrel),
- a modulator of GABAergic and glutamatergic receptors activity (preferably selected from acamprosate, etomidate and aprindine) and a modulator of CASR (preferably, cinacalcet),
- an antagonist of EDNRA endothelin receptor (preferably, sulfisoxazole) and a modulator of CASR (preferably, cinacalcet),
- a modulator of RHOA (preferably selected from terbinafine and risedronate) and a modulator of trombin receptor F2R signalling (preferably selected from argatroban and cefmenoxime),
- a modulator of GABBR2 receptor (preferably, baclofen) and a modulator of purinergic receptors P2RY1 and P2RY12 (preferably, clopidogrel),
- a modulator of RHOA (preferably selected from terbinafine and risedronate) and a modulator of purinergic receptors P2RY1 and P2RY12 (preferably, clopidogrel),
- an inhibitor of sodium channel SCN1A and an activator of BK channels (preferably, zonisamide) or a modulator of BK channels (preferably, methyclothiazide) and an antagonist of voltage-gated calcium CACNA channels (preferably selected from cinnarizine, benidipine, paramethadione and amlodipine),
- a modulator of GABAergic and glutamatergic receptors activity (preferably selected from acamprosate, etomidate and aprindine) and an antagonist of voltage-gated calcium CACNA channels (preferably selected from cinnarizine, benidipine, paramethadione and amlodipine),
- an inhibitor of sodium channel SCN1A and an activator of BK channels (preferably, zonisamide) or a modulator of BK channels (preferably, methyclothiazide) and a modulator of HIF1A signalling (preferably, ciclopirox),
- a modulator of GABAergic and glutamatergic receptors (preferably selected from acamprosate, etomidate and aprindine) and a modulator of HIF1A signalling (preferably, ciclopirox), an antagonist of EDNRA endothelin receptor (preferably, sulfisoxazole) and a modulator of oxidative phosphorylation (preferably selected from amobarbital and methimazole), an inhibitor of sodium channel SCN1A and an activator of BK channels (preferably, zonisamide) or a modulator of BK channels (preferably, methyclothiazide) and a modulator of oxidative phosphorylation (preferably selected from amobarbital and methimazole), an antagonist of EDNRA endothelin receptor (preferably, sulfisoxazole) and a modulator of vitamin K metabolism (preferably, cefotetan), an inhibitor of sodium channel SCN1A and an activator of BK channels (preferably, zonisamide) or a modulator of BK channels (preferably, methyclothiazide) and a modulator of vitamin K metabolism (preferably, cefotetan), a modulator of GABAergic and glutamatergic receptors activity (preferably selected from acamprosate, etomidate and aprindine) and a modulator of PRKG1 (preferably, erythrityl tetranitrate), an inhibitor of sodium channel SCN1A and an activator of BK channels (preferably, zonisamide) or a modulator of BK channels (preferably, methyclothiazide) and a modulator of PRKG1 (preferably, erythrityl tetranitrate), an antagonist of EDNRA endothelin receptor (preferably, sulfisoxazole) and a modulator of PRKG1 (preferably, erythrityl tetranitrate), a modulator of KCNJ11 (preferably selected from mitiglinide and levosimendan) and a modulator of PRKG1 (preferably, erythrityl tetranitrate), a modulator of KCNJ11 (preferably selected from mitiglinide and levosimendan) and an inhibitor of sodium channel SCN1A and an activator of BK channels (preferably, zonisamide) or a modulator of BK channels (preferably, methyclothiazide), and a modulator of KCNJ11 (preferably selected from mitiglinide and levosimendan) and a modulator of RHOA (preferably selected from terbinafine and risedronate).

In the most preferred embodiment, the invention relates to any combination of compounds selected from aminocaproic acid, acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, levosimendan and zonisamide, or salt(s) or prodrug(s) or derivative(s) or sustained release formulations thereof, for use in the treatment of Alzheimer's disease or a related disorder.

In a particular embodiment, a composition of the invention, for use in the treatment of Alzheimer's disease or a related disorder, comprises at least one compound chosen from the group consisting of aminocaproic acid, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine and levosimendan, or salt(s) or prodrug(s) or derivative(s) or sustained release formulation(s) thereof, in combination with at least one compound chosen from the group consisting of acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide and zonisamide, or salt(s) or prodrug(s) or derivative(s) or sustained release formulation(s) thereof.

Another particularly preferred embodiment of the invention relates to a composition for treating Alzheimer's disease (AD) or a related disorder in a subject in need thereof, comprising at least aminocaproic acid, or salt(s) or prodrug(s) or derivative(s) or sustained release formulation(s) thereof. In a particular embodiment, aminocaproic acid is used in combination with at least one additional compound preferably selected from acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, levosimendan, and zonisamide, or salts or prodrugs or derivatives or sustained release formulations thereof, for combined, separate or sequential administration.

A preferred composition of the invention comprises aminocaproic acid, or salt(s) or prodrug(s) or derivative(s) or sustained release formulation(s) thereof, and at least one additional compound selected from baclofen, sulfisoxazole, terbinafine, torasemide, and levosimendan, or salts or prodrugs or derivatives or sustained release formulations thereof, for combined, separate or sequential administration. Such a composition per se also represents a particular object of the invention.

The invention also relates to a method of treating Alzheimer's disease (AD) or a related disorder in a subject in need thereof, comprising administering to the subject an effective amount of aminocaproic acid, or salt(s) or prodrug(s) or derivative(s) or sustained release formulation(s) thereof, preferably in combination as disclosed above.

Another particularly preferred embodiment of the invention relates to a composition for treating Alzheimer's disease (AD) or a related disorder in a subject in need thereof, comprising at least levosimendan, or salt(s) or prodrug(s) or derivative(s) or sustained release formulation(s) thereof. In a particular embodiment, levosimendan is used in combination with at least one additional compound preferably selected from aminocaproic acid, acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, and zonisamide, or salts or prodrugs or derivatives or sustained release formulations thereof, for combined, separate or sequential administration.

A preferred composition of the invention comprises levosimendan, or salt(s) or prodrug(s) or derivative(s) or sustained release formulation(s) thereof, and at least one additional compound selected from aminocaproic acid, baclofen, sulfisoxazole, terbinafine, and torasemide, or salts or prodrugs or derivatives or sustained release formulations thereof, for combined, separate or sequential administration. Such a composition per se also represents a particular object of the invention.

The invention also relates to a method of treating Alzheimer's disease (AD) or a related disorder in a subject in need thereof, comprising administering to the subject an effective amount of levosimendan, or salt(s) or prodrug(s) or derivative(s) or sustained release formulation(s) thereof, preferably in combination as disclosed above.

Another particularly preferred embodiment of the invention relates to a composition for treating Alzheimer's disease (AD) or a related disorder in a subject in need thereof, the composition comprising at least Eplerenone, Carbenoxolone, Sulodexide, Cinnarizine, or carbamazine, or salt(s) or prodrug(s) or derivative(s) or sustained release formulation(s) thereof.

In a particular embodiment, Eplerenone, Carbenoxolone, Sulodexide, Cinnarizine, or carbamazine is used in combination with at least one additional compound preferably selected from levosimendan, aminocaproic acid, acamprosate, amlodipine, argatroban, baclofen, cilostazol, cinacalcet, clopidogrel, dyphylline, fenoldopam, leflunomide, mepacrine, methimazole, phenformin, prilocaine, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefmenoxime, aprindine, etomidate, mitiglinide, benidipine, and zonisamide, or salts or prodrugs or derivatives or sustained release formulations thereof, for combined, separate or sequential administration.

A preferred composition of the invention comprises Eplerenone, Carbenoxolone, Sulodexide, Cinnarizine, or carbamazine, or salt(s) or prodrug(s) or derivative(s) or sustained release formulation(s) thereof, and at least one additional compound selected from levosimendan, aminocaproic acid, baclofen, sulfisoxazole, terbinafine, and torasemide, or salts or prodrugs or derivatives or sustained release formulations thereof, for combined, separate or sequential administration. Such a composition per se also represents a particular object of the invention.

The invention also relates to a method of treating Alzheimer's disease (AD) or a related disorder in a subject in need thereof, comprising administering to the subject an effective amount of Eplerenone, Carbenoxolone, Sulodexide, Cinnarizine, or carbamazine, or salt(s) or prodrug(s) or derivative(s) or sustained release formulation(s) thereof, preferably in combination as disclosed above.

More preferably, the composition of the invention for combinatorially treating Alzheimer's disease (AD) or a related disorder in a subject in need thereof comprises at least one of the following drug combinations for combined, separate or sequential administration:

phenformin and zonisamide,
phenformin and methyclothiazide,
phenformin and acamprosate,
phenformin and sulfisoxazole,
baclofen and aminocaproic acid,
baclofen and levosimendan,
baclofen and terbinafine,
baclofen and risedronate,
baclofen and sulfisoxazole,
baclofen and zonisamide,
baclofen and methyclothiazide,
baclofen and sulfisoxazole,
baclofen and leflunomide,
aminocaproic acid and sulfisoxazole,
aminocaproic acid and terbinafine,
aminocaproic acid and levosimendan,
levosimendan and sulfisoxazole,
levosimendan and terbinafine,
zonisamide and dyphylline,
methyclothiazide and dyphylline,
zonisamide and prilocaine,
methyclothiazide and prilocaine,
zonisamide and sulfisoxazole,
phenformin and clopidogrel,
acamprosate and cinacalcet,
sulfisoxazole and cinacalcet,
terbinafine and argatroban,
terbinafine and cefmenoxime,
baclofen and clopidogrel,
terbinafine and clopidogrel,
risedronate and clopidogrel,
zonisamide and cinnarizine,
sulodexide and sulfisoxazole,
torasemide and aminocaproic acid,
torasemide and levosimendan,
carbamazine and acamprosate,
acamprosate and erythrityl tetranitrate,
sulfisoxazole and erythrityl tetranitrate,
mitiglinide or levosimendan and erythrityl tetranitrate,
mitiglinide or levosimendan and zonisamide,
mitiglinide or levosimendan and terbinafine,
mitiglinide or levosimendan and risedronate,
mitiglinide or levosimendan and methyclothiazide,
methyclothiazide or zonisamide and sulfisoxazole,
terbinafine or risedronate and sulfisoxazole,
terbinafine or risedronate and mepacrine,
terbinafine or risedronate and acamprosate,
terbinafine or risedronate and rifabutin,
tadalafil or enprofylline or oxtriphylline and phenformin,
zonisamide or methyclothiazide and argatroban or cefmenoxime,
risedronate and argatroban or cefmenoxime,
zonisamide or methyclothiazide and cinnarizine or benidipine or paramethadione or amlodipine,
acamprosate and cinnarizine or benidipine or paramethadione or amlodipine,
zonisamide or methyclothiazide and ciclopirox,
sulfisoxazole and amobarbital,
zonisamide or methyclothiazide and amobarbital,
sulfisoxazole and cefotetan,
zonisamide or methyclothiazide and cefotetan, or
zonisamide or methyclothiazide and erythrityl tetranitrate.

Specific examples of preferred compositions of the invention comprise one of the following drug combinations for combined, separate or sequential administration:

baclofen and aminocaproic acid,
baclofen and levosimendan,
aminocaproic acid and sulfisoxazole,
aminocaproic acid and terbinafine,
aminocaproic acid and levosimendan,
levosimendan and sulfisoxazole,
levosimendan and terbinafine,
eplerenone and levosimendan,
eplerenone and sulfisoxazole,
eplerenone and fenoldopam,
sulodexide and levosimendan,
sulodexide and sulfisoxazole,
sulodexide and sulfisoxazole,
torasemide and aminocaproic acid,
torasemide and levosimendan,
carbamazine and acamprosate,
sulodexide and fenoldopam, or
eplerenone and sulodexide.

As illustrated in the experimental section, compositions comprising at least aminocaproic acid or levosimendan provide substantial therapeutic and biological effects to improve Alzheimer's disease in human subjects. These compositions efficiently prevent the toxic effects of amyloid b protein or peptide on human cells and represent novel and potent methods for treating such disorder.

In another preferred embodiment, the compositions according to the invention comprise a combination of at least three compounds, or salts or prodrugs or derivatives of any purity or sustained release formulations thereof, for simultaneous, separate or sequential administration for combinatorial treatment of Alzheimer's disease (AD) or a related disorder in a subject in need thereof.

Therapeutic approaches according to the invention may use drugs alone or drug combinations, in conjunction with any other therapy targeting the same pathway or having distinct modes of action.

In particular embodiments, the compositions of the present invention might further comprise a drug or drugs, which already exist or could be developed, that bind to or modulate the activity of a protein encoded by a gene selected from ABAT, ABCA1, ABI1, ABL1, ACAT, ACC2, ACCN1, ADAMTS12, ADCY2, ADIPOQ, ADIPOR1/R2, ADORA1/2A/2B, ADRA1A/2, ADRB1/2, AGPAT5, AIP4, AKAP2, AKR1C2, AKT, ALDH2, ALOX12, ALOX5, ANG2, ANK1, ANKRA, ANXA1, APBA1, APBA2BP, APOA1, APOER2, ARHGAP17, ARHGAP26, ATG5/7/12, ATM, ATP10A, ATP1A1, ATP2A3, ATP2B1, ATP6V1C1, ATR, AUH, BACE1, BAD, BAI3, BASSOON, BAX, BCAR1, BCL2, BDNF, BECLIN1, BIN1, BK channels (KCNMA1, KCNMB1), BMP3A, BRCA1, CA10, CACNA1C/2D3/2D4, CADPS2, CALM1-5 (calmodulin), CAMK1D, CAMKK2, CASK, CASR, CAST, CBL, CD36, CD44, CDC2, CDC42, CDC42BPB, CDC42EP3, CDH1/2/13, CDK5, CDKN1A, CHAT, CHK1, CHRM1-5, CHRNA1-7/9/10, CIT (citron), CK1, CNGB3, CNTFR, COL4A2, CPT, CRAM, CREB, CRMP, CSH1, CTNNA2, CTNNB1, CTTN (cortactin), CUBN, CULLIN1, CYP7B1, CYSLTR1/R2, DAB1, DCC, DEPDC2, DGKB/H/Z, DHCR7, DHFR, DLG2/4, DNAJB9, DOCK3, DRD2/5, DYN1/3, EDG1-8, EDN1/2, EDNRA/B, EFNA1/2/4/5/7 (ephrin A), EFNB1/2/3 (ephrin B), EHHADH, ELAVL2, ENPP2 (autotaxin), ENPP6, EPHA3, EPHBR1/2/3/4/6, ERBB2/4, ERK1/2, ESRRG, ETFA, EZR, F2, F2R, FAS, FDPS, FES, FGF1/2, FKBP12/12.6, FLNA, FLT1 (VEGFR1), FLT4, FOXO1/3A, FRAP (MTOR), FTO, FYN, FZ2, GABBR1/2, GABRA2/G2, GADD45, GATT, GATA3, GH1, GIPC1/2, GLRA1, GLUD1, GNA12/13, GNPTAB, GPC5, GPHN (gephyrin), GRIA2/3, GRID1/2, GRIK1/2, GRIN2B/3A, GRIP1/2, GRK2/5, GRM3/5/6/7/8, GRP170, GSK3B, HAPLN1, HAS1-3, HCRTR2, HIF1A, HIPK2, HK2, HMOX1, HOMER1/2/3, HSD11B1, HSP90B1, HSPA5, HTR1A/1B/1D, HYAL1/2/3, IDE, IL20RA/B, IL6ST, IL8, IMPDH1/2, INS, INSR, IRF1, ITB1, ITGA1/6, ITGB1, ITPR1, JNK1, KALRN (kalirin), KCNA2/D2, KCNH2, KCNIP1/2, KCNJ11, KCNJ12, KCNJ3, KCNMA1, KCNMB1-4, KDR (VEGFR2), KTN1, KYNU, LAMA1, LDLR, LEP (LEPTIN), LEPR, LIFR, LIN7A/B/C (VELI1/2/3), LIPL2, LKB1, LRP1, LRP2 (megalin), LTBP2, LYN, MAD1L1, MAML3, MAOA/B, MAT2B, MCC1, MDM1, ME1, MET, MGST2, MINT1, MLLT4 (afadin), MMP2, MMP9, MOESIN, MTR, MUC1, MUNC13/18A, MYO6, MYOL, NADPH oxidase, NAV1, NBEA, NCAM1, NCK1/2, NEDD9, NF2 (merlin), NFKB1, NFKBIB, NGEF (ephexin), NGF, NGFR, NHERF, NIL16, NLGN1, NOC2, NOS1/2A/3, NOTCH1/2/3, NPC1/2, NPIST, NR1I2, NR3C1, NR3C2, NRG1/3, NRP1/2, NRX3, NTF3/5, NTN1 (netrin 1), NTRK2 (TRKB), NWASP, OPCML, OPRK1, OPRM, OPRS1, OSBPL3/10, P2RY1, P2RY 12, PAELR, PAI1/2, PAK1/6/7, PALLD, PAP1, PARK2, PC, PCAF, PCTP, PDE11A, PDE1A, PDE3A/3B, PDE4A/4B/4D, PDE5A, PDE6D, PDGFA/B, PDGFRA/B, PI3K, PIAS1, PICALM, PICK1, PIK3C3, PIP5K, PITPNC1, PKCA, PKCD, PLA1A/2, PLAT, PLAU, PLCB1, PLD1/2, PLEXA1, PLG, PLN, PLXDC2, PML, POP2, PPARA, PPARD, PPARG, PPARGC1B, PPFIBP1, PPP1CA, PPP3CA (calcineurin), PRDX5/6, PRKAA (AMPK), PRKACA, PRKG1, PRL, PTGER1, PTGFR, PTGS2, PTN, PTP1B, PTPN11, PTPRF, PTPRG, PTPRM, PVRL1, PXN (paxillin), PYK2, RAB3B, RAC1, RACK1, RAPT, RASGRF2, RBPJ, RDX (radixin), RELN, RGNEF, RHEB, RHOA, RHOG, RIM2, RIMS1/2, ROBO2, ROCK1/2, ROR2, RPH3A (rabphilin), RPH3AL, RPS6KA1, RPS6KB2, RTN1, RXR/RAR, RYR3, SACM1L, SAPAP, SAPK3, SCARB1, SCHIP1, SCN1A/1B, SCNN1D/1G, SEC24D, SEMA3A/3C/3E/4C, SGPP2, SH3BP5, SIAH1A, SILL SLC12A1/2/5, SLC1A2, SLC25A21, SLC6A1/A18, SLC8A1/A2/A3, SLC9A1, SLIT1, SLN, SMAD3/4, SNAP25, SNCA, SNCAIP, SORBS2, SORCS2, SPLA2, SPOCK1, SPP1 (osteopontin), SRC, SRD5A1, SREBF1/F2, SRGAP3, STAT3, STX1A/2 (syntaxins), STXBP6, SUM1, SV2C, SYN1, SYNJ1/2 (synaptojanin), SYT12, SYTL4 (granuphilin), TACE, TACR1, TBR1, TBXA2R, TGFBR1/R2/R3, THBS1/2, THEM2, THRA/B, TIAM1, TIMP2, TLL2, TOP2A, TP53, TP63, TRIO, TRPC3/4/5, TSC1/2, TSPO, UBE2A, ULK4, UNC13C, UNC5C, VAMP2/5, VCL (VINCULIN), VDAC1, VEGFA/C, VEGFR1, VMAT, VPS15, WASPIP, WAVE, WNT1A/5A, WWOX, XANTHINE OXIDASE, YAP and YES1.

The sequences of all of the above listed genes and proteins are available from gene libraries and can be isolated by techniques known in the art. The activity of these genes and proteins can also be assessed by techniques known in the art.

The invention also describes these supplementary drugs that can be used to modulate target genes and proteins. We have identified particular drugs which, either alone, or in combination(s), modulate the pathways described above, and may be used to treat Alzheimer's disease or related disorders.

In a preferred embodiment, the compositions of the invention may further comprise at least one drug selected from an inhibitor ABAT, (preferably, vigabatrin), and/or an inhibitor ABL1 (preferably imatinib), and/or an inhibitor of ACAT (preferably, hesperetin), and/or a modulator of ADCY2 (preferably, vidarabine), and/or a modulator of adenosine ADORA1/2A/3 receptors (preferably selected from clofarabine and defibrotide), and/or a modulator of adrenergic ADRA receptors (preferably selected from propericiazine, methotrimeprazine, mephentermine and dipivefrin), and/or a modulator of adrenergic ADRB receptors (preferably selected from guanethidine, bethanidine, bitolterol and procaterol), and/or an inhibitor of ALOX5/12 (preferably selected from diethylcarbamazine and masoprocol), and/or an inhibitor of ATP1A1 (preferably, deslanoside and omeprazole), and/or an activator of autophagy (preferably, trehalose), and/or an inhibitor of CA10 (preferably, methazolamide), and/or a modulator of calcification (preferably selected from foscarnet, gallium nitrate, calcifediol, calcitonin, calcitriol, clodronic acid, dihydrotachysterol, elcatonin, etidronic acid, ipriflavone and teriparatide acetate), and/or a modulator of CALM1 (calmodulin) (preferably, aprindine), and/or a modulator of CD44 (preferably selected from eflornithine and benzbromarone), and/or a chemical chaperon (preferably selected from arabitol and mannitol), and/or a modulator of muscarinic CHRM receptors (preferably selected from cyclopentolate, oxyphencyclimine, trospium and isoflurophate), and/or an antagonist of nicotinic acetylcholine CHRNA receptors, which is not able to cross the blood-brain barrier (preferably selected from pancuronium, pipecuronium, rapacuronium, rocuronium, succinylcholine, vecuronium, atracurium, cisatracurium, doxacurium, mecamylamine, metocurine, mivacurium and neomycin), and/or an inhibitor of CNGB3 (preferably, amiloride), and/or a modulator of CYSLTR1/2, PTGER1, PTGFR and TBXA2R eicosanoid receptors (preferably selected from travoprost, montelukast, cinalukast, amlexanox, carboprost tromethamine, bimatoprost and ridogrel), and/or an inhibitor of DHFR (preferably, pyrimethamine and triamterene), and/or a modulator of dopamine DRD2 receptor (preferably selected from dihydroergotamine and cabergoline), and/or an agonist of dopamine receptor DRD5 (preferably, fenoldopam), and/or an inhibitor of EDNRA (preferably selected from sulfamethoxazole and gentamicin), and/or a modulator of ENPP2 (autotaxin) (preferably, L-histidine), and/or an inhibitor of ERBB2 (preferably, lapatinib), and/or a modulator of F2 thrombin (preferably selected from sulodexide, ximelagatran, warfarin, phenprocoumon, enoxaparin, ardeparin, fondaparinux, latamoxef, bacitracin, ticlopidine and erdosteine), and/or an inhibitor of FDPS (preferably, alendronate), and/or a modulator of GABRA2 (preferably selected from phenobarbital, methohexital, cefotiam, clomethiazole, thiopental, lubiprostone and aztreonam), and/or an antagonist of GRIK1 (preferably, topiramate), and/or a modulator of GSK3B activity (preferably selected from albuterol and metaraminol), and/or a modulator of HIF1A signalling (preferably selected from meloxicam, topotecan, deferoxamine, usnic acid, hydralazine, deferiprone, dibenzoylmethane, avobenzone, dinoprostone, epoprostenol, 2-oxoglutarate and mimosine), and/or an inhibitor of HK2 (hexokinase II) (preferably selected from quinine, gabexate, bifonazole and clotrimazole), and/or a modulator of HMOX1 (preferably selected from auranofin, hematin/hemin and heme arginate), and/or a modulator of HTR1B/1D receptors (preferably selected from ergotamine and eletriptan), and/or an inhibitor of IMPDH1 and IMPDH2 (preferably, thioguanine), and/or a modulator of integrins ITGA/B (preferably, rabeprazole), and/or an inhibitor of KCND2 potassium channel (preferably, lidocaine), and/or an inhibitor of KCNH2 potassium channel (preferably, ibutilide), and/or a modulator of KCNMA1 (preferably selected from cromoglicate, ethinamate, ketoconazole, chlorzoxazone, unoprostone, hesperitin, bendroflumethiazide, benzthiazide, chlorothiazide, cyclothiazide, diazoxide, hydroflumethiazide, quinethazone and trichlormethiazide), and/or a modulator of MGST2 (preferably, balsalazide), and/or a modulator of MMP2 and MMP9 (preferably, candoxatril), and/or a modulator of mitochondrial permeability transition pore formation (preferably selected from carbenoxolone and ciprofloxacin), and/or an inhibitor of MTOR (preferably, rapamycin), and/or a modulator of NOS1/2A/3 (preferably selected from propylthiouracil, thiethylperazine and ketotifen), and/or a modulator of NR3C1 receptor signalling (preferably selected from metyrapone and mometasone), and/or a modulator of NR3C2 receptor (preferably selected from eplerenone and fludrocortisone), and/or an inhibitor of NRP2 (preferably, pegaptanib), and/or a modulator of OPCML (preferably, alfentanil), and/or a modulator of OPRK1 and OPRS1 (preferably selected from buprenorphine and pentazocine), and/or OPRM (preferably, levallorphan), and/or a modulator of oxidative phosphorylation (preferably selected from almitrine, erythromycin, kanamycin and cerulenin), and/or an inhibitor of P2RY1 and/or P2RY12 receptors (preferably, tirofiban), and/or an inhibitor of PDE11A, PDE4A and PDE5A phosphodiesterases (preferably selected from mesembrine, milrinone and anagrelide), and/or an inhibitor of PDE3A/3B and PDE4A/4B phosphodiesterases and an activator of BK channels (preferably, cilostazol), and/or a modulator of PDGFRA/B receptors (preferably selected from becaplermin, streptomycin, delphinidin, cyanidin and fumagillin), and/or a modulator of PLA2 (preferably selected from niflumic acid, hydrocortamate and netilmicin), and/or a modulator of PLAT (preferably, sodium phenylbutyrate), and/or a modulator of PLD2 (preferably, ambrisentan), and/or an inhibitor of PLG (preferably, aminocaproic acid), and/or a modulator of PPARD (preferably, icosapent), and/or a modulator of PPARG (preferably, phenylbutyrate), and/or a modulator of PRKG1 (preferably selected from nitroprusside, nitroglycerin and paricalcitol), and/or an inhibitor of PTP1B (preferably, tiludronate), and/or a modulator of RHOA/RAC (preferably selected from chlorthalidone, hydrochlorothiazide, clomocycline, lymecycline, natamycin, amphotericin B, cefalexin, cephaloridine, cefuroxime, dicloxacillin), and/or a modulator of RXR/RAR (preferably, tazarotene), and/or an antagonist of SCN1A/B sodium channels (preferably, fosphenytoin), and/or an inhibitor of SLC12A1 (preferably, bumetanide), and/or an inhibitor of SLC6A1 (preferably, tiagabine), and/or a modulator of SLC9A1 (preferably, buclizine), and/or an inhibitor of SRD5A1 (preferably, dutasteride), and/or an antagonist of TACR1 (preferably selected from aprepitant and vapreotide), and/or a modulator of TGFB signalling (preferably, aliskiren), and/or a modulator of THRA/B (preferably selected from liothyronine), and/or an inhibitor of TOP2A (preferably, lucanthone), and/or a modulator of TSPO (preferably selected from flunitrazepam and temazepam), and/or a modulator of VDAC1 (preferably, dihydroxyaluminium), and/or an inhibitor of VEGFR1 (preferably, sunitinib), and/or a modulator of vitamin K metabolism (preferably selected cefmetazole, cefamandole and cefoperazone), and/or an inhibitor of VMAT (preferably selected from tetrabenazine, deserpidine and nitisinone), and/or an inhibitor of voltage gated calcium channels (CACNA) (preferably selected from lercanidipine, pregabalin, mibefradil, aranidipine, bamidipine, bencyclane, bepridil, clentiazem, efonidipine, elgodipine, etafenone, fendiline, flunarizine, gallopamil, isradipine, lacidipine, lidoflazine, lomerizine, manidipine, nicardipine, nilvadipine, nimodipine, nisoldipine, nitrendipine, perhexiline, prenylamine, semotiadil and terodiline), and/or an inhibitor of YES1, SRC and EPHA3 (preferably, dasatinib).

Other therapies used in conjunction with drug(s) or drug(s) combination(s) according to the present invention, may comprise one or more drug(s) that ameliorate symptoms of Alzheimer's disease or drug(s) that could be used for palliative treatment of Alzheimer's disease. Preferably, said one or more drug(s) is/are selected from 3APS, AAB-001, ABT-089, ABT-126, AC-3933, ACC-001, Acetaminophen, AFFITOPE AD01, AFFITOPE AD02, alpha-lipoic acid, alpha-tocopherol, AN1792, anti-Abeta, AQW051, Aripiprazole, Atomoxetine, Atorvastatin, AVE1625, AVP-923, AZD0328, AZD3480, Bapineuzumab, BAY94-9172 (ZK 6013443), Bifeprunox, Bioperine, BMS-708163, BRL-049653, Bryostatin, CAD106, Celecoxib, CERE-110, Cerebrolysin, CHF 5074, Choline, Circadin, Citalopram, Coenzyme Q, Copper, CTS21166, Curcumin, CX516 (Ampalex), CX717, Cyclophosphamate, DCB-AD1, Dextroamphetamine, DHA (Docosahexaenoic Acid), Digoxin, Dimebon (Latrepirdine), Divalproex, DMXB-A, Donepezil, Doxycycline, Egb 761, EHT 0202 tazolate, ELND005 (scyllo-inositol), EPAX 1050TG, Ergoloid mesylate, Epigallocatechin-Gallate, Escitalopram, Estradiol, Estrogen, Etanercept, EVP-6124, EVT101, Exelon, Fish oil, FK962, florpiramine F 18, Folate+Vitamin B6+Vitamin B21, Gabapentin, Galantamine, Gemfibrozil, *Ginkgo biloba* extracts (for example EGb 761 or CP401), improved extracts of *Ginkgo biloba* (for example enriched in active ingredients or lessened in contaminants) or drugs containing *Ginkgo biloba* extracts (for example Tanakan or Ginkor Fort), Glucose, L-Glutamic Acid, GSI 136, GSI-953, GSK239512, GSK933776A, Haloperidol, HF0220, Huperzine A, hydrocodone/APAP, Ibuprofen, IFN-alpha2A, Indomethacin, Insulin, Intravenous Immunoglobulin, Ketasyn, Lecozotan, Leuprolide, Levodopa, Lipoic Acid, Lithium, Lorazepam, Lovostatin, Lutein, LY2062430 (solanezumab), LY2811376, LY450139, LY451395, MABT5102A, Malate, Masitinib (AB1010), Medroxyprogesterone, Melatonin, MEM 1003, MEM 3454, Memantine, Methylene blue, Methylphenidate, Mifepristone, MK0249, MK0677, MK0952, MK0952, MK3328, Modafinil, MPC-7869, NADH, Naproxen, Nefiracetam, Neptune Krill Oil, Neramexane, NIC5-15, Nicoderm Patch, Nicotinamide (vitamin B3), Novasoy, NP031112, NS 2330, NSA-789, NSAIDs, Olanzapine, omega-3 polyunsaturated fatty acids (EPA+DHA), ONO-2506P0, Oxybate, *Panax Ginseng*, PAZ-417, PBT2, Perphenazine, PF-04360365, PF-04447943, PF-04494700, Phenserine, Phosphatidylserine, Pitavastatin, Posiphen, PPI-1019 (APAN), Pravastatin, Prazosin, Prednisone, Progesterone, PRX-03140, PYM50028, Quetiapine, R1450, Raloxifene, Ramipril, Rasagiline, Razadyne, resveratrol, rifampicin, risperidone, Rivastigmine, RN1219, RO5313534, Rofecoxib, Rosiglitazone, *Salvia officinalis* (sage), SAM-315, SAM-531, SAM-760, SB-742457, Selenium, Sertraline, SGS-742, Simvastatin, SK—PC-B70M, Solanezumab, SR57667B, SRA-333, SRA-444, SSR180711C, ST101, T-817MA, Tacrine, Tarenflurbil, Testosterone, Tramiprosate (3APS), Trazodone, TRx0014 (methylthioninium chloride), Tryptophan, V950, Valproate, Varenicline, Vitamin C, Vitamin E, VP4896, Xaliproden, Zeaxanthin, Zolpidem, and ZT-1 (DEBIO-9902 SR).

The invention also relates to a method of treating Alzheimer's disease or a related disorder, the method comprising simultaneously, separately or sequentially administering to a subject in need thereof a drug combination as disclosed above.

A further object of this invention is a method of treating Alzheimer's disease or a related disorder, the method comprising simultaneously, separately or sequentially administering to a subject in need thereof a drug combination that modulates synapse function and/or a drug that modulates angiogenesis and/or a drug that modulates cell stress response.

A further object of the invention resides in a method of selecting a drug for combinatorial treating Alzheimer's disease or a related disorder, the method comprising a step of testing a candidate drug for activity on synapse function and/or angiogenesis and/or cellular stress response and selecting a candidate drug that ameliorates synapse function, attenuates angiogenic dysregulation and modulates cellular stress response.

In another embodiment, the invention relates to a method of selecting a composition for treating Alzheimer's disease or a related disorder, the method comprising preparing a combination of a drug that modulates synapse function and/or a drug that attenuates angiogenic dysregulation and/or a drug that modulates cell stress response, for simultaneous, separate or sequential administration to a subject in need thereof.

In another preferred embodiment, the invention relates to a method of treating Alzheimer's disease or a related disorder, the method comprising simultaneously, separately or sequentially administering to a subject in need thereof a drug that modulates synapse function and/or a drug that modulates angiogenesis and/or a drug that modulates cell stress response.

The composition of the invention may be administered repeatedly to the subject.

The compositions of the invention typically comprise one or several pharmaceutically acceptable carriers or excipients. The duration of the therapy depends on the stage of the disease being treated, the combination used, the age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recover from any as yet unforeseen side-effects. The drugs may also be formulated together such that one administration delivers all drugs.

The administration of each drug of the combination may be by any suitable means that results in a concentration of the drug that, combined with the other component, is able to correct the functioning of pathways implicated in AD.

While it is possible for the active ingredients of the combination to be administered as the pure chemicals it is preferable to present them as a pharmaceutical composition, also referred to in this context as a pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number of dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help use the formulation most suitably for the treatment. Such measures make a patient pack specifically suitable for and adapted for use for treatment with the combination of the present invention.

The drug may be contained in any appropriate amount in any suitable carrier substance, and may be present in an amount of 1-99% by weight of the total weight of the composition. The composition may be provided in a dosage form that is suitable for the oral, parenteral (e.g., intravenous, intramuscular), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, micro crystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes (e.g., chemical degradation prior to the release of the active drug substance). The coating may be applied on the solid dosage form in a similar manner as that described in Encyclopedia of Pharmaceutical Technology.

Several drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in the form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), and poly(2-hydroxyethyl-L-glutamnine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type) and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The Emulsifying Agents May be Naturally Occurring Gums (e.g., Gum Acacia or Gum Tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulations or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help use the combination according to the invention.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

Administration can be one to several times daily for several days to several years, and may even be for the life of the patient. Chronic or at least periodically repeated long-term administration will be indicated in most cases.

Additionally, pharmacogenomic (the effect of genotype on the pharmacokinetic, pharmacodynamic or efficacy profile of a therapeutic) information about a particular patient may affect the dosage used.

Except when responding to especially impairing AD cases when higher dosages may be required, the preferred dosage of each drug in the combination usually lies within the range of doses not above those usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually no substantial effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably 1/10 to 1/100 of therapeutic doses. At such sub-optimal dosages, the compounds alone would be substantially inactive, while the combination(s) according to the invention are fully effective.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs for use in the invention are provided below:
Carbamazine, typically orally, between 30 µg and 400 mg per day, preferably less than 180 mg per day, even more preferably less than 100 mg per day, even more preferably less than 30 mg per day, even more preferably less than 5 mg per day, divided in one, two or three doses,
Acamprosate orally between 1 and 1000 mg per day, preferably less than 500 mg per day, even more preferably less than 200 mg per day, even more preferably less than 100 mg per day. In a more preferable embodiment, acamprosate orally from about 7 to 70 mg three times daily,
aminocaproic acid from about 0.05 to 15 g per day,
levodimendan from 0.05 to 4 mg per day,
amlodipine orally from about 0.05 to 1 mg per day,
clopidogrel orally from about 0.75 to 7.5 mg per day,
tadalafil orally from about 0.05 to 0.5 mg per day,
cilostazol orally from about 1 to 10 mg per day,
terbinafine orally from about 2.5 to 25 mg once or twice daily,
leflunomide orally from about 0.25 to 2.5 mg per day,
cinacalcet orally from about 0.3 to 3 mg per day,
methimazole orally from about 0.05 to 1.5 mg per day,
mepacrine orally from about 3 to 30 mg per day,
phenformin orally from about 0.5 to 5 mg per day,
baclofen orally from about 0.4 to 8 mg per day administered in two or three divided doses,
rifabutin orally from about 6 to 60 mg per day,
amobarbital orally from about 0.06 to 15 mg per day,
cefotetan orally from about 0.01 to 0.4 mg per day,
dyphylline orally from about 6 to 60 mg per day in two or three divided doses,
methyclothiazide orally from about 0.025 to 1 mg per day,
risedronate orally from about 0.05 to 3 mg per day,
etomidate orally from about 0.6 to 6 mg per day,
torasemide orally from about 0.05 to 4 mg per day, and
zonisamide orally from about 1 to 40 mg per day.

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

I. the Compounds and Combinations Thereof Prevent Toxicity of $A\beta_{25-35}$ Peptide In this first series of experiments, candidate compounds have been tested for their ability to prevent or reduce the toxic effects of $A\beta_{25-35}$ peptide. The drugs are first tested individually, followed by assays of their combinatorial action. The effect is determined on various cell types, to further illustrate the activity of the compounds.

In AD, the APP protein forms aggregates of insoluble β-pleated sheets of fibrillar Abeta protein (amyloid). The conformational change from soluble to fibrillar forms seems to be a spontaneous event that is increased with higher concentrations of Abeta, so any production of larger amounts of Abeta than normal (or production of the larger, less soluble forms of Abeta) will tend to increase plaque formation. Once the Abeta plaque has started to form, other molecules can interact with the nascent plaque to produce eventually the mature plaque with its associated areas of neuronal cell death. Considering this, we have given priority to testing the effects of the drugs on the viability of the cells exposed to the amyloid 0 protein.

I.1 Protection Against the Toxicity of $A\beta_{25-35}$ Peptide on Cortical Neurons Cell culture Primary rat cortical neurons are cultured as described by Singer et al., 1999. Briefly pregnant female rats of 15 days gestation are killed by cervical dislocation (Rats Wistar; Janvier) and the foetuses removed from the uterus. The cortexes are removed and placed in ice-cold medium of Leibovitz (L15; Invitrogen) containing 1% of Penicillin-Streptomycin (PS; Invitrogen) and 1% of bovine serum albumin (BSA; Sigma). Cortexes are dissociated by trypsinisation for 20 min at 37° C. (Trypsin EDTA 1×; Invitrogen) diluted in PBS without calcium and magnesium. The reaction is stopped by the addition of Dulbecco's modified Eagle's medium (DMEM; Invitrogen) containing DNAase I grade II (0.1 mg/ml; Roche Diagnostics) and 10% of foetal calf serum (FCS; Invitrogen). Cells are then mechanically dissociated by 3 passages through a 10 ml pipette. Cells are then centrifuged at 180×g for 10 min at 10° C. The supernatant is discarded and the cells of pellet are re-suspended in a defined culture medium consisting of Neurobasal (Invitrogen) supplemented with B27 (2%; Invitrogen), L-glutamine (0.2 mM; Invitrogen), 1% of PS solution and 10 ng/ml of brain-derived neurotrophic factor (BDNF, Pan Biotech). Viable cells are counted in a Neubauer cytometer using the trypan blue exclusion test. Cells are seeded at a density of 30,000 cells/well in 96-well plates (wells are pre-coated with poly-L-lysine (10 µg/ml; Sigma)) and are cultured at 37° C. in a humidified air (95%)/CO2 (5%) atmosphere.

After 6 days of culture, cells are incubated with drugs (5 concentrations). After 1 hour, cells are intoxicated by 20 µM of beta-amyloid (25-35; Sigma) in defined medium without BDNF but together with drugs. Cortical neurons are intoxicated for 2 days. Two independent cultures are performed per condition, 6 wells per condition.

Neurites Length Quantification

Cells are fixed with a cool solution of ethanol (95%) and acetic acid (5%) for 10 min. After permeabilization with 0.1% of saponin, cells are blocked for 2 h with PBS containing 10% goat serum. Cells are then incubated with monoclonal antibody directed against the microtubule associated protein 2 (MAP-2; Sigma). This antibody specifically reveals cell bodies and neurites. The secondary antibody used is an Alexa Fluor 488 goat anti-mouse IgG (Molecular probe). Nuclei of neurons are revealed by a fluorescent dye (Hoechst solution, SIGMA). Twenty pictures are taken per well, using InCell Analyzer™ 1000 (GE Healthcare) at magnification 20×. All images are taken in the same conditions. Neurite length is quantified using Developer software (GE Healthcare).

Results

Results presented in FIG. 1 are extracted from two independent cultures, 6 wells per condition. All values are expressed as mean±s.e.mean. A bilateral Student's t test analysis is performed on raw data. Results are expressed in percentage of neurite length, compared to the control (vehicle).

Drugs were incubated with rat primary cortical neurons one hour before Abeta$_{25-35}$ 20 µM intoxication that lasts 2 days (36).

Figure 2:
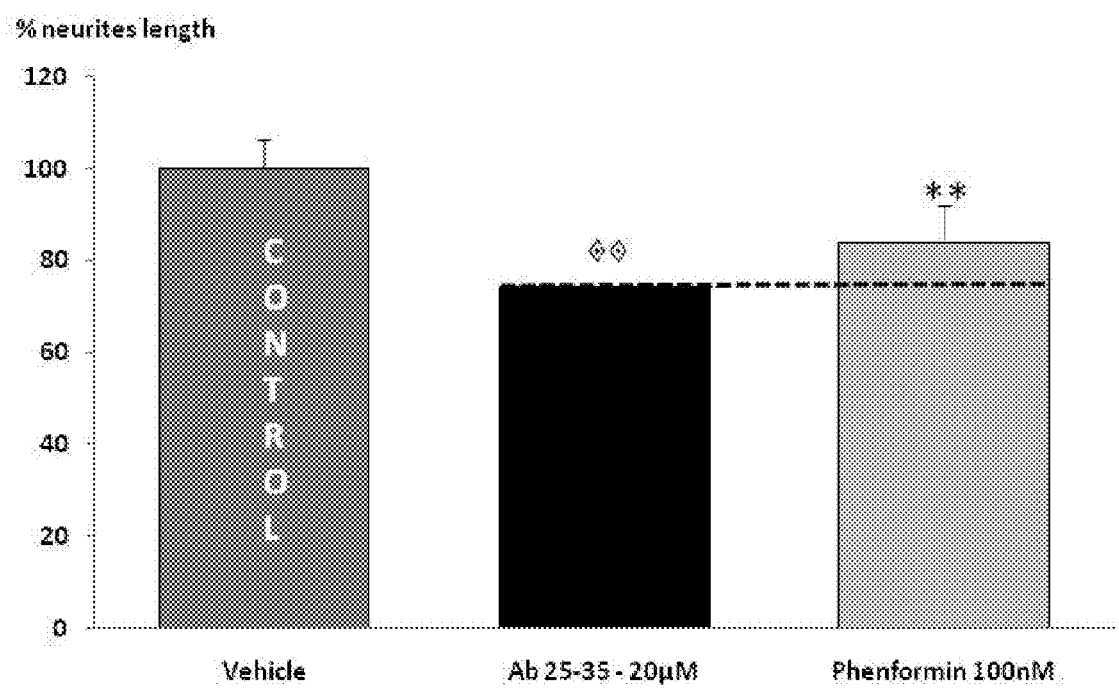
FIG. 2: Effect of Phenformin on neurite outgrowth in beta-amyloid intoxicated rat primary cortical neuron culture. ◊◊: $p<0.01$: significantly different from vehicle.**: $p<0.001$: significantly different from $A\beta_{25-35}$. Bilateral Student's t test. $A\beta_{25-35}$ 20 µM produces significant intoxication, above 25%, compared to vehicle-treated neurons. This intoxication is significantly prevented by Phenformin.

Two days after this incubation the network of neurite length was quantified, reflecting axonal cell growth. The results show that the tested drugs clearly exert a neuroprotective effect against Abeta$_{25-35}$ intoxication (FIG. 1 and FIG. 2).

I.2. Protection Against the Toxicity of Aβ$_{25-35}$ Peptide on Endothelial Cerebral Cells Cell Culture Primo culture of rat endothelial cerebral cells (Vect-Horus SAS, Marseille) is cultivated on passage 0. At confluence, endothelial cells are dissociated with trypsin EDTA (Pan Biotech Ref: P10-023100). Cells are seeded at a density of 25,000 cells/well in 96-well plates (wells are coated with 30 µl of type I rat collagen at 1.5 mg/ml, Vect-Horus SAS, Marseille) and are cultured in MCBD 131 medium (M-131-500, Invitrogen) supplemented with 1% of microvascular growth supplement (MVGS, S-005-25, Invitrogen). Cells are cultured at 37° C. in a humidified air (95%)/CO2(5%) atmosphere. Half of the medium is changed every other day with fresh medium.

After 4 days, drugs are added to the cell culture medium, at different concentrations, solved in DMSO 0.1% or water. A 1 hour pre-incubation is performed, in a culture medium containing Dulbecco's modified Eagle's medium (DMEM, Pan Biotech Ref: P04-03600), supplemented with 2% of fetal bovine serum (FBS; Invitrogen ref: 16000-036), 1% of L-glutamine (Pan Biotech ref: P04-80100), 1% of Penicillin-Streptomycin (PS; Pan Biotech ref: P06-07100), 0.1 mg/ml of Heparin (Sigma), 10 ng/ml of epidermal growth factor (EGF, Invitrogen) and 10 ng/ml of vascular endothelial growth factor (VEGF, PHG0146, Invitrogen).

Cells are then intoxicated with 30 µM of β-amyloid (25-35; Sigma) together with drugs in the same culture medium. Cells are then intoxicated for 3 days.

Lactate Dehydrogenase (LDH) Activity Assay

For each culture, after 3 days of intoxication, the supernatant is collected and analyzed with the Cytotoxicity Detection Kit (LDH, Roche Applied Sciences). This colorimetric assay for the quantification of cell death is based on the measurement of lactate dehydrogenase (LDH) activity released from the cytosol of damaged cells into the supernatant. The optic density (DO) is assessed by spectrophotometer at 492 nm wavelength by a multiscan apparatus (Thermo, Ref Ascent).

Results

Figures 3, 4:
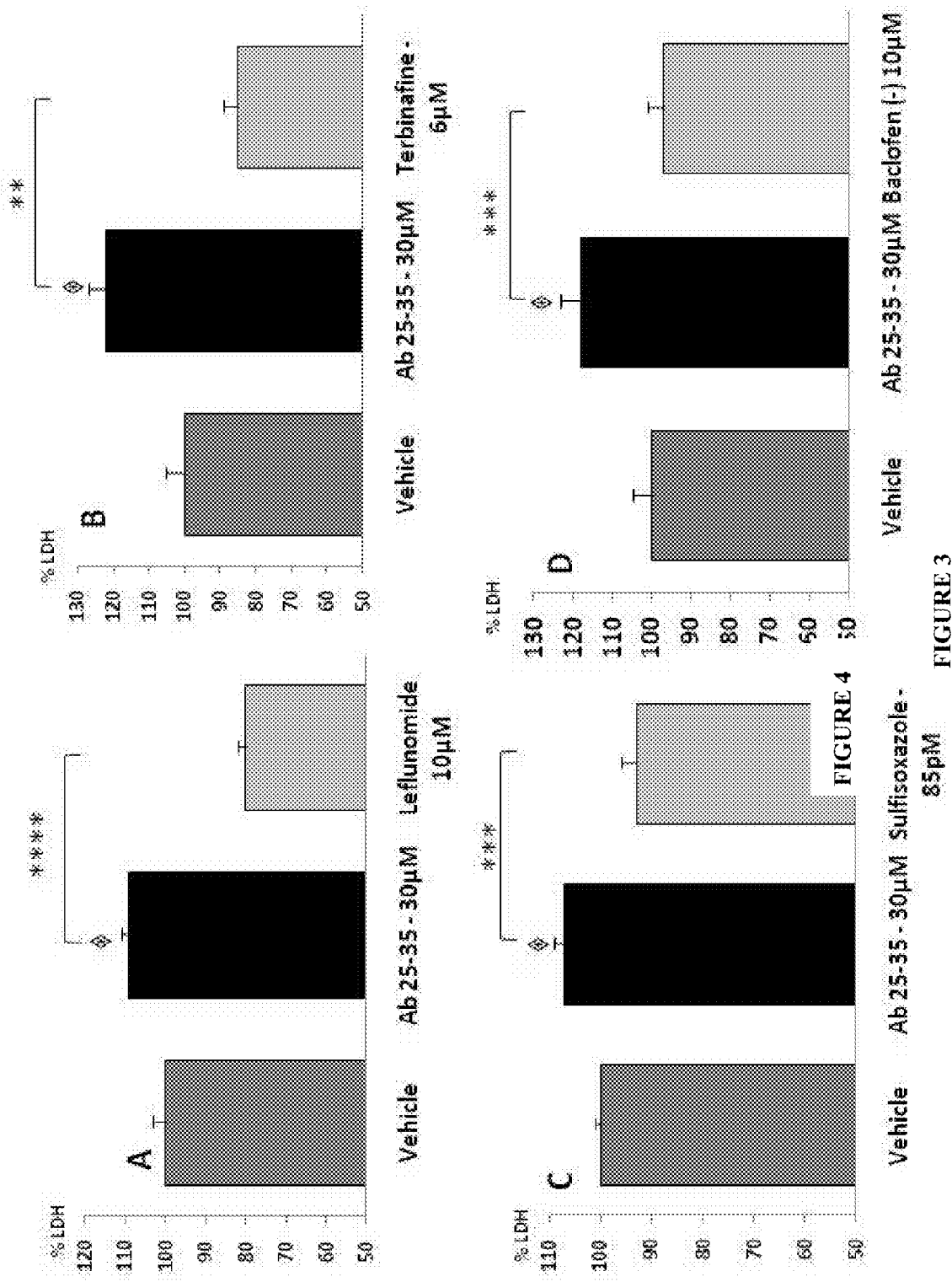
FIGS. 3A-3D: Protective effect of selected drugs against beta-amyloid peptide toxicity on LDH release from rat endothelial cerebral cells. ◊: $p<0.05$: significantly different from vehicle.:$p<0.01$; *:$p<0.0001$; ****:$p<0.00001$: significantly different from $A\beta_{25-35}$. Bilateral Student's t test. $A\beta_{25-35}$ 30 µM produces moderate but significant intoxication (FIG. 3A to D). This intoxication is significantly prevented by Leflunomide (FIG. 3A), Terbinafine (FIG. 3B), Sulfisoxazole (FIG. 3C) or Baclofen (-) (FIG. 3D). Furthermore, Leflunomide and Terbinafine not only prevent amyloid deleterious effects, but also decrease spontaneous cell death in the culture medium.
FIGS. 4A-4B: Effect of selected drugs on NGF-differentiated PC12 viability after beta-amyloid intoxicated intoxication. ◊◊◊◊: $p<0.00001$: significantly different from vehicle. :$p<0.01$; *:$p<0.0001$: significantly different from $A\beta_{25-35}$. Bilateral Student's t test. $A\beta_{25-35}$ 10 µM produces significant intoxication, above 25%, compared to vehicle-treated neurons (FIGS. 4A and 4B. This intoxication is significantly prevented by Prilocain (FIG. 4A) or Amlodipine (FIG. 4B).
Figure 4:
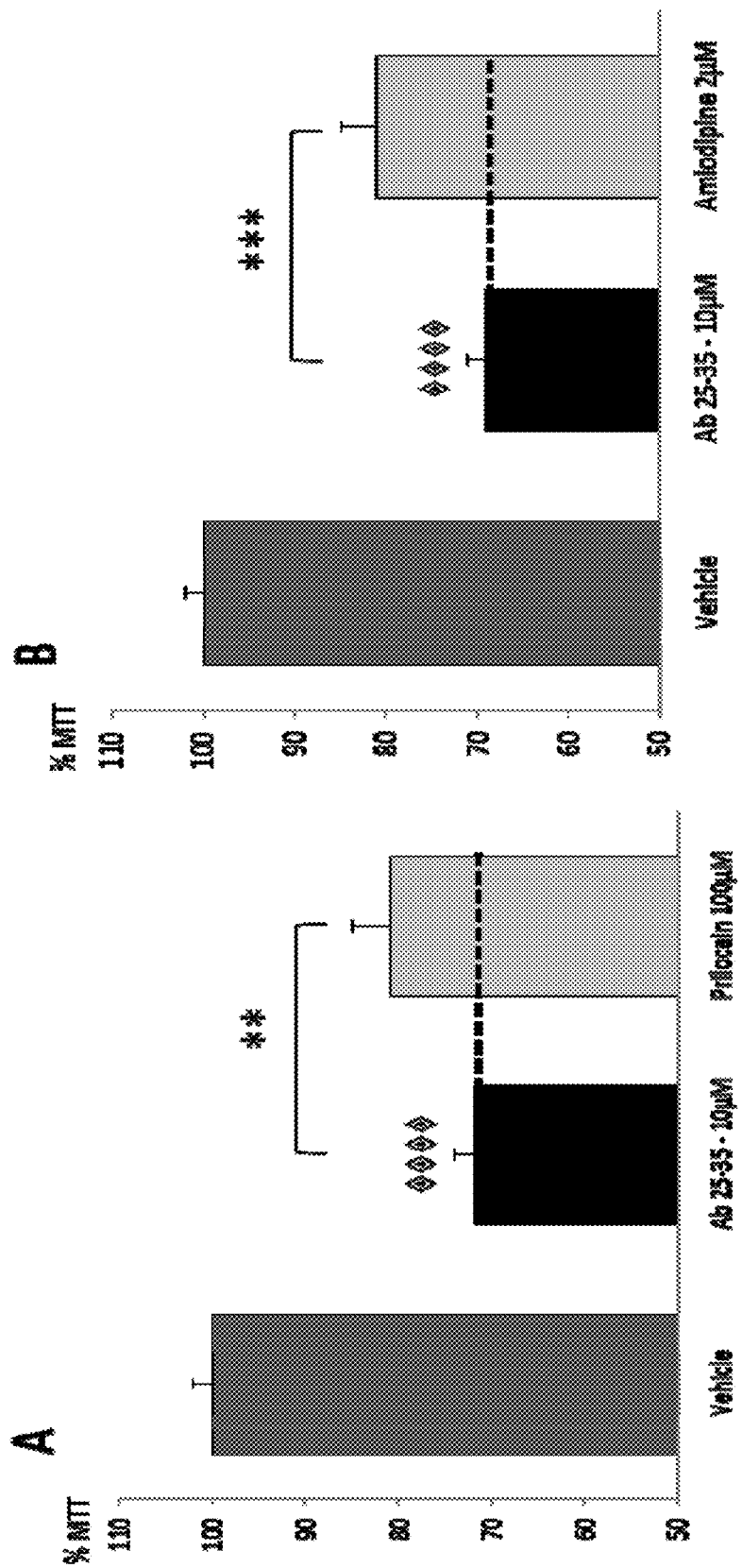

Results presented in FIG. 3 are extracted from two independent cultures, 6 wells per condition. All values are expressed as mean±s.e.m. A bilateral Student's t test analysis is performed on raw data. Results are expressed in percentage of cell viability, compared to the control (vehicle).

Drugs are incubated with rat primary cerebral endothelial cells for one hour before Aβ$_{25-35}$ 30 µM intoxication that lasts 3 days.

Three days after this incubation, LDH release in the culture medium is quantified, reflecting the level of cell death.

The results presented clearly show that the tested compounds exert a potent protective effect against this Aβ$_{25-35}$ intoxication (FIG. 3).

I.3. Protection Against the Toxicity of Aβ$_{25-35}$ Peptide on Pheochromocytoma Cells PC12 Cell Culture PC12 (Pheochromocytoma Rat, ATCC ref: CRL-1721) cells from ATCC (ATCC CRL-1721) were rapidly thawed in 37° C. water. The supernatant was immediately put in 9 ml of a PC12 proliferation medium containing Dulbecco's modified Eagle's medium DMEM-F12 (Pan Biotech ref: P04-41450) with 15% heat-inactivated horse serum (Invitrogen ref: 16050-130), 2.5% of fetal bovine serum (FBS; Invitrogen ref: 16000-036), 1% of Penicillin 10,000 U/ml and Streptomycin 10 mg/ml (PS; Pan Biotech ref: P06-07100) and 1% of L-glutamine 200 mM (Pan Biotech ref: P04-80100).

Cells were centrifuged (800 rounds/min, 4° C. for 5 min) and added in 5 ml PC12 proliferation medium, viable cells were counted with a Malassez cell using the neutral red exclusion test (Sigma).

Then the cells were seeded at $3.10^4$ cells per $cm^2$ in PC12 proliferation medium in 75 $cm^2$ plastic flasks (Greiner Ref: 658175) precoated with poly-L-lysine (10 µg/ml, Sigma Ref: P2636).

Medium was changed every other day. After 3 days of culture, when cells reached 80% of confluence, they were washed in HBSS without calcium and magnesium (Pan Biotech Ref: P06-33500) and incubated in trypsin EDTA, (0.05%, Pan Biotech Ref: P10-023100). The enzymatic reaction was stopped with PC12 proliferation medium added by 0.5 mg/ml of DNAse 1 grade 2 (Pan Biotech Ref: 760-37780100). Then, PC12 were centrifuged (800 rounds/min at 4° C. for 10 min) and cells were seeded at the density of 2.9 $10^4$ per $cm^2$ in a 175 $cm^2$ culture flask (Greiner Ref: 661195) pre-coated with poly-L-lysine.

Intoxication and MTT Viability Assay

PC12 cells (passage #2) are seeded on the basis of 3300 cells per $cm^2$ in 96-well plates (Greiner Ref: 655 180) pre-coated with poly-L-lysine (Sigma) Neurobasal medium (Invitrogen, Ref: 21103049) containing B27 (2%, Invitrogen, Ref: 21103049), penicillin (50 U/ml)-streptomycin (50

μg/ml) and glutamine (1%) and 50 ng/ml of NGF (Sigma Ref: N1408). NGF allows PC12 to differentiate in sympathetic neuron-like cells.

After 5 days of culture, the medium is changed with neurobasal added by NGF (50 ng/ml), B27 without antioxidant, glutamine and antibiotics. After 24 h, cells are incubated for 1 hour with drugs at 5 concentrations, 6 wells per condition. After 1 hour of pre-incubation, cells are intoxicated by 10 μM of beta-amyloid (25-35; Sigma) together with drugs in the cell culture medium. 24 h later, cells are washed once with PBS (Pan Biotech, Ref: P04-36100) and the PC12 cell survival was evaluated by MTT (3,[4,5-dimethylthiazol-2-yl]-2,5 diphenyltetrazoliumbromide) viability test.

Cortical Neurons Cell Culture

Primary rat cortical neurons are cultured as described by Singer et al., 1999. Briefly pregnant female rats of 15 days gestation are killed by cervical dislocation (Rats Wistar; Janvier) and the foetuses removed from the uterus. The cortexes are removed and placed in ice-cold medium of Leibovitz (L15; Invitrogen) containing 1% of Penicillin-Streptomycin (PS; Invitrogen) and 1% of bovine serum albumin (BSA; Sigma). Cortexes are dissociated by trypsinisation for 20 min at 37° C. (Trypsin EDTA 1×; Invitrogen) diluted in PBS without calcium and magnesium. The reaction is stopped by the addition of Dulbecco's modified Eagle's medium (DMEM; Invitrogen) containing DNAase I grade II (0.1 mg/ml; Roche Diagnostics) and 10% of foetal calf serum (FCS; Invitrogen). Cells are then mechanically dissociated by 3 passages through a 10 ml pipette. Cells are then centrifuged at 180×g for 10 min at 10° C. The supernatant is discarded and the cells of pellet are re-suspended in a defined culture medium consisting of Neurobasal (Invitrogen) supplemented with B27 (2%; Invitrogen), L-glutamine (0.2 mM; Invitrogen), 1% of PS solution and 10 ng/ml of brain-derived neurotrophic factor (BDNF, Pan Biotech). Viable cells are counted in a Neubauer cytometer using the trypan blue exclusion test. Cells are seeded at a density of 30,00-cells/well in 96-well plates (wells are pre-coated with poly-L-lysine (10 μg/ml; Sigma)) and are cultured at 37° C. in a humidified air (95%)/CO2 (5%) atmosphere.

After 6 days of culture, cells are incubated with drugs (5 concentrations). After 1 hour, cells are intoxicated by 20 μM of β-amyloid (25-35; Sigma) in defined medium without BDNF but together with drugs. Cortical neurons are intoxicated for 2 days.

Lactate Dehydrogenase (LDH) Activity Assay

After 2 days of culture, the supernatant is collected and analyzed with the Cytotoxicity Detection Kit (LDH, Roche Applied Sciences). This colorimetric assay for the quantification of cell death is based on the measurement of lactate dehydrogenase (LDH) activity released from the cytosol of damaged cells into the supernatant. The optic density (DO) is assessed by spectrophotometer at 492 nm wavelength by a multiscan apparatus (Thermo, Ref Ascent). Results are expressed in percentage of cell viability, compared to the negative control (vehicle).

Results

Figure 5:
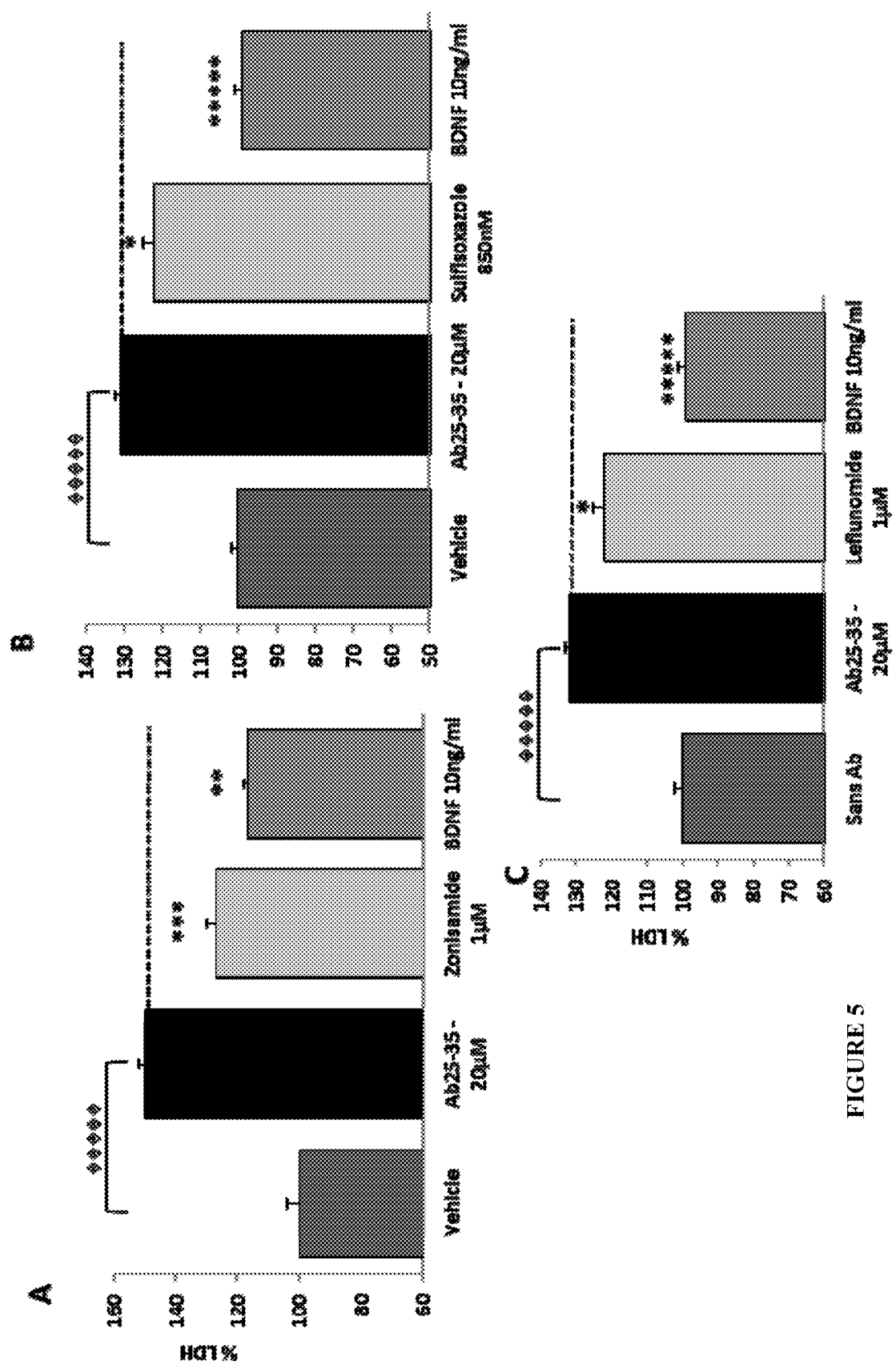
FIGS. 5A-5C: Effect of selected drugs on LDH release in beta-amyloid intoxicated rat primary cortical neuron culture.
Figure 6A:
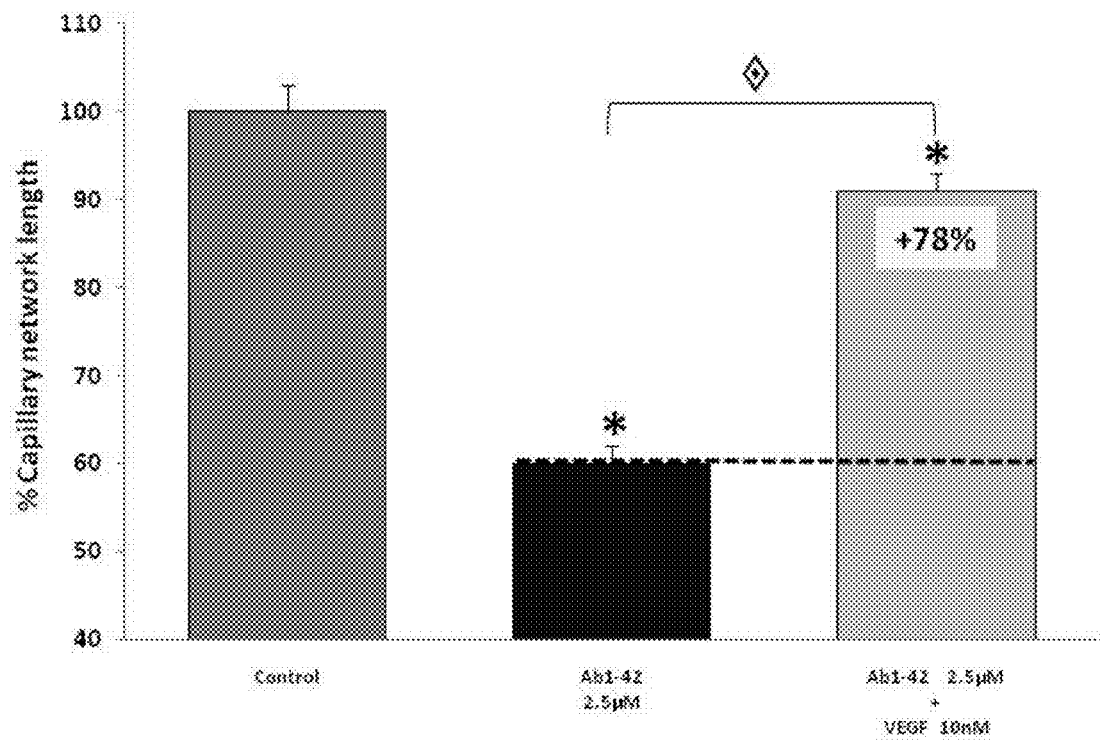
Figure 6B:
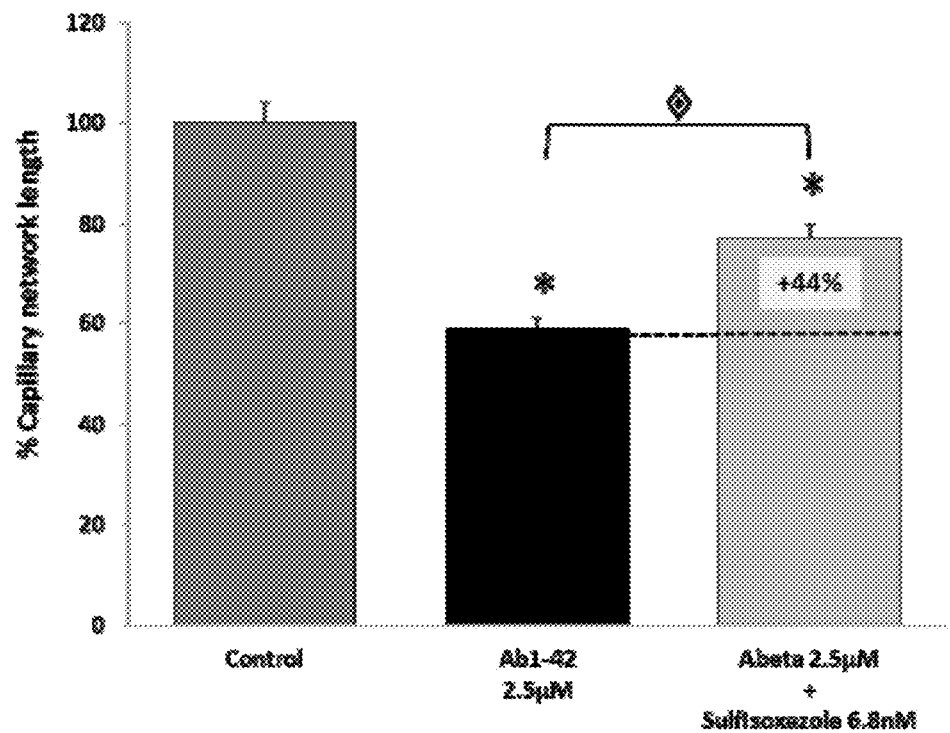
Figure 6C:
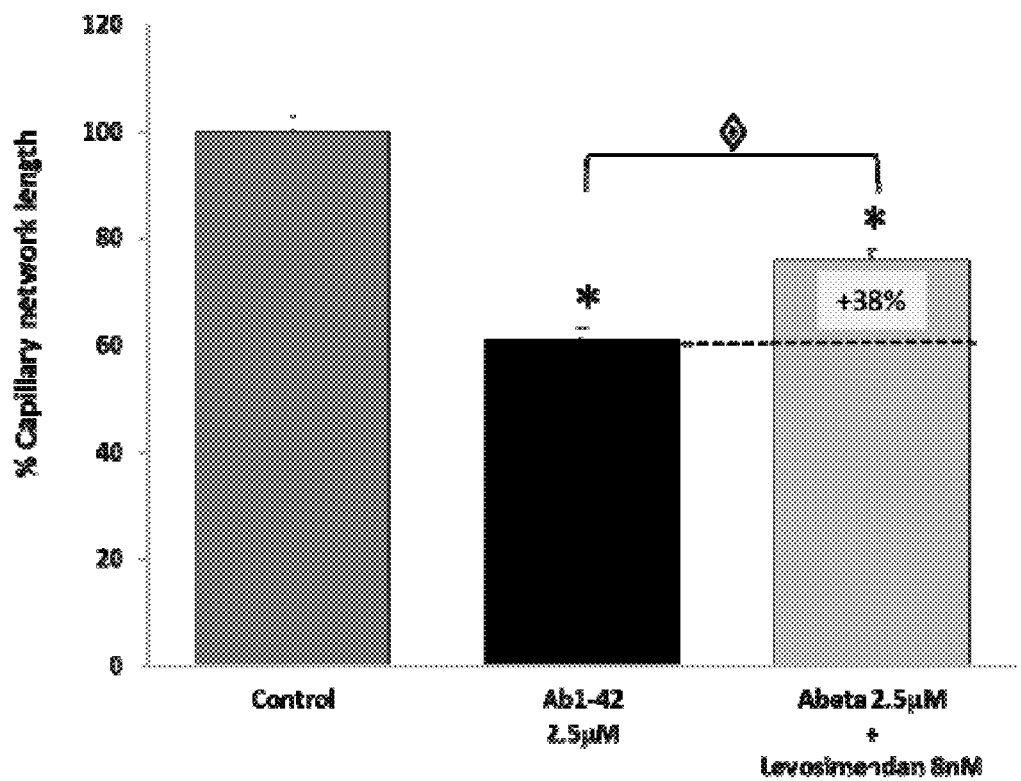
Figure 6D:
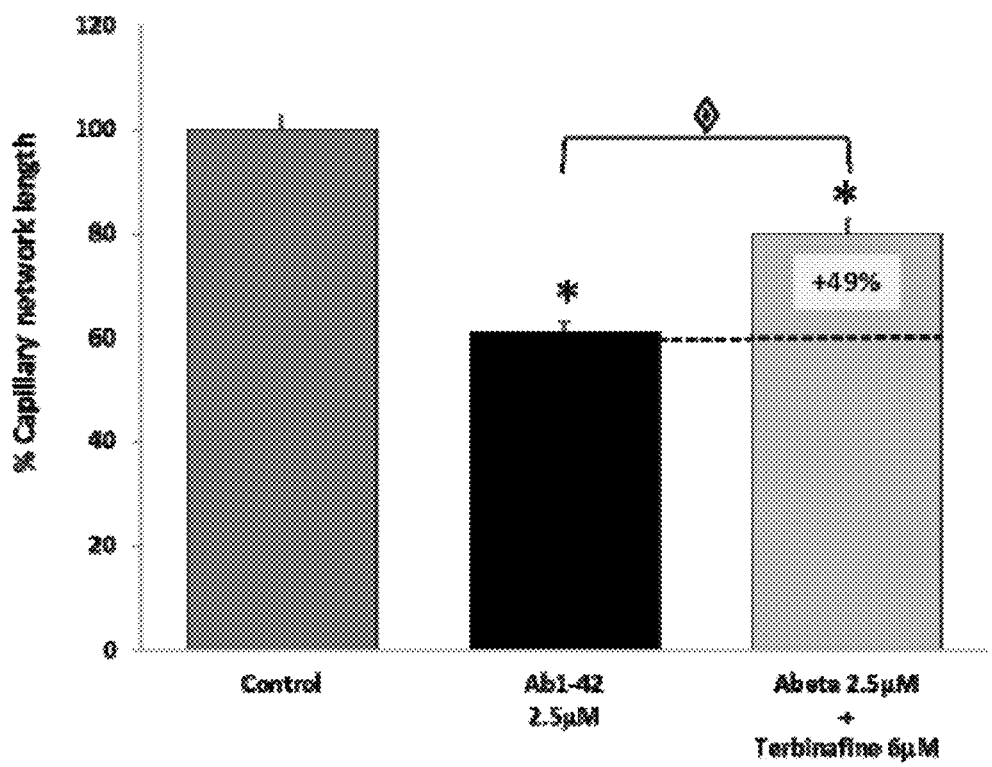
Figure 6E:
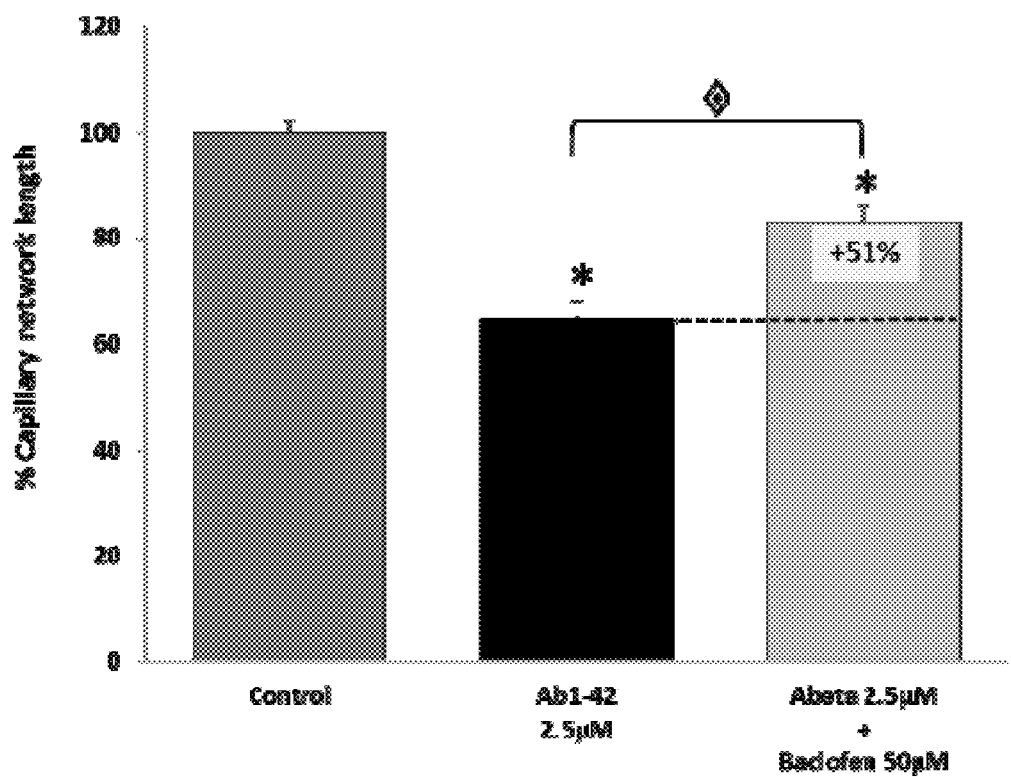
Figure 6F:
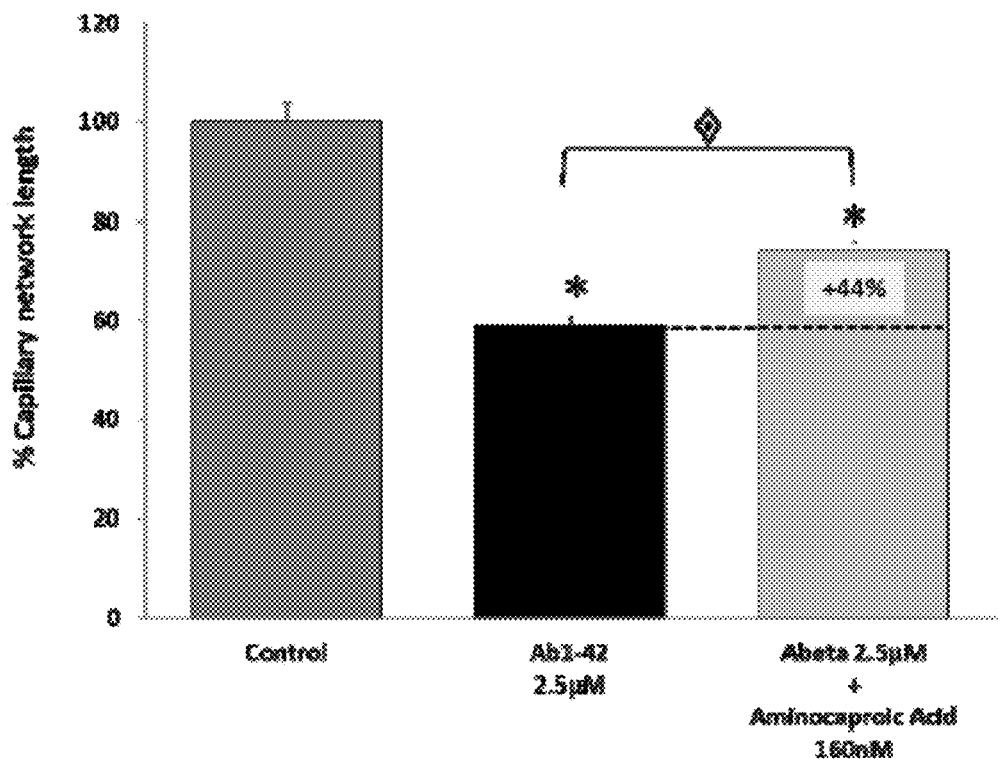
Figure 6G:
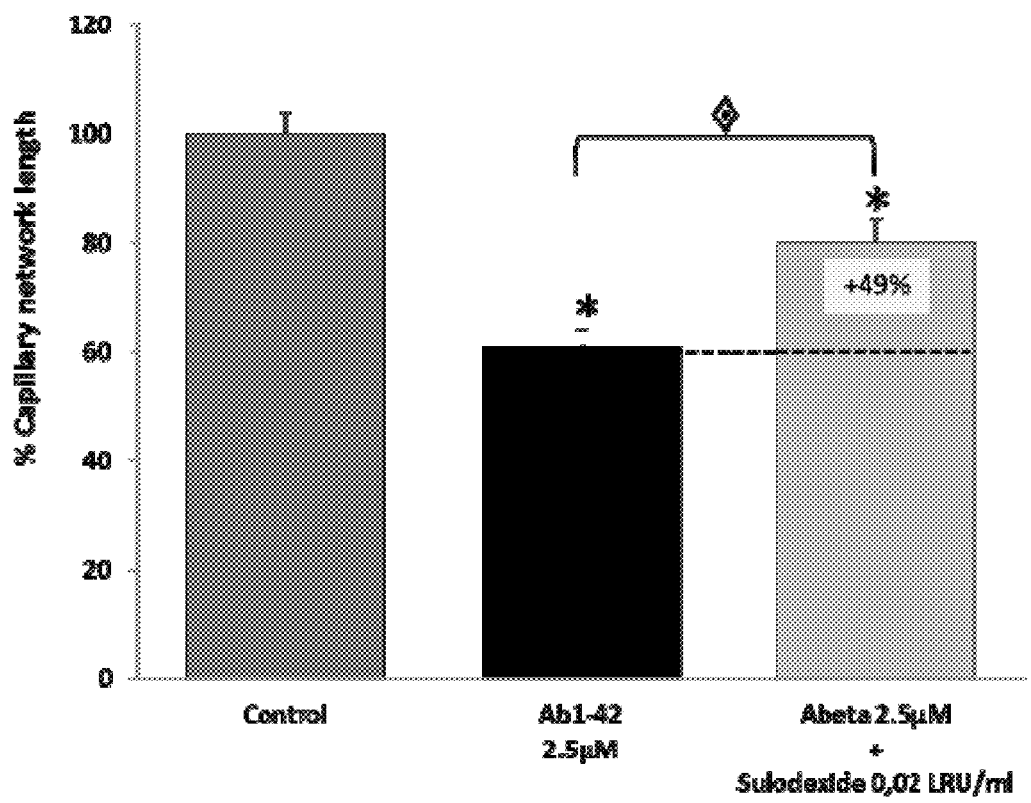
Figure 6H:
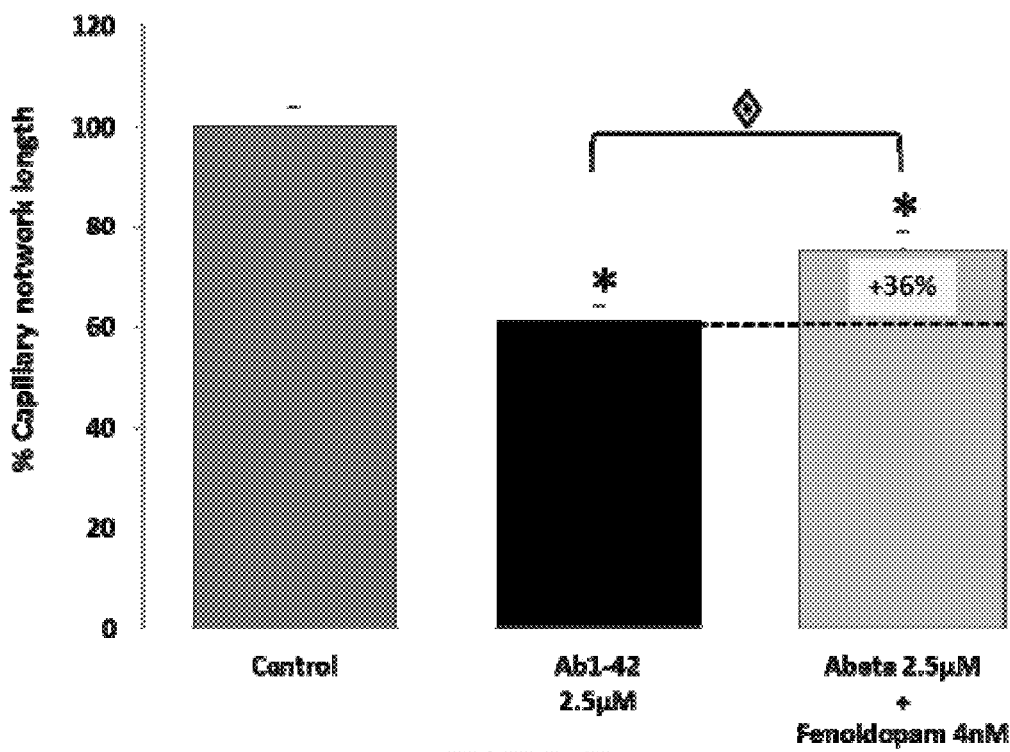
Figure 7A:
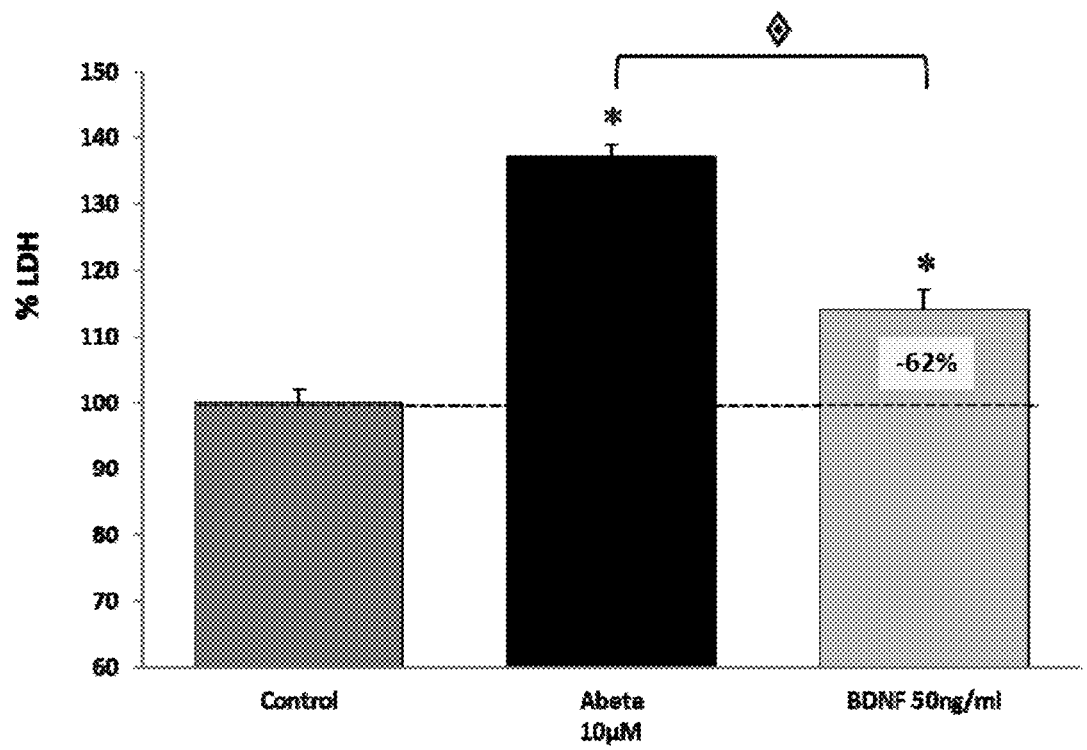
Figure 7B:
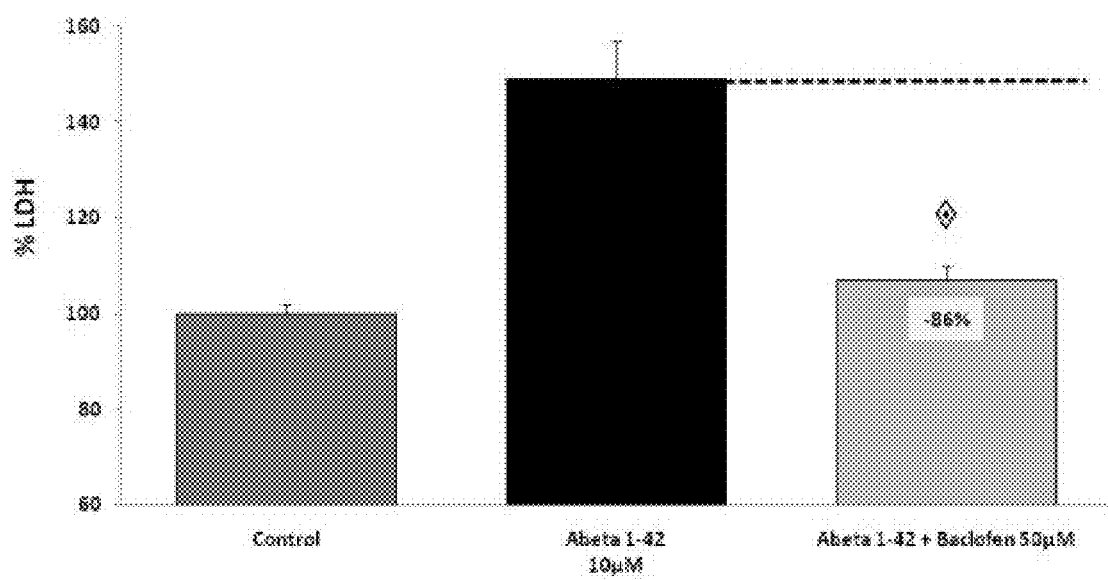
Figure 7C:
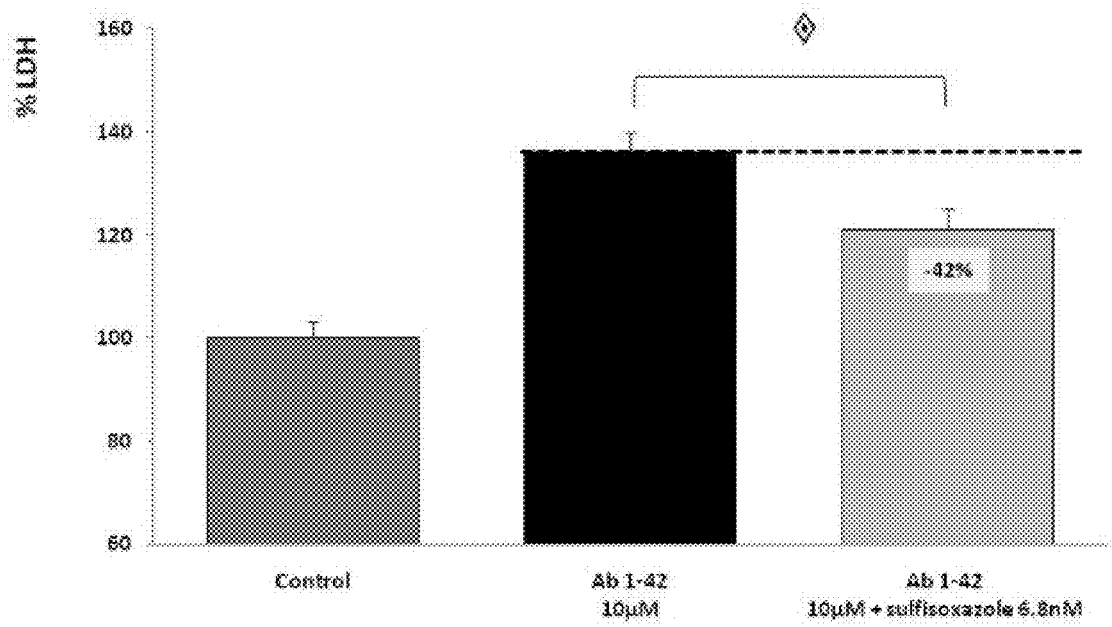
Figure 7D:
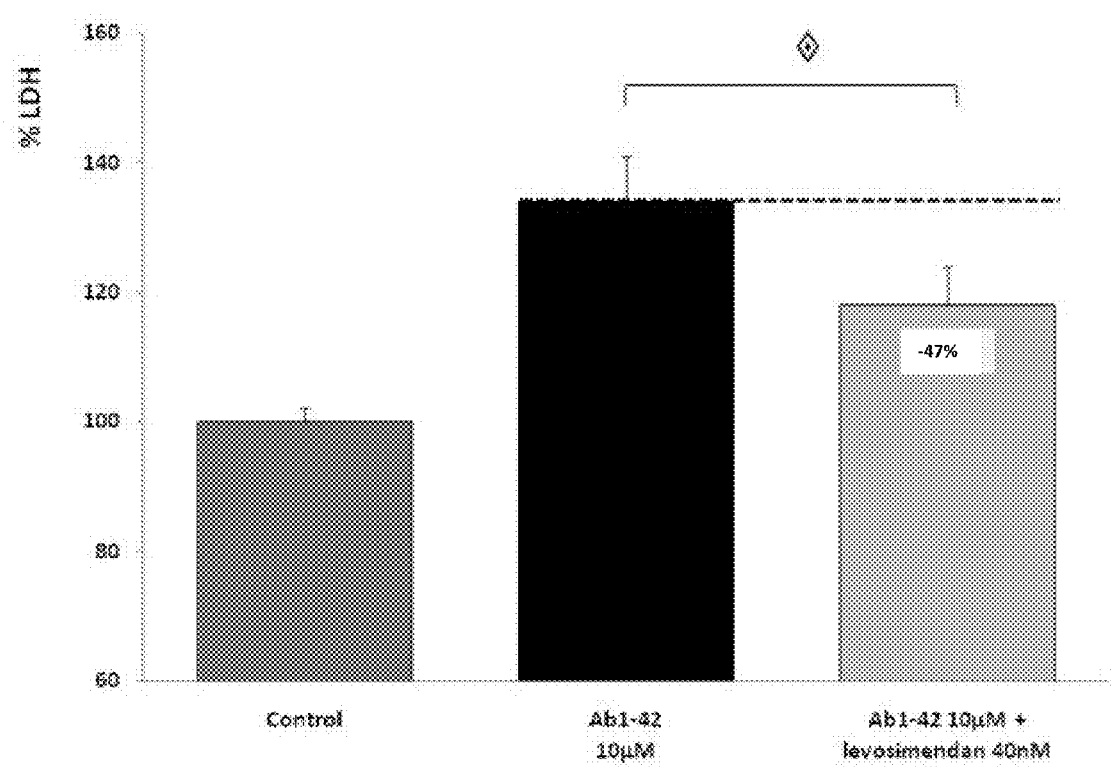
Figure 7E:
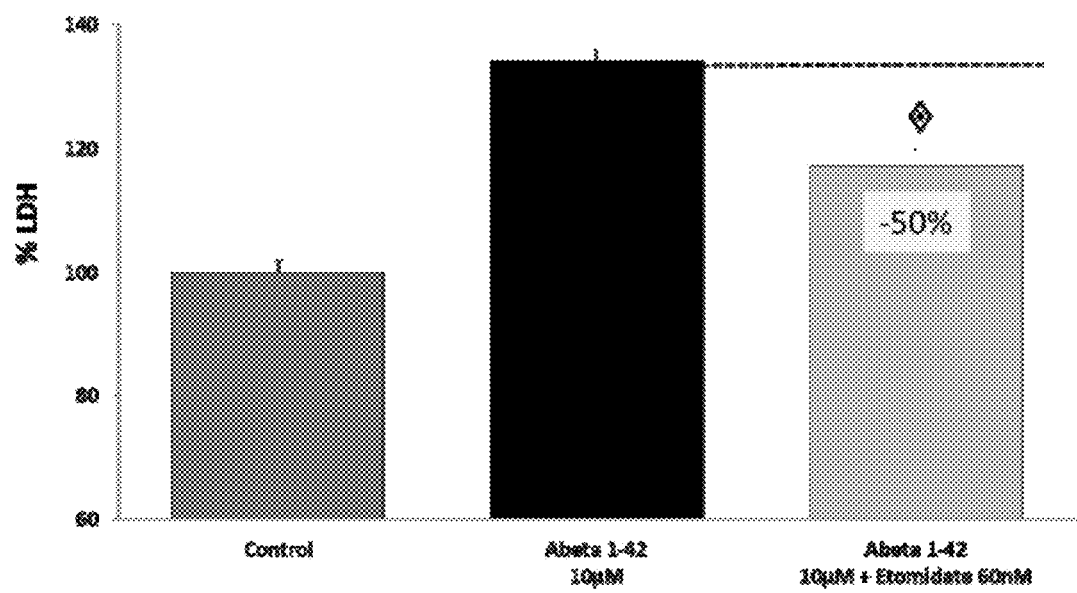
Figure 7F:
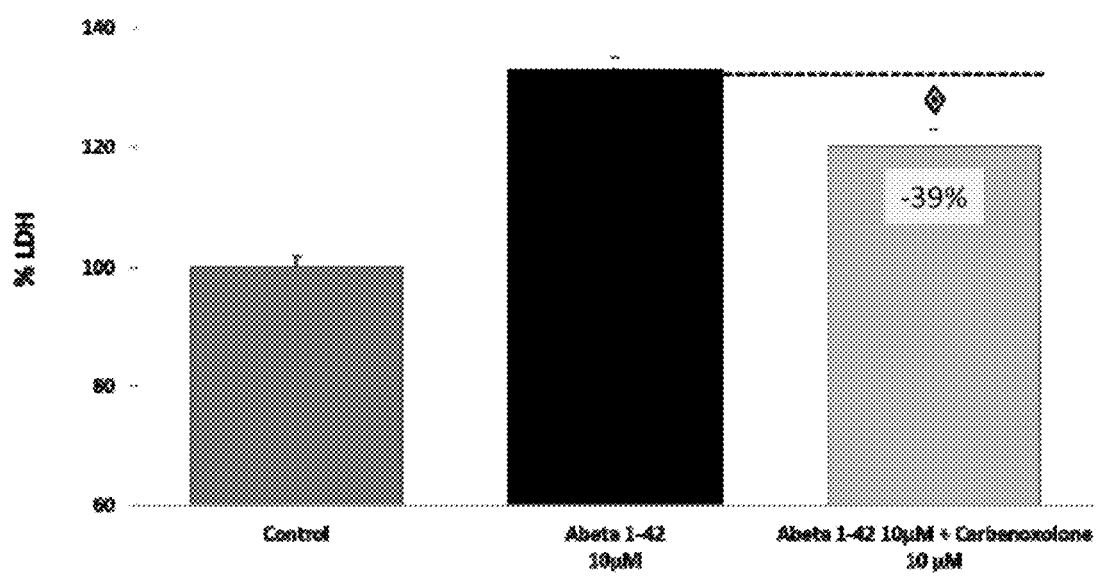
Figure 7G:
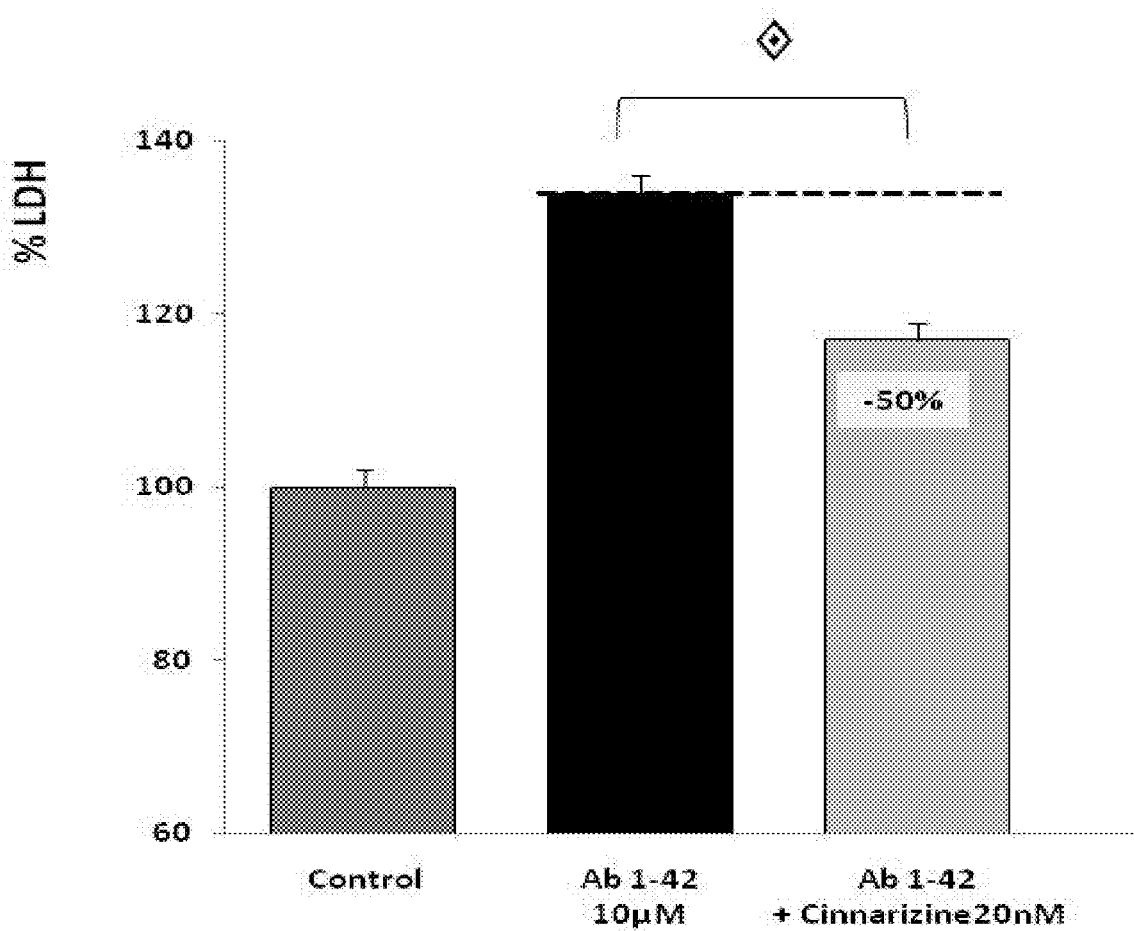

Results presented in FIGS. 4 and 5 are extracted from two independent cultures, 6 wells per condition. All values are expressed as mean±s.e.mean. A bilateral Student's t test analysis is performed on raw data. Results are expressed in percentage of neurite length, compared to the control (vehicle).

NGF-differentiated PC12 cells are incubated with drugs one hour before Abeta$_{25-35}$ 10 μM intoxication that lasts 24 hours.

One day after this incubation, the viability of NGF-differentiated PC12 is quantified, using the MTT assay. The results clearly show that prilocaine and amlodipin exert a strong neuroprotective effect against this Abeta$_{25-35}$ intoxication (FIG. 4).

Rat primary cortical neurons were also incubated with compounds of the invention one hour before Aβ$_{25-35}$ 20 μM intoxication that lasts 2 days. Two days after this incubation, LDH release in the culture medium is quantified, reflecting the level of cell death. The results presented demonstrate that compounds for use in the present invention exert a substantial protective effect against this Aβ$_{25-35}$ intoxication (FIG. 5).

I.4. Activity of Drug Combinations

In vitro assays are also carried out with several combinations of drugs modulating synapse function and/or angiogenesis and/or cell stress response.

Drugs are incubated in the same experimental conditions as described above (see sections I.1-I.3). The most efficient drug combinations acting on the targets are summarized in Table 2.

TABLE 2

| Drug combination | Neuro protective effect against the Aβ$_{25-35}$ intoxication |
|---|---|
| phenformin and zonisamide | + |
| phenformin and methyclothiazide | + |
| phenformin and acamprosate | + |
| phenformin and sulfisoxazole | + |
| baclofen and terbinafine | + |
| baclofen and risedronate | + |
| baclofen and sulfisoxazole | + |
| baclofen and zonisamide | + |
| baclofen and methyclothiazide | + |
| baclofen and leflunomide | + |
| zonisamide and dyphylline | + |
| methyclothiazide and dyphylline | + |
| zonisamide and prilocaine | + |
| methyclothiazide and prilocaine | + |
| zonisamide and sulfisoxazole | + |
| terbinafine and sulfisoxazole | + |
| terbinafine and mepacrine | + |
| acamprosate and terbinafine | + |
| terbinafine and rifabutin | + |
| phenformin and tadalafil | + |
| zonisamide and argatroban | + |
| phenformin and clopidogrel | + |
| acamprosate and cinacalcet | + |
| sulfisoxazole and cinacalcet | + |
| terbinafine and argatroban | + |
| terbinafine and cefmenoxime, | + |
| baclofen and clopidogrel | + |
| terbinafine and clopidogrel | + |
| risedronate and clopidogrel | + |
| zonisamide and cinnarizine | + |
| acamprosate and cinnarizine | + |
| zonisamide and ciclopirox | + |
| acamprosate and ciclopirox | + |
| sulfisoxazole and amobarbital | + |
| zonisamide and amobarbital | + |
| sulfisoxazole and cefotetan | + |
| zonisamide and cefotetan | + |
| acamprosate and erythrityl tetranitrate | + |
| zonisamide and erythrityl tetranitrate | + |
| sulfisoxazole and erythrityl tetranitrate | + |
| mitiglinide and erythrityl tetranitrate | + |
| levosimendan and erythrityl tetranitrate | + |
| mitiglinide and zonisamide | + |
| levosimendan and zonisamide | + |
| mitiglinide and terbinafine | + |
| levosimendan and terbinafine | + |
| mitiglinide and risedronate | + |
| levosimendan and risedronate | + |
| mitiglinide and methyclothiazide | + |
| levosimendan and methyclothiazide | + |

TABLE 2-continued

| Drug combination | Neuro protective effect against the Aβ$_{25-35}$ intoxication |
|---|---|
| methyclothiazide and sulfisoxazole | + |
| zonisamide and sulfisoxazole | + |
| risedronate and sulfisoxazole | + |
| risedronate and mepacrine | + |
| risedronate and acamprosate | + |
| risedronate and rifabutin | + |
| enprofylline and phenformin | + |
| oxtriphylline and phenformin | + |
| zonisamide and cefmenoxime | + |
| methyclothiazide and argatroban | + |
| methyclothiazide and cefmenoxime | + |
| risedronate and argatroban | + |
| risedronate and cefmenoxime | + |
| zonisamide and cinnarizine | + |
| zonisamide and benidipine | + |
| zonisamide and paramethadione | + |
| zonisamide and amlodipine | + |
| methyclothiazide and cinnarizine | + |
| methyclothiazide and benidipine | + |
| methyclothiazide and paramethadione | + |
| methyclothiazide and amlodipine | + |
| acamprosate and benidipine | + |
| acamprosate and paramethadione | + |
| acamprosate and amlodipine | + |
| methyclothiazide and ciclopirox | + |
| methyclothiazide and amobarbital | + |
| methyclothiazide and cefotetan | + |
| methyclothiazide and erythrityl tetranitrate | + |

+ indicates positive neuroprotective effect against the Aβ$_{25-35}$ intoxication

II. The Compounds Prevent Toxicity of Human Aβ$_{1-42}$

In this further series of experiments, candidate compounds have been tested for their ability to prevent or reduce the toxic effects of human Aβ$_{1-42}$. Aβ$_{1-42}$ is the full-length peptide that constitutes aggregates found in biopsies from human patients afflicted with AD. The drugs are first tested individually, followed by assays of their combinatorial action. The effect is determined on various cell types, to further document the activity of the compounds.

II.1. Protection Against the Toxicity of Aβ$_{1-42}$ on Human Brain Microvascular Endothelial Cell Model Human brain microvascular endothelial cell cultures were used to study the protection afforded by candidate compounds on Aβ$_{1-42}$ toxicity.

Human brain microvascular endothelial cerebral cells (HBMEC, ScienCell Ref: 1000, frozen at passage 10) were rapidly thawed in a water bath at +37° C. The supernatant was immediately put in 9 ml Dulbecco's modified Eagle's medium (DMEM; Pan Biotech ref: P04-03600) containing 10% of foetal calf serum (FCS; GIBCO ref 10270-106). Cell suspension was centrifuged at 180×g for 10 min at +4° C. and the pellets were suspended in CSC serum-free medium (CSC serum free, Cell System, Ref: SF-4Z0-500-R, Batch 51407-4) with 1.6% of serum-free RocketFuel (Cell System, Ref: SF-4Z0-500-R, Batch 54102), 2% of Penicillin 10,000 U/ml and Streptomycin 10 mg/ml (PS; Pan Biotech ref: P06-07100 batch 133080808) and were seeded at the density of 20,000 cells per well in 96-well plates (matrigel layer biocoat angiogenesis system, BD, Ref 354150, Batch A8662) in a final volume of 100 μl. On matrigel support, endothelial cerebral cells spontaneously started the process of capillary network morphogenesis (47).

Three separate cultures were performed per condition, 6 wells per condition.

Candidate Compounds and Human Amyloid-β$_{1-42}$ Treatment

Briefly, Aβ$_{1-42}$ peptide (Bachem, ref: H1368 batch 1010533) was reconstituted in defined culture medium at 20 μM (mother solution) and was slowly shacked at +37° C. for 3 days in the dark for aggregation. The control medium was prepared in the same conditions.

After 3 days, this aggregated human amyloid peptide was used on HBMEC at 2.5 μM diluted in control medium (optimal incubation time). The Aβ$_{1-42}$ peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the Aβ$_{1-42}$ application (in a final volume per culture well of 100 μl). One hour after test compounds or VEGF incubation (two hours after cell seeding on matrigel), 100 μl of Aβ$_{1-42}$ peptide was added to a final concentration of 2.5 μM diluted in control medium in the presence of test compounds or VEGF (in a 200 μl total volume/well), in order to avoid further drug dilutions.

Organization of Culture Plates

VEGF-165, known to be a pro-angiogenic isoform of VEGF-A, was used for all experiments in this study as a reference compound. VEGF-165 is one of the most abundant VEGF isoforms involved in angiogenesis. VEGF was used as a reference test compound at 10 nM.

The following conditions were assessed:

Negative Control: medium alone+0.1% DMSO.

Intoxication: amyloid-β$_{1-42}$ (2.5 μM) for 18 h.

Positive control: VEGF-165 (10 nM) (1 reference compound/culture) 1 hr before the Aβ$_{1-42}$ (2.5 μM) addition for a 18 h incubation time.

Test compounds: Test compound 1 hr before the Aβ$_{1-42}$ (2.5 μM) addition for a 18 h incubation time.

Capillary Network Quantification

Per well, 2 pictures with 4× lens were taken using InCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

All values are expressed as mean±s.e.mean of the 3 cultures (n=6 per condition). Statistical analyses were done on the different conditions performing an ANOVA followed by the Dunnett's test when it was allowed (Statview software version 5.0). The values (as %) inserted on the graphs show the amyloid toxicity evolution. Indeed, the amyloid toxicity was taken as the 100% and the test compound effect was calculated as a % of this amyloid toxicity.

Results

The results are shown in FIGS. 6 and 18 and in Table 3. They demonstrate that the drugs, alone, induce a substantial protective effect against the toxicity caused by Aβ peptide 1-42:

Aminocaproic acid alone, at a low dosage of e.g., 160 nM, induces strong protective effect;

Levosimendan alone, at a dose as low as 8 nM, induces a strong protective effect; and Carbamazine alone, at low dosage of e.g. 200 nM, induces a strong protective effect.

II.2 Protection Against the Toxicity of $A\beta_{1-42}$ on Primary Cortical Neuron Cells Test compound and Human amyloid-β1-42 treatment Primary rat cortical neurons are cultured as described previously.

Briefly, $A\beta_{1-42}$ peptide was reconstituted in defined culture medium at 40 μM (mother solution) and was slowly shacked at +37° C. for 3 days in the dark for aggregation. The control medium was prepared in the same conditions.

After 3 days, the solution was used on primary cortical neurons as follows:

After 10 days of neuron culture, the drug was solved in culture medium (+0.1% DMSO) and then pre-incubated with neurons for 1 hour before the $A\beta_{1-42}$ application (in a final volume per culture well of 100 μl). One hour after drug incubation, 100 μl of $A\beta_{1-42}$ peptide was added to a final concentration of 10 μM diluted in the presence of the drug, in order to avoid further drug dilutions. Cortical neurons were intoxicated for 24 hours. Three separate cultures were performed per condition, 6 wells per condition.

Organization of Culture Plates

Estradiol-β at 100 and 150 nM were used as a reference test compound and BDNF at 50 ng/ml was used as a positive control. Three separate cultures were performed per condition, 12 wells per condition.

Estradiol-β and BDNF were solved in culture medium and pre-incubated for 1 h before the aggregated amyloid-$\beta_{1-42}$ application.

The following conditions were assessed:

1 CONTROL PLAQUE: 12 wells/condition

Negative Control: medium alone+0.1% DMSO

Intoxication: amyloid-$\beta_{1-42}$ (10 μM) for 24 h

Positive control: BDNF (50 ng/ml) 1 hr followed by amyloid-$\beta_{1-42}$ (10 μM) for 24 h Reference compound: Estradiol (150 nM) 1 hr followed by amyloid-$\beta_{1-42}$ (10 μM) for 24 h.

DRUG PLATE: 6 wells/condition

Negative Control: medium alone+0.1% DMSO

Intoxication: amyloid-$\beta_{1-42}$ (10 μM) for 24 h

Drug 1: Drug 1—1 hr followed by amyloid-$\beta_{1-42}$ (10 μM) for 24 h

Drug 2: Drug 2—1 hr followed by amyloid-$\beta_{1-42}$ (10 μM) for 24 h.

Lactate Dehydrogenase (LDH) Activity Assay 24 hours after intoxication, the supernatant was taken off and analyzed with the Cytotoxicity Detection Kit (LDH, Roche Applied Science, ref: 11644793001, batch: 11800300). This colorimetric assay for the quantification of cell toxicity is based on the measurement of lactate dehydrogenase (LDH) activity released from the cytosol of dying cells into the supernatant.

Data Processing

All values are expressed as mean±s.e.mean of the 3 cultures (n=6 per condition). Statistical analyses were done on the different conditions (ANOVA followed by the Dunnett's test when it was allowed, Statview software version 5.0).

Results

The results obtained for individual selected drugs in the toxicity assays on primary cortical neuron cells are presented in Table 3 and in FIGS. 7 and 19.

TABLE 3

| DRUG NAME | Protective effect in $A\beta_{1-42}$ intoxicated neuronal cells | Protective effect in $A\beta_{1-42}$ intoxicated HBMC |
|---|---|---|
| Aminocaproic acid | | + |
| Baclofen (+/−) | + | + |
| Carbamazine | + | + |
| Carbenoxolone | + | |
| Cinacalcet | + | |
| Cinnarizine | + | |
| Eplerenone | | + |
| Etomidate | + | |
| Fenoldopam | | + |
| Leflunomide | + | |
| Levosimendan | + | + |
| Moxifloxacin | + | |
| Phenformin | + | |
| Sulfisoxazole | + | + |
| Sulodexide | | + |
| Tadalafil | + | |
| Terbinafine | | + |
| Zonisamide | + | |

These results demonstrate that the drugs, alone, induce a substantial protective effect against the toxicity caused by Aβ peptide 1-42. For example, carbamazine alone, at dose as low as 40 nM, induces a strong protective effect (FIG. 19).

II.3 Effect of Combined Therapies on the Toxicity of Human $A\beta_{1-42}$ Peptide on Human HBMEC Cells The efficacy of drug combinations of the invention is assessed on human cells. The protocol which is used in these assays is the same as described in sections II.1 above.

Results

The following drug combinations are tested on human brain microvascular endothelial cells:

baclofen and aminocaproic acid,
baclofen and levosimendan,
aminocaproic acid and sulfisoxazole,
aminocaproic acid and terbinafine,
aminocaproic acid and levosimendan,
levosimendan and sulfisoxazole,
levosimendan and terbinafine,
eplerenone and levosimendan,
eplerenone and sulfisoxazole,
eplerenone and fenoldopam,
sulodexide and levosimendan,
sulodexide and sulfisoxazole,
sulodexide and fenoldopam,
eplerenone and sulodexide,
sulodexide and sulfisoxazole,
torasemide and aminocaproic acid, or
torasemide and levosimendan.

All of the tested drug combinations give protective effect against toxicity of human $A\beta_{1-42}$ peptide in the HBMEC model, as shown in Table 4 below and exemplified in FIGS. 8 to 13 and 15 to 17.

TABLE 4

| DRUG NAME | Protective effect in $A\beta_{1-42}$ intoxicated HBMEC cells |
|---|---|
| baclofen and aminocaproic acid | + |
| baclofen and levosimendan | + |
| aminocaproic acid and sulfisoxazole | + |
| aminocaproic acid and terbinafine | + |
| aminocaproic acid and levosimendan | + |
| levosimendan and sulfisoxazole | + |

TABLE 4-continued

| DRUG NAME | Protective effect in Aβ$_{1-42}$ intoxicated HBMEC cells |
|---|---|
| levosimendan and terbinafine | + |
| eplerenone and levosimendan | + |
| eplerenone and sulfisoxazole | + |
| eplerenone and fenoldopam | + |
| sulodexide and levosimendan | + |
| sulodexide and sulfisoxazole | + |
| sulodexide and fenoldopam | + |
| eplerenone and sulodexide | + |
| sulodexide and sulfisoxazole | + |
| torasemide and aminocaproic acid | + |
| torasemide and levosimendan | + |

III. Levosimendan and Sulfisoxazole Combination Therapy Effectively Protects Neurons Against Toxicity of Human Aβ$_{1-42}$ In this example, combination therapy using Levosimendan and Sulfisoxazole was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 8:
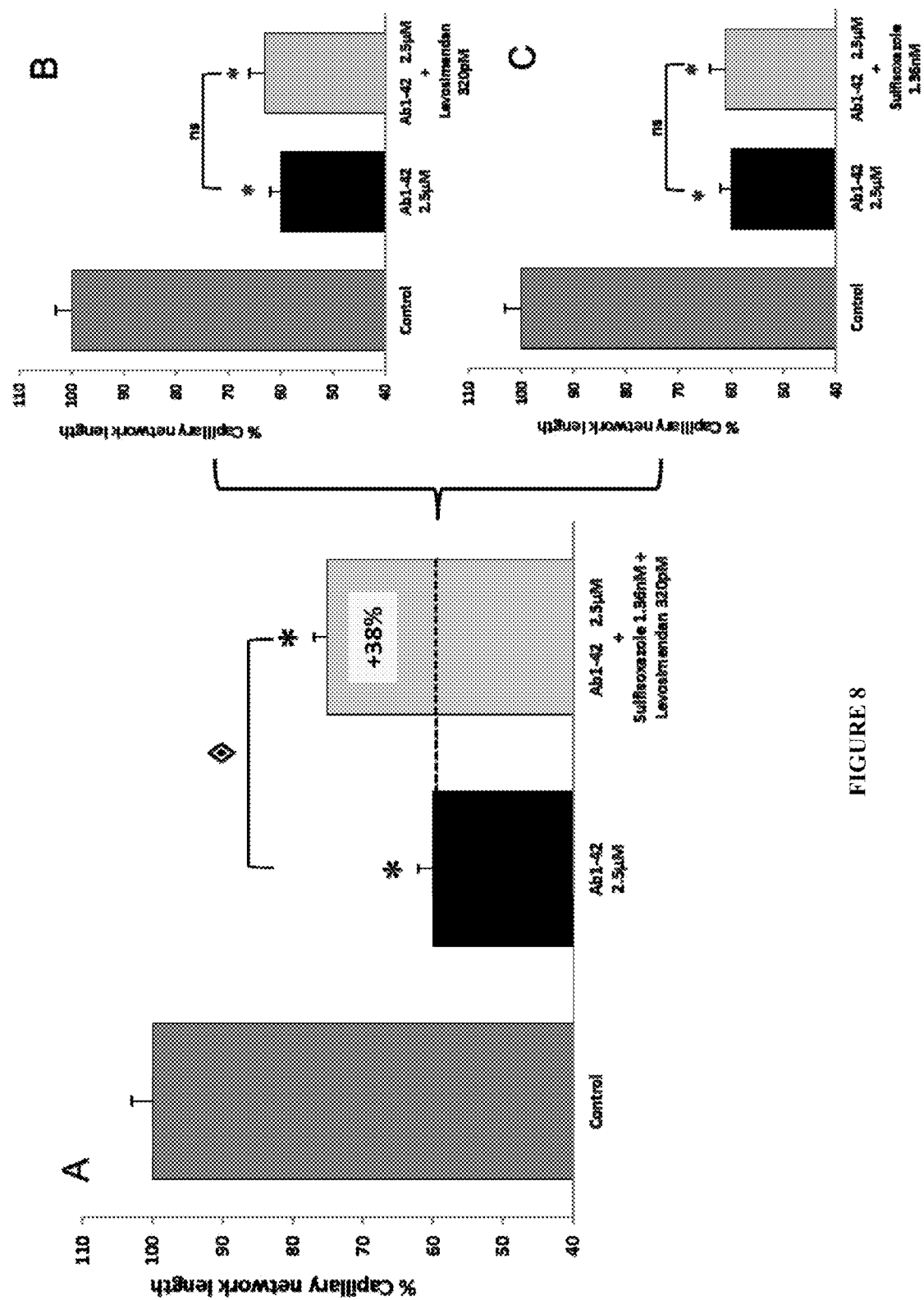

The results are presented FIG. 8. They clearly show that the aggregated human amyloid peptide (Aβ$_{1-42}$ 2.5 μM) produces significant intoxication, above 40%, compared to vehicle-treated neurons. This intoxication is significantly prevented by the combination of Sulfisoxazole and Levosimendan (FIG. 8A) whereas, at those concentrations, Levosimendan (FIG. 8B) and Sulfisoxazole (FIG. 8C) alone have no significant effect on intoxication.

IV. Terbinafine and Sulfisoxazole Combination Therapy Effectively Protects Neurons Against Toxicity of Human Aβ$_{1-42}$ In this example, combination therapy using Terbinafine and Sulfisoxazole was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 9:
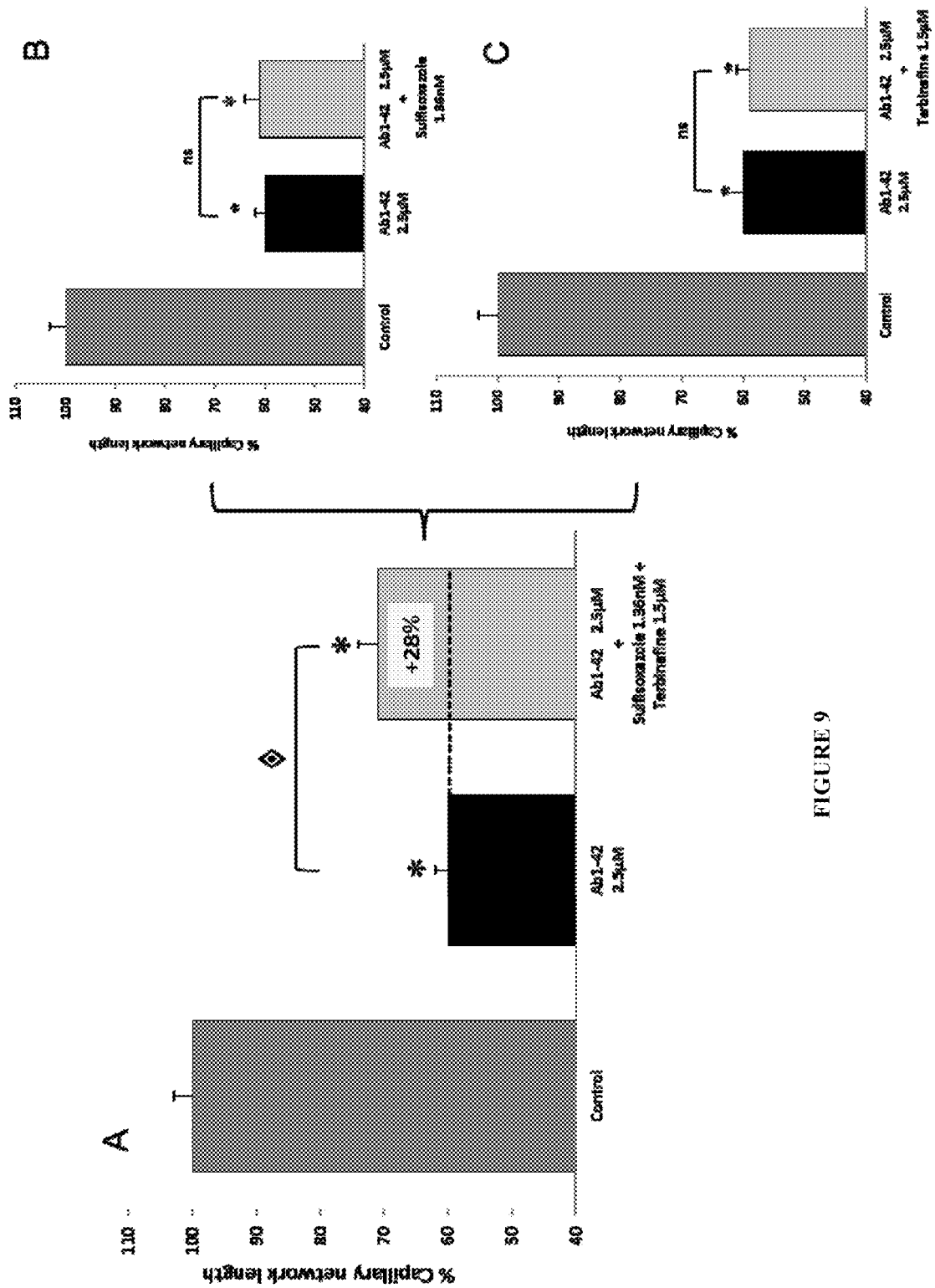

The results are presented FIG. 9. They clearly show that the aggregated human amyloid peptide (Aβ$_{1-42}$ 2.5 μM) produces significant intoxication, above 40%, compared to vehicle-treated neurons. This intoxication is significantly prevented by the combination of Terbinafine and Sulfisoxazole (FIG. 9A) whereas, at those concentrations, Sulfisoxazole (FIG. 9B) and Terbinafine (FIG. 9C) alone have no significant effect on intoxication.

V. Levosimendan and Baclofen Combination Therapy Effectively Protects Neurons Against Toxicity of Human Aβ$_{1-42}$ In this example, a combination therapy using Levosimendan and baclofen was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 10:
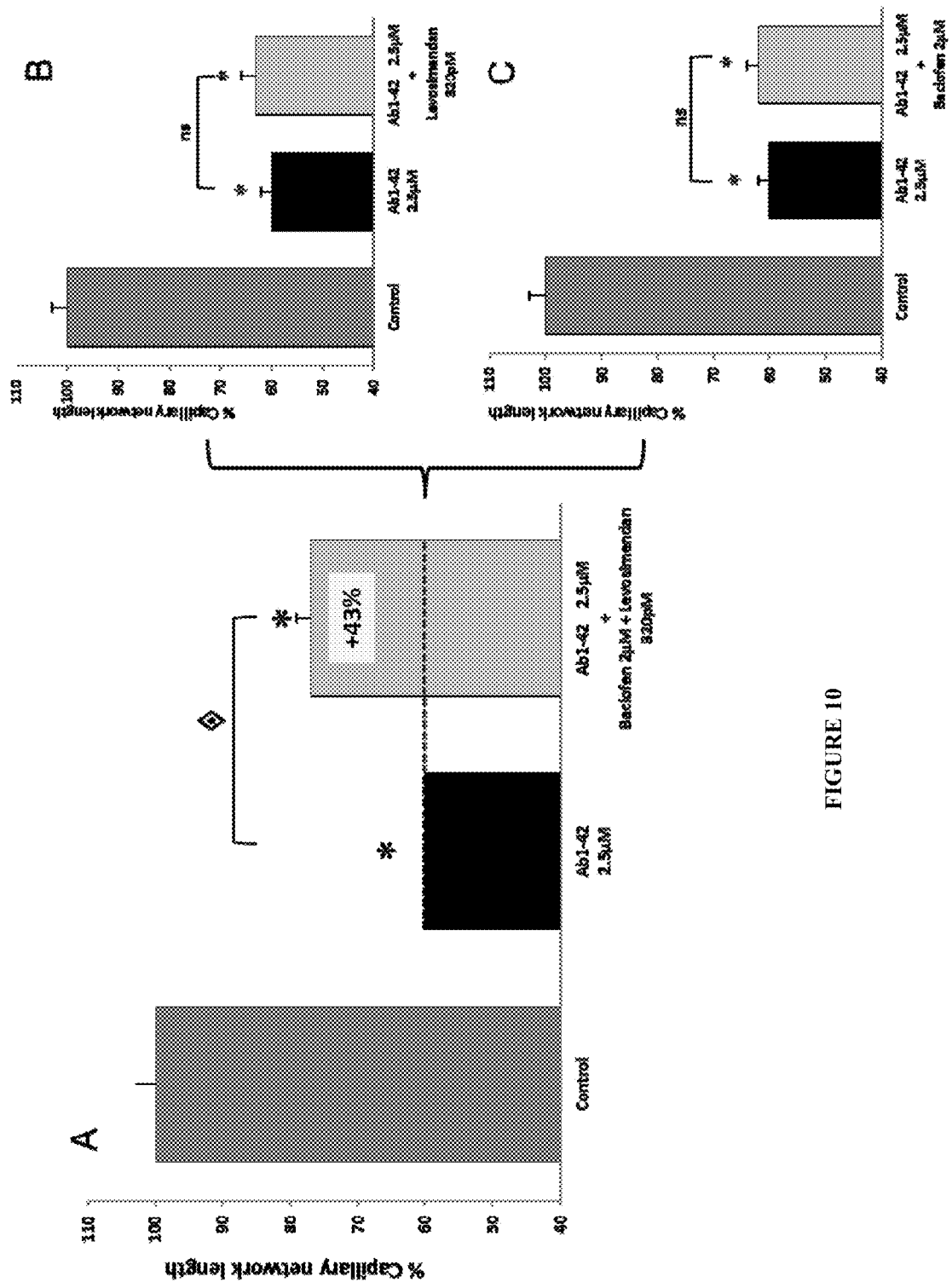

The results are presented FIG. 10. They clearly show that the aggregated human amyloid peptide (Aβ$_{1-42}$ 2.5 μM) produces significant intoxication, above 40%, compared to vehicle-treated neurons. This intoxication is significantly prevented by the combination of Levosimendan and Baclofen (FIG. 10A) whereas, at those concentrations, Levosimendan (FIG. 10B) and baclofen (FIG. 10C) alone have no significant effect on intoxication.

VI. Aminocaproic Acid and Terbinafine Combination Therapy Effectively Protects Neurons Against Toxicity of Human Aβ$_{1-42}$ In this example, a combination therapy using Aminocaproic acid and Terbinafine was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 11:
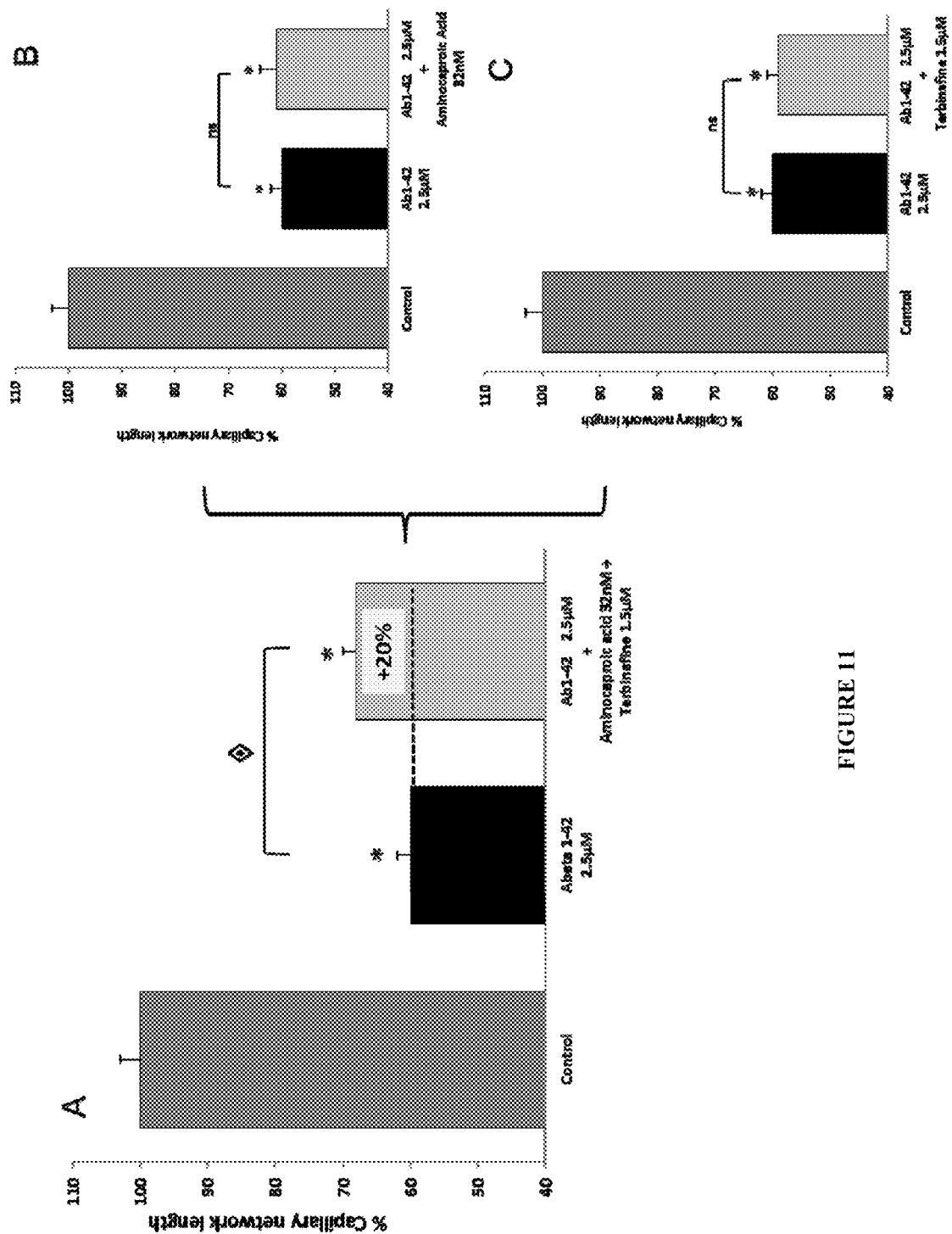

The results are presented FIG. 11. They clearly show that the aggregated human amyloid peptide (Aβ$_{1-42}$ 2.5 μM) produces significant intoxication, above 40%, compared to vehicle-treated neurons. This intoxication is significantly prevented by the combination of Aminocaproic acid and Terbinafine (FIG. 11A) whereas, at those concentrations, Aminocaproic acid (FIG. 11B) and Terbinafine (FIG. 11C) alone have no significant effect on intoxication.

VII. Aminocaproic Acid and Levosimendan Combination Therapy Effectively Protects Neurons Against Toxicity of Human Aβ$_{1-42}$ In this example, a combination therapy using Aminocaproic acid and Levosimendan was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 12:
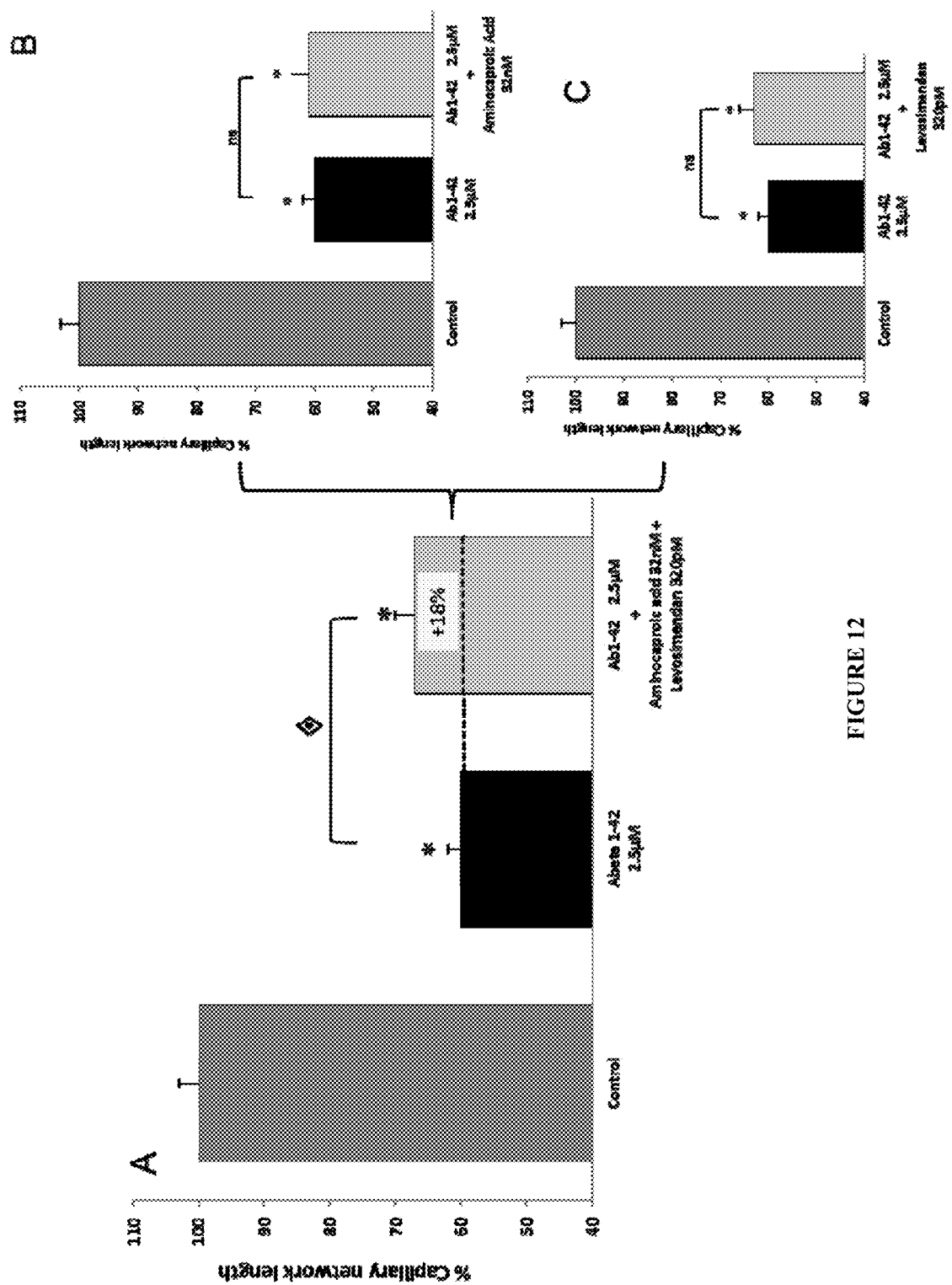

The results are presented FIG. 12. They clearly show that the aggregated human amyloid peptide (Aβ$_{1-42}$ 2.5 μM) produces significant intoxication, above 40%, compared to vehicle-treated neurons. This intoxication is significantly prevented by the combination of Aminocaproic acid and Levosimendan (FIG. 12A) whereas, at those concentrations, Aminocaproic acid (FIG. 12B) and Levosimendan (FIG. 12C) alone have no significant effect on intoxication.

VIII. Terbinafine and Levosimendan Combination Therapy Effectively Protects Neurons Against Toxicity of Human Aβ$_{1-42}$ In this example, a combination therapy using Levosimendan and Terbinafine was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 13:
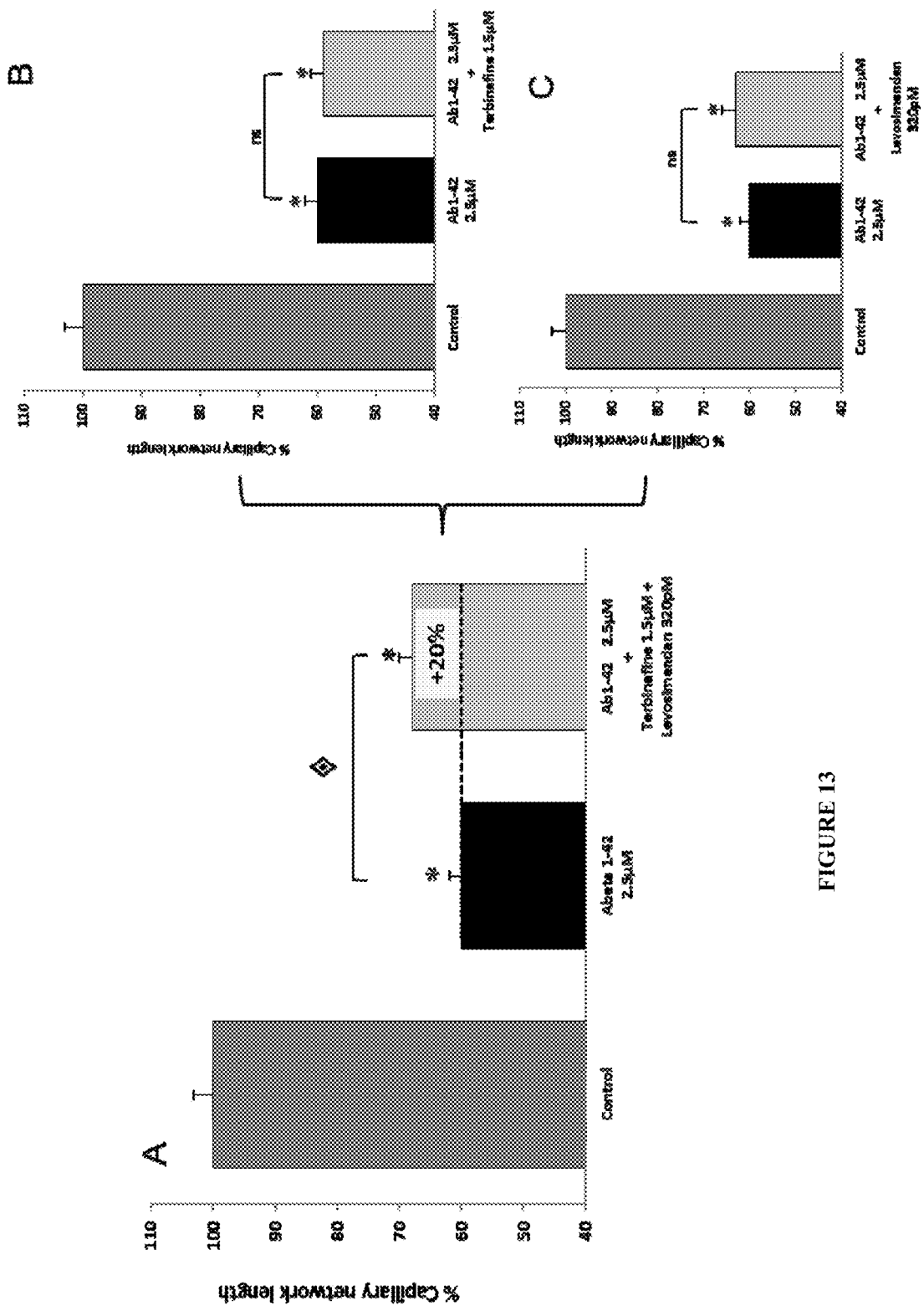

The results are presented FIG. 13. They clearly show that the aggregated human amyloid peptide (Aβ$_{1-42}$ 2.5 µM) produces significant intoxication, above 40%, compared to vehicle-treated neurons. This intoxication is significantly prevented by the combination of Terbinafine and Levosimendan (FIG. 13A) whereas, at those concentrations, Terbinafine (FIG. 13B) and Levosimendan (FIG. 13C) alone have no significant effect on intoxication.

IX. Carbamazine and Acamprosate Combination Therapy Effectively Protects Neurons Against Toxicity of Human Aβ$_{1-42}$ In this example, combination therapy using carbamazine and acamprosate was assessed for its ability to prevent or reduce the toxic effects of human Aβ$_{1-42}$.

The combination therapy was tested under experimental conditions disclosed in Example II.2. Primary rat cortical neurons cultures were used, as disclosed in II.2., and incubated simultaneously or sequentially with the drug combination.

The results are presented FIG. 14. They clearly show that the aggregated human amyloid peptide (Aβ$_{1-42}$ 2.5 µM) produces significant intoxication. This intoxication is significantly prevented by the combination of carbamazine and acamprosate (FIG. 14).

X. Sulfisoxazole and Sulodexide Combination Therapy Effectively Protects Endothelial Cells Against Toxicity of Human Aβ$_{1-42}$ In this example, combination therapy using sulfisoxazole and sulodexide was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 15:
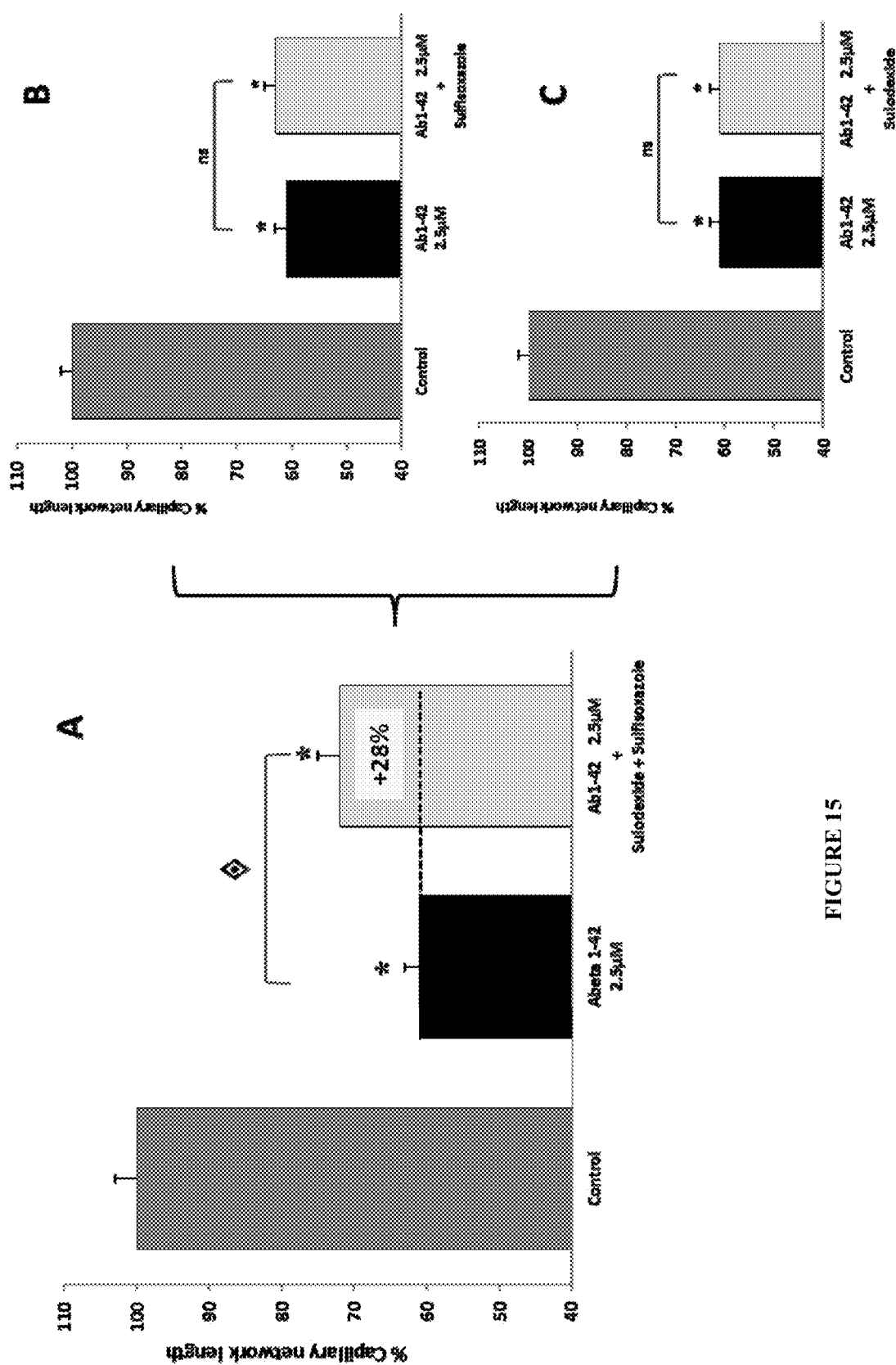

The results are presented FIG. 15. They clearly show that the aggregated human amyloid peptide (Aβ$_{1-42}$ 2.5 µM) produces significant intoxication, above 40%, compared to vehicle-treated neurons. This intoxication is significantly prevented by the combination of sulodexide and sulfisoxazole (FIG. 15A). whereas, at those concentrations, Sulfisoxazole (FIG. 15B) and Sulodexide (FIG. 15C) alone have no significant effect on intoxication.

XI. Aminocaproic Acid and Torasemide Combination Therapy Effectively Protects Endothelial Cells Against Toxicity of Human Aβ$_{1-42}$ In this example, combination therapy using Aminocaproic acid and Torasemide was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

The results are presented FIG. 16. They clearly show that the aggregated human amyloid peptide (Aβ$_{1-42}$ 2.5 µM) produces significant intoxication, above 40%, compared to vehicle-treated neurons. With a prevention of 48%, this intoxication is significantly prevented by the combination of Aminocaproic acid and Torasemide (FIG. 16).

XII. Torasemide and Levosimendan Combination Therapy Effectively Protects Endothelial Cells Against Toxicity of Human Aβ$_{1-42}$ In this example, combination therapy using torasemide and levosimendan was assessed for its ability to prevent or reduce the toxic effects of human Aβ$_{1-42}$.

The combination therapy was tested under experimental conditions disclosed in Example II.1. Human brain microvascular endothelial cell cultures were used, as disclosed in II.1., and incubated simultaneously or sequentially with the drug combination.

The results are presented FIG. 17. They clearly show that the aggregated human amyloid peptide (Aβ$_{1-42}$ 2.5 µM) produces significant intoxication, above 40%, compared to vehicle-treated neurons. This intoxication is significantly prevented by the combination of torasemide and levosimendan (FIG. 17).

IX. In Vivo Activity

Compounds and their combinations active in in vitro tests are tested in in vivo models of Alzheimer disease. Overexpression of Alzheimer's disease-linked mutant human amyloid beta protein precursor (APP) transgenes has been the most reliable means of promoting deposition of Abeta in the brains of transgenic mice that served as AD models in numerous studies. As they age, these mutant APP mice develop robust amyloid pathology and other AD-like features, including decreased synaptic density, reactive gliosis, and some cognitive deficits. Many mutant APP mouse models show little evidence of overt neuronal loss and neurofibrillary tangle (NFT) pathology. Mice hemizygous for this BRI-Abeta42 transgene are viable and fertile with a normal lifespan. Transgenic BRI-Abeta42 mRNA is expressed in a pattern characteristic of the mouse prion protein promoter; the highest transgene expression levels are detected in the cerebellar granule cells and hippocampus, followed by the cortex, pons, thalamus, and midbrain. In the transgenic fusion protein, Abeta1-42 is fused to the C terminus of the BRI protein at the furin-like cleavage site such that cleavage results in efficient Abeta1-42 secretion into the lumen or extracellular space. Therefore, these mice specifically express the Abeta1-42 isoform. Hemizygous BRI-Abeta42 mice accumulate detergent-insoluble amyloid-beta with age and develop cored plaques in the cerebellum at as early as 3 months of age. Development of forebrain pathology occurs later; extracellular Abeta plaques are not present consistently in the hippocampus and entorhinal/piriform cortices until 12 months of age. Amyloid beta deposits (cored plaques) can be observed as early as 3 months in the molecular layer of the cerebella of transgenic mice and become more pronounced with age; occasional extracellular plaques are seen in the entorhinal/piriform cortices and hippocampus at 6 months of age, but aren't consistently found until >12 months of age. The oldest mice show widespread pathology with cored and diffuse plaques in the cerebellum, cortex, hippocampus, and olfactory bulb. Extracellular amyloid plaques show dense amyloid cores with radiating fibrils; many bundles of dystrophic neurites are observed at the periphery of these plaques. Reactive gliosis is associated with plaques.

Drug Treatments

The transgenic Tg (Prnp-ITM2B/APP695*42) A12E mc mice (37) have been obtained from Jackson Laboratory (http://jaxmice.jax.org/strain/007002.html). Mice found with the highest A β42 plasma levels, line BRI-A β42A (12e), have been maintained on a mixed B6C3 background. Adult male transgenic mice have free access to food and water. In accord with an approved Institutional Animal Care and Use Committee protocol, mice are weighed and injected i.p. or force fed once daily for 10 to 20 consecutive weeks with either a control solution (placebo) or drugs of the present invention or drug combinations of Table 2, prepared at different doses.

Survival Analysis

Survival rates have been analyzed using Kaplan-Meier methods. Holm-Sidak methods (post hoc) have been used for all pairwise multiple comparison tests. The extraneous deaths are censored. All comparisons have been made between littermates to limit any potentially confounding effects from background strain differences.

Behavioural Tests

Behavioural tests were designed and conducted according to the methods published by several authors (38-41).

Spatial Learning and Memory in the Morris Water Maze (MWM)

This experiment is performed in a circular pool, 90 cm in diameter, made of white plastic and filled with milky colored water. An escape platform, 8 cm in diameter, made of clear plastic was submerged 0.5 cm under the water level. Visual clues are provided by different geometrical forms printed in A4-sized letters and placed on the four surrounding walls (distance from the pool was from 50 to 70 cm). Each mouse has been given four trials daily (5- to 7-minute interval between trials, a total of 16 trials) for 4 days. Each trial has been performed from one of four different starting points. The movement of the mice is monitored using Videotrack Software (View Point). The time taken to locate the escape platform (escape latency: up to 60 seconds) has been determined. After locating the platform the mouse has been allowed to sit on it for 15 seconds. Mice who failed to find the platform within 60 seconds have been guided to it and allowed to stay on it for 15 seconds. A latency of 60 seconds is entered into the record for such an occurrence. All four trials per day have been averaged for statistical analysis, except for the first trial on day 1. On day 9 (5 days after the last training) mice have been subjected to a 60-second probe trial in which the platform is removed and the mice are allowed to search for it. The time that each animal spent in each quadrant has been recorded (quadrant search time). Several groups of male mice have been used at 3, 7, 10, and 12 months.

The few mice that showed freezing behaviour (e.g., lying motionless in the water and refusing to swim) that strongly interfered with the test have been excluded from the data analysis. All behavioural tests are conducted in a quiet and light-reduced environment.

Working Memory Test in Radial Arm Water Maze

This cognitive-based sensitive measure of working memory has been obtained with the help of an apparatus consisting of a 100 cm-diameter water-filled pool (also used for the Morris water maze and Platform Recognition tasks) fitted with an aluminum insert to create six radially-distributed swim arms. Testing consists of five 1-min trials per daily session, for 9-12 consecutive days. At the start of each session, a clear submerged platform is positioned at the end of one of the six swim arms (randomly selected, changed daily). For each of the first four acquisition trials, the animal is placed into one of the non-platform containing arms (randomized sequence) and allowed to search for the platform. During the 60 s trial, each time the animal enters another non-platform containing arm, it is gently returned to its starting location and an error recorded. After the fourth trial, the animal is allowed to rest for 30 min, followed by a fifth (retention) trial, which originates in the final non-platform containing swim arm. The number of errors (incorrect arm choices) and escape latency (time to reach platform, maximum 60 s) are recorded for each trial.

Spatial Reference Learning and Memory in Circulate Platform Test

This cognitive-based task test is performed with the help of an apparatus that consists of a 69 cm-diameter circular platform having 16 "escape" holes spaced equidistantly around the circumference. An escape refuge is installed beneath one of the holes, and a black curtain, on which are placed various visual cues, encircles the platform. The animal is placed in the center of the platform at the start of a single 5 min trial and aversive stimuli (bright lights, fan wind) are presented. The total number of errors (head-pokes into non-escape holes) and escape latency (time to reach escape hole) are recorded.

Recognition Ability in Platform Recognition Test

This cognitive-based search task evaluates object identification and recognition ability. The target object consists of a 9 cm-diameter circular platform fitted with a 10 cm×40 cm black ensign, which is positioned 0.8 cm above the surface of the water in a 100 cm-diameter circular pool. Testing consists of four 60 s trials per day on each of four consecutive days. On each day, the target object is placed into a different quadrant of the pool for each trial, and the animal is released at the same location along the circumference of the pool for all four trials. The total latency (maximum 60 s) is recorded for each trial.

Modified Irwin Examination

A comprehensive screen, modified from Irwin, is used to determine whether any of the mice exhibited physiological, behavioural, or sensorimotor impairments related to their genotype. To explore motor skills, coordination, and muscle strength, the mice are placed on a wire that was tightened between two 30-cm-high columns and their ability to balance on the wire is assessed. In addition, their ability to grasp and hang on the wire with all four paws for at least 5 seconds and to climb back on the wire is determined.

Quantification of Vascular Amyloid Deposition

For quantification of cerebral amyloid angiopathy (CAA), 5 µm paraffin-embedded sections at 30 µm intervals through the parietal or cerebellar cortex leptomeninges are immunostained with biotinylated-Ab9 antibody (anti-Aβ1-16, 1:500) overnight at 4° C. (n=5-7 mice per genotype at each age group, n=6 sections per mouse). Positively stained blood vessels are visually assessed using modified Vonsattel's scoring system (42) The CAA severity score is calculated by multiplying the number of CAA vessels with the CAA severity grade.

Histology: Immunohistochemistry and Immunofluorescence

Tg and WT mice from 3 to 12 months are anesthetized and transcardially perfused sequentially with 0.9% NaCl and 4% paraformaldehyde in 0.1 mol/L phosphate-buffered saline (PBS) (pH 7.4) or 10% formalin and 4% paraformaldehyde in 0.1 mol/L PBS (pH 7.4). Brains and spinal cords are removed and stored in 4% paraformaldehyde. Some samples are embedded in paraffin and cut on a sliding microtome at a thickness of 10 µm. Cryosections (14 µm) are cut on a cryostat and mounted on chrome alum-coated slides. Endogenous peroxidase is quenched by treating the section with methanol containing 0.3% $H_2O_2$ for 30 minutes. Sections are blocked in 10% horse serum. Primary antibodies are used and incubated overnight at 4° C. in the presence of 1% horse serum. All secondary biotinylated or fluorescein-, Texas Red-, and AMCA-coupled antibodies, fluorochromes, ABC-kit, and 3,3'-diaminobenzidine as chromogen for peroxidase activity are from Vector Laboratories. Incubation with the secondary antibody is held at room temperature for 1 hour. All washing steps (3-10 minutes) and antibody dilution are performed using phosphate-buffered saline (0.1 mol/L PBS, pH 7.4) or Tris-buffered saline (0.01 mol/L Tris, 0.15 mol/L NaCl, pH 7.4). Incubation with the ABC complex and detection with 3,3'-diaminobenzidine is carried out according to the manufacturer's manual. Hematoxylin counterstaining is performed according to standard procedures. A minimum of three mice per genotype, age, and sex are used for each determination (43).

Preparation of Brain Extracts

Brains are rapidly harvested over ice between 90 and 120 min after the final injection and frozen to −80° C. The right cerebral hemisphere from each mouse is weighed after freezing. Analysis of hemisphere mass by median absolute deviation allows us to exclude samples that are beyond 4 median absolute deviations from the rest of the set. Cerebral hemispheres are homogenized, and cell lysates containing whole protein are prepared according to the manufacturer's instructions for enzymatic assay kits (R&D Systems, Inc.). In brief, the brain cortices are homogenized in 800 µl of low salt containing 1× extraction buffer (R&D kit) and incubated on ice for 10 min. The homogenates are then centrifuged at 13,000 g for 15 min at 4° C. The protein concentration in each sample is estimated according to biuret-derived assay (Pierce). Levels of APP, Aβ40, and Aβ42 are measured by Western immunoblotting and sandwich ELISA techniques. In addition, activities of α, β-, and γ-secretases may be measured from the same extracts.

Assay of Levels of Total APP in Mouse Cerebral Cortex Extracts

An equal-protein amount of brain extracts is loaded in each gel, 30 µg per lane per sample. Each gel contained eight treatments: control; drug1 7.5 mg/kg dose; and drug 2 in several doses. To minimize intra-gel variation, each gel contained three sets of all treatment groups. Each blot is probed with 22C11 antibody. Each blot is also probed with the β-actin antibody for normalization to transfer efficiency. The intensity of APP band signal is normalized with that of β-actin. Two sample "controls" are loaded in each gel/blot to test for blot to blot variation. Analysis of blots is performed in two ways: blot-wise (n=3), to test for gel to gel variation, and combined blots (n=9 or 10) as described (38-39). Blot-wise analysis with n=3 shows the same trend as the final analysis with n=9 or 10 does. Results of the combined analysis are presented.

Aβ Sandwich ELISA

For brain Aβ ELISAs, forebrain and hindbrain Aβ levels are determined independently, and the olfactory bulb is excluded from analysis. For plasma Aβ analysis, blood is collected in EDTA-coated tubes after cardiac puncture. Blood samples are centrifuged at 3000 rpm for 10 min at 4° C., and the plasma is aliquoted and stored at −80° C. until used. Aβ levels are determined by end-specific sandwich ELISAs using Ab9 (anti-Aβ1-16 Ab) as the capture Ab for Aβ40, 13.1.1-HRP (anti-Aβ35-40 Ab) as the detection Ab for Aβ40, 2.1.3 (anti-Aβ35-42 Ab) as the capture Ab for Aβ42, and Ab9-HRP as the detection Ab for Aβ42 (n=5-7 mice per genotype at each age group). Aβ levels are normalized to the previous results using the same sets of mice as internal controls to minimize potential ELISA variability, as described (46).

Western Blotting

Snap-frozen forebrain samples are homogenized in radio-immunoprecipitation assay (RIPA) buffer (Boston BioProducts, Worcester, Mass.) with 1% protease inhibitor mixture (Roche). The homogenate is centrifuged at 100,000×g for 1 h at 4° C. Protein concentration in supernatants is determined using the BCA protein assay (Pierce). Protein samples (20 µg) are run on Bis-Tris 12% XT gels or Bis-Tris 4-12% XT gels (Bio-Rad, Hercules, Calif.) and transferred to 0.2 µm nitrocellulose membranes. Blots are microwaved for 2 min in 0.1 M PBS twice and probed with Ab 82E1 (anti-Aβ1-16, 1:1000; IBL, Gunma, Japan) and anti-APP C-terminal 20 amino acids (1:1000) as described (46). Blots are stripped and reprobed with anti β-actin (1:1000; Sigma) as a loading control. Relative band intensity is measured using ImageJ software.

Quantification of Parenchymal Amyloid Deposition

Hemibrains are immersion fixed in 10% formalin and processed for paraffin embedding. Brain tissue sections (5 µm) are immunostained with anti-total Aβ antibody (Ab). Sections are counterstained with hematoxylin. Six sections per brain through the hippocampus, piriform cortex (bregma, −1.70 to −2.80 mm), or cerebellum (paraflocculus, crus ansiform, and simple lobules; bregma, −5.40 to −6.36 mm) are used for quantification (n=5-7 mice per genotype at each age group). The Aβ plaque burden is determined using MetaMorph software (Molecular Devices, Palo Alto, Calif.). For quantification of cored plaques, serial sections of those analyzed for Aβ burden are stained with thioflavine S (ThioS), and the number of ThioS-positive plaques in the hippocampus, entorhinal/piriform cortex, or the cerebellum is counted. All of the above analyses are performed in a blinded manner.

Statistical Analysis of In Vivo Data

Results from all experiments are analyzed with STATISTICA 8.0 (Statsoft). Aβ levels, amyloid plaque burden, and CAA severity are analyzed by using ANOVA with the post hoc Holm-Sidak multiple comparison test or two-tailed Student's t test. If the data set does not meet the parametric test assumptions, either the Kruskal-Wallis test followed by the post hoc Dunn's multiple comparison or the Mann-Whitney rank sum test is performed. To test whether the Aβ levels in the bitransgenic mice were consistent with an additive sum of Aβ levels in the single transgenic littermates, a multiple linear regression with no intercept test is used. All comparisons are made between littermates. Drug response modelling is done excluding the control (0 mg/kg) samples. ED50 corresponds to the dose (mg/kg) required to induce 50% of maximal drug-induced response in the experiments. It is calculated using the Hill equation model for the log of ED50.

In vivo experiments are performed for candidate drug combinations. Positive results on learning and spatial memory are listed in Table 5 below.

TABLE 5

| Drug | Results in Morris Water Maze experiment |
|---|---|
| Terbinafine and Levosimendan | + |
| Terbinafine and Sulfisoxazole | + |
| Baclofen and Levosimendan | + |
| Sulfisoxazole and Levosimendan | + |
| Aminocaproic acid and Levosimendan | + |
| Aminocaproic acid and Terbinafine | + |

BIBLIOGRAPHY

1. Crook R., Verkkoniemi A., et al. (1998). A variant of Alzheimer's disease with spastic paraparesis and unusual plaques due to deletion of exon 9 of presenilin 1. Nat Med. 4(4): 452-5.
2. Houlden H., Baker M., et al. (2000). Variant Alzheimer's disease with spastic paraparesis and cotton wool plaques is caused by PS-1 mutations that lead to exceptionally high amyloid-beta concentrations. *Ann Neurol.* 48(5): 806-8.
3. Kwok J. B., Taddei K., et al. (1997). Two novel (M233T and R278T) presenilin-1 mutations in early-onset Alzheimer's disease pedigrees and preliminary evidence for association of presenilin-1 mutations with a novel phenotype. *Neuroreport.* 8(6): 1537-42.
4. Verkkoniemi A., Kalimo H., et al. (2001). Variant Alzheimer disease with spastic paraparesis: neuropathological phenotype. *J Neuropathol Exp Neurol.* 60(5): 483-92.
5. Citron M. (2004). Strategies for disease modification in Alzheimer's disease. *Nat Rev Neurosci.* 5(9): 677-85.
6. Suh Y. H. and Checler F. (2002). Amyloid precursor protein, presenilins, and alpha-synuclein: molecular pathogenesis and pharmacological applications in Alzheimer's disease. *Pharmacol Rev.* 54(3): 469-525.
7. Blacker D., Albert M. S., et al. (1994). Reliability and validity of NINCDS-ADRDA criteria for Alzheimer's disease. The National Institute of Mental Health Genetics Initiative. *Arch Neurol.* 51(12): 1198-204.
8. Rossor M. N., Fox N. C., et al. (1996). Clinical features of sporadic and familial Alzheimer's disease. *Neurodegeneration.* 5(4): 393-7.
9. Glenner G. G., Wong C. W., et al. (1984). The amyloid deposits in Alzheimer's disease: their nature and pathogenesis. *Appl Pathol.* 2(6): 357-69.
10. Ballatore C., Lee V. M., et al. (2007). Tau-mediated neurodegeneration in Alzheimer's disease and related disorders. Nat Rev Neurosci. 8(9): 663-72.
11. Bell K. F. and Claudio Cuello A. (2006). Altered synaptic function in Alzheimer's disease. *Eur J Pharmacol.* 545(1): 11-21.
12. Hardy J. A. and Higgins G. A. (1992). Alzheimer's disease: the amyloid cascade hypothesis. *Science.* 256(5054): 184-5.
13. Braak H. and Braak E. (1991). Neuropathological staging of Alzheimer-related changes. *Acta Neuropathol.* 82(4): 239-59.
14. Golde T. E. (2005). The Abeta hypothesis: leading us to rationally-designed therapeutic strategies for the treatment or prevention of Alzheimer disease. *Brain Pathol.* 15(1): 84-7.
15. Hardy J. and Selkoe D. J. (2002). The amyloid hypothesis of Alzheimer's disease: progress and problems on the road to therapeutics. *Science.* 297(5580): 353-6.
16. Selkoe D. J. (2000). The genetics and molecular pathology of Alzheimer's disease: roles of amyloid and the presenilins. *Neurol Clin.* 18(4): 903-22.
17. Huang Y. Z., Won S., et al. (2000). Regulation of neuregulin signaling by PSD-95 interacting with ErbB4 at CNS synapses. *Neuron.* 26(2): 443-55.
18. Naruse S., Thinakaran G., et al. (1998). Effects of PS1 deficiency on membrane protein trafficking in neurons. *Neuron.* 21(5):1213-21.
19. Leeuwen F. N., Kain H. E., et al. (1997). The guanine nucleotide exchange factor Tiam1 affects neuronal morphology; opposing roles for the small GTPases Rac and Rho. *J Cell Biol.* 139(3):797-807.
20. Ge G., Fernandez C. A., et al. (2007). Bone morphogenetic protein 1 processes prolactin to a 17-kDa antiangiogenic factor. *Proc Natl Acad Sci USA.* 104(24):10010-5.
21. Hardie D. G. (2007). AMP-activated/SNF1 protein kinases: conserved guardians of cellular energy. *Nat Rev Mol Cell Biol.* 8(10): 774-85.
22. Reihill J. A., Ewart M. A., et al. (2007). AMP-activated protein kinase mediates VEGF-stimulated endothelial NO production. *Biochem Biophys Res Commun.* 354(4):1084-8.
23. Ouchi N., Kobayashi H., et al. (2004). Adiponectin stimulates angiogenesis by promoting cross-talk between AMP-activated protein kinase and Akt signaling in endothelial cells. *J Biol Chem.* 279(2):1304-9.
24. Hug C., Wang J., et al. (2004). T-cadherin is a receptor for hexameric and high-molecular-weight forms of Acrp30/adiponectin. *Proc Natl Acad Sci USA.* 101(28):10308-13.
25. English D., Kovala A. T., et al. (1999). Induction of endothelial cell chemotaxis by sphingosine 1-phosphate and stabilization of endothelial monolayer barrier function by lysophosphatidic acid, potential mediators of hematopoietic angiogenesis. *J Hematother Stem Cell Res.* 8(6): 627-34.
26. Gorlach A., Klappa P., et al. (2006). The endoplasmic reticulum: folding, calcium homeostasis, signaling, and redox control. *Antioxid Redox Signal.* 8(9-10): 1391-418.
27. Verkhratsky A. (2004). Endoplasmic reticulum calcium signaling in nerve cells. *Biol Res.* 37(4): 693-9.
28. Cookson M. R. (2003). Neurodegeneration: how does parkin prevent Parkinson's disease? *Curr Biol.* 13(13): R522-4.
29. Sze C. I., Su M., et al. (2004). Down-regulation of WW domain-containing oxidoreductase induces Tau phosphorylation in vitro. A potential role in Alzheimer's disease. *J Biol Chem.* 279(29): 30498-506.
30. Walchli S., Curchod M. L., et al. (2000). Identification of tyrosine phosphatases that dephosphorylate the insulin receptor. A brute force approach based on "substrate-trapping" mutants. *J Biol Chem.* 275(13):9792-6.
31. Chang N. S., Doherty J., et al. (2003). JNK1 physically interacts with WW domain-containing oxidoreductase (WOX1) and inhibits WOX1-mediated apoptosis. *J Biol Chem.* 278(11):9195-202.
32. D'Orazi G., Cecchinelli B., et al. (2002). Homeodomain-interacting protein kinase-2 phosphorylates p53 at Ser 46 and mediates apoptosis. *Nat Cell Biol.* 4(1):11-9.
33. Zhu H., Wu L., et al. (2003). MDM2 and promyelocytic leukemia antagonize each other through their direct interaction with p53. *J Biol Chem.* 278(49):49286-92.
34. Rodrigues S., De Wever O., et al. (2007). Opposing roles of netrin-1 and the dependence receptor DCC in cancer cell invasion, tumor growth and metastasis. *Oncogene.* 26(38): 5615-25.
35. Taniguchi Y., Kim S. H., et al. (2003). Presenilin-dependent "gamma-secretase" processing of deleted in colorectal cancer (DCC). *J Biol Chem.* 278(33):30425-8.
36. Singer C., Figueroa-Masot X., Batchelor R., and Dorsa D. Mitogen-activated protein kinase pathway mediates estrogen neuroprotection after glutamate toxicity in primary cortical neurons. J. Neuroscience, 1999, 19(7):2455-2463.
37. McGowan E., et al. (2005) Aβ42 Is Essential for Parenchymal and Vascular Amyloid Deposition in Mice. Neuron 47: 191-199.
38. Leighty R. E. et al. (2008) Use of artificial neural networks to determine cognitive impairment and therapeutic effectiveness in Alzheimer's transgenic mice. Journal of Neuroscience Methods 167: 358-366.
39. Ashe K. H. (2001) Learning and memory in transgenic mice modelling Alzheimer's disease. Learning and Memory 8: 301-308.

40. Carlson G. A., et al. (1997) Genetic modification of the phenotypes produced by amyloid precursor protein overexpression in transgenic mice. Human Molecular Genetics 6:1951-1959.
41. Hsiao K., et al. (1996) Correlative memory deficits, Abeta elevation, and amyloid plaques in transgenic mice. Science 274: 99-102.
42. Greenberg S. M.* and Vonsattel J. P. (1997) Diagnosis of cerebral amyloid angiopathy. Sensitivity and specificity of cortical biopsy. Stroke 28(7):1418-22.
43. Schindowski K. et al. (2006) Alzheimer's Disease-Like Tau Neuropathology Leads to Memory Deficits and Loss of Functional Synapses in a Novel Mutated Tau Transgenic Mouse without Any Motor Deficits. Am J Pathol. 169: 599-616.
44. Lahiri D. K., et al. (2004) Dietary supplementation with melatonin reduces levels of amyloid beta-peptides in the murine cerebral cortex. *Journal of Pineal Research* 36:224-231.
45. Basha M. R., et al. (2005) The fetal basis of amyloidogenesis: exposure to lead and latent overexpression of amyloid precursor protein and beta-amyloid in the aging brain. *Journal of Neuroscience* 25: 823-829.
46. Lahiri D. K. et al. (2007) Experimental Alzheimer's Disease Drug Posiphen[(Phenserine] Lowers Amyloid-betaPeptide Levels in Cell Culture and Mice. Journal of Pharmacology and experimental therapeutics 320: 386-396.
47. Paris D., et al. (2005) Anti-angiogenic activity of the mutant Dutch A(beta) peptide on human brain microvascular endothelial cells. *Brain Res Mol Brain Res.* 136: 212-30.

The invention claimed is:

1. A method of treating Alzheimer's disease (AD) or an AD related disorder in a human in need thereof, the method comprising administering, per day, between 30 μg and 400 mg of carbamazine or a salt thereof or a sustained release formulation thereof to said human.

2. The method of claim 1, wherein the effective amount is an amount that protects endothelial or neuronal cells against beta-amyloid (Abeta) peptide toxicity.

3. The method of claim 1, further comprising administering to said human an effective amount of at least one additional compound selected from the group consisting of amlodipine, argatroban, cilostazol, cinacalcet, clopidogrel, dyphylline, fenoldopam, leflunomide, mepacrine, methimazole, phenformin, prilocaine, rifabutin, sulfisoxazole, tadalafil, terbinafine, cinnarizine, ciclopirox, eplerenone, carbenoxolone, sulodexide, amobarbital, cefotetan, erythrityl tetranitrate, methyclothiazide, risedronate, enprofylline, oxtriphylline, paramethadione, cefmenoxime, aprindine, etomidate, mitiglinide, benidipine, and zonisamide, salt(s) thereof and sustained release formulation(s) thereof, said additional compound being for combined, separate or sequential administration with carbamazine, the salt thereof or the sustained release formulation thereof.

4. The method of claim 3, wherein said at least one additional compound is selected from sulfisoxazole or terbinafine, salt(s) thereof or sustained release formulation(s) thereof.

5. A method of treating Alzheimer's disease (AD) or an AD related disorder in a human in need thereof, the method consisting of combined, separate or sequential administration to said human of an effective amount of acamprosate, or a salt thereof or a sustained release formulation and between 30 μg and 400 mg per day of carbamazine or a salt thereof or a sustained release formulation thereof.

6. A method for protecting neuronal cells against Abeta peptide toxicity in a human having AD, consisting of combined, separate or sequential administration to the human of acamprosate, or a salt thereof or sustained release formulation thereof, and between 30 μg and 400 mg per day of carbamazine or a salt thereof or a sustained release formulation thereof.

7. The method of claim 1, wherein carbamazine, the salt thereof or the sustained release formulation thereof, is administered with a pharmaceutically acceptable carrier or excipient.

8. The method of claim 1, wherein carbamazine, the salt thereof or the sustained release formulation thereof, is administered repeatedly to the human.

* * * * *